(12) United States Patent
Newhauser et al.

(10) Patent No.: US 10,952,763 B2
(45) Date of Patent: Mar. 23, 2021

(54) OCCLUSION-CROSSING DEVICES

(71) Applicant: Avinger, Inc., Redwood City, CA (US)

(72) Inventors: Richard R. Newhauser, Redwood City, CA (US); Theodore W. Ketai, San Francisco, CA (US); Peter H. Smith, Pacifica, CA (US); Myra L. Fabro, San Jose, CA (US)

(73) Assignee: Avinger, Inc., Redwood City, CA (US)

( * ) Notice: Subject to any disclaimer, the term of this patent is extended or adjusted under 35 U.S.C. 154(b) by 0 days.

(21) Appl. No.: 15/954,407

(22) Filed: Apr. 16, 2018

(65) Prior Publication Data
US 2019/0021760 A1 Jan. 24, 2019

Related U.S. Application Data

(63) Continuation of application No. 14/433,786, filed as application No. PCT/US2013/064346 on Oct. 10, (Continued)

(51) Int. Cl.
*A61B 17/3207* (2006.01)
*A61B 90/00* (2016.01)
(Continued)

(52) U.S. Cl.
CPC ........... *A61B 17/320758* (2013.01); *A61B 17/320783* (2013.01); *A61B 2017/003* (2013.01);
(Continued)

(58) Field of Classification Search
None
See application file for complete search history.

(56) References Cited

U.S. PATENT DOCUMENTS 3,367,727 A 2/1968 Ward et al.
3,908,637 A 9/1975 Doroshow
(Continued)

FOREIGN PATENT DOCUMENTS

CN 1875242 A 12/2006
CN 1947652 A 4/2007
(Continued)

OTHER PUBLICATIONS

Christensen; U.S. Appl. No. 16/069,545 entitled "OCT imaging catheter with lag correction," filed Jul. 12, 2018.
(Continued)

*Primary Examiner* — Shaun L David
(74) *Attorney, Agent, or Firm* — Shay Glenn LLP

(57) ABSTRACT

A catheter device for crossing occlusions includes an elongate catheter shaft, a rotatable tip configured to rotate relative to the elongate catheter shaft, a drive shaft, and an OCT imaging sensor. The rotatable tip includes a housing coupled with the elongate catheter shaft and cutting wedges extendable from the housing. The drive shaft has a central lumen extending therethrough and extends within the elongate catheter shaft. The drive shaft is coupled with the wedges and is configured to rotate the rotatable tip. The OCT sensor includes an optical fiber coupled with the rotatable tip and configured to rotate therewith. The elongate catheter shaft is configured to move axially over the drive shaft to extend and retract the wedges from the housing while maintaining a fixed position of the imaging sensor relative to the cutting wedges.

18 Claims, 37 Drawing Sheets

Related U.S. Application Data 2013, now Pat. No. 9,949,754, said application No. 14/433,786 is a continuation-in-part of application No. 13/433,049, filed on Mar. 28, 2012, now Pat. No. 8,644,913.

(60) Provisional application No. 61/712,149, filed on Oct. 10, 2012, provisional application No. 61/799,505, filed on Mar. 15, 2013, provisional application No. 61/468,396, filed on Mar. 28, 2011, provisional application No. 61/548,179, filed on Oct. 17, 2011.

(51) Int. Cl.
*A61B 17/32* (2006.01)
*A61B 17/00* (2006.01)

(52) U.S. Cl.
CPC ............. *A61B 2017/00336* (2013.01); *A61B 2017/00398* (2013.01); *A61B 2017/320004* (2013.01); *A61B 2017/320052* (2013.01); *A61B 2017/320056* (2013.01); *A61B 2090/3735* (2016.02)

(56) References Cited

U.S. PATENT DOCUMENTS

| | | |
|---|---|---|
| 4,178,935 A | 12/1979 | Gekhaman et al. |
| 4,487,206 A | 12/1984 | Aagard |
| 4,527,553 A | 7/1985 | Upsher |
| 4,552,554 A | 11/1985 | Gould et al. |
| 4,611,600 A | 9/1986 | Cohen |
| 4,621,353 A | 11/1986 | Hazel et al. |
| 4,639,091 A | 1/1987 | Huignard et al. |
| 4,651,753 A | 3/1987 | Lifton |
| 4,654,024 A | 3/1987 | Crittenden et al. |
| 4,681,106 A * | 7/1987 | Kensey ......... A61B 17/320758 604/22 |
| 4,686,982 A | 8/1987 | Nash |
| 4,691,708 A | 9/1987 | Kane |
| 4,771,774 A | 9/1988 | Simpson et al. |
| 4,841,977 A | 6/1989 | Griffith et al. |
| 4,857,046 A | 8/1989 | Stevens et al. |
| 4,920,961 A | 5/1990 | Grossi et al. |
| 4,926,858 A | 5/1990 | Gifford, III et al. |
| 5,000,185 A | 3/1991 | Yock |
| 5,018,529 A | 5/1991 | Tenerz et al. |
| 5,041,082 A | 8/1991 | Shiber |
| 5,047,040 A | 9/1991 | Simpson et al. |
| 5,085,662 A | 2/1992 | Willard |
| 5,099,850 A | 3/1992 | Matsui et al. |
| 5,178,153 A | 1/1993 | Einzig |
| 5,182,291 A | 1/1993 | Gubin et al. |
| 5,190,050 A | 3/1993 | Nitzsche |
| 5,192,291 A | 3/1993 | Pannek, Jr. |
| 5,312,415 A | 5/1994 | Palermo |
| 5,312,425 A | 5/1994 | Evans et al. |
| 5,321,501 A | 6/1994 | Swanson et al. |
| 5,333,142 A | 7/1994 | Scheps |
| 5,358,472 A | 10/1994 | Vance et al. |
| 5,366,464 A | 11/1994 | Belknap |
| 5,372,601 A | 12/1994 | Lary |
| 5,383,460 A | 1/1995 | Jang et al. |
| 5,383,467 A | 1/1995 | Auer et al. |
| 5,425,273 A | 6/1995 | Chevalier |
| 5,429,136 A | 7/1995 | Milo et al. |
| 5,431,673 A | 7/1995 | Summers et al. |
| 5,437,284 A | 8/1995 | Trimble |
| 5,459,570 A | 10/1995 | Swanson et al. |
| 5,460,168 A | 10/1995 | Masubuchi et al. |
| 5,465,147 A | 11/1995 | Swanson |
| 5,507,795 A | 4/1996 | Chiang et al. |
| 5,517,998 A | 5/1996 | Madison |
| 5,556,405 A | 9/1996 | Lary |
| 5,607,394 A | 3/1997 | Andersen et al. |
| 5,620,426 A | 4/1997 | Braithwaite |
| 5,632,754 A | 5/1997 | Farley et al. |
| 5,632,755 A | 5/1997 | Nordgren et al. |
| 5,674,232 A | 10/1997 | Halliburton |
| 5,681,336 A | 10/1997 | Clement et al. |
| 5,690,634 A | 11/1997 | Muller et al. |
| 5,722,403 A | 3/1998 | McGee et al. |
| 5,728,148 A | 3/1998 | Bostrom et al. |
| 5,795,295 A | 8/1998 | Hellmuth et al. |
| 5,807,339 A | 9/1998 | Bostrom et al. |
| 5,830,145 A | 11/1998 | Tenhoff |
| 5,836,957 A | 11/1998 | Schulz et al. |
| 5,843,050 A | 12/1998 | Jones et al. |
| 5,843,103 A | 12/1998 | Wulfman |
| 5,851,212 A | 12/1998 | Zirps et al. |
| 5,868,778 A | 2/1999 | Gershony et al. |
| 5,872,879 A | 2/1999 | Hamm |
| 5,904,651 A | 5/1999 | Swanson et al. |
| 5,907,425 A | 5/1999 | Dickensheets et al. |
| 5,935,075 A | 8/1999 | Casscells et al. |
| 5,938,602 A | 8/1999 | Lloyd |
| 5,938,671 A | 8/1999 | Katoh et al. |
| 5,951,482 A | 9/1999 | Winston et al. |
| 5,951,581 A | 9/1999 | Saadat et al. |
| 5,951,583 A | 9/1999 | Jensen et al. |
| 5,956,355 A | 9/1999 | Swanson et al. |
| 5,957,952 A | 9/1999 | Gershony et al. |
| 5,987,995 A | 11/1999 | Sawatari et al. |
| 5,997,558 A | 12/1999 | Nash |
| 6,001,112 A | 12/1999 | Taylor |
| 6,007,530 A | 12/1999 | Dornhofer et al. |
| 6,010,449 A | 1/2000 | Selmon et al. |
| 6,013,072 A | 1/2000 | Winston et al. |
| 6,017,359 A | 1/2000 | Gershony et al. |
| 6,027,514 A | 2/2000 | Stine et al. |
| 6,032,673 A | 3/2000 | Savage et al. |
| 6,048,349 A | 4/2000 | Winston et al. |
| 6,080,170 A | 6/2000 | Nash et al. |
| 6,106,515 A | 8/2000 | Winston et al. |
| 6,110,164 A | 8/2000 | Vidlund |
| 6,120,515 A | 9/2000 | Rogers et al. |
| 6,120,516 A | 9/2000 | Selmon et al. |
| 6,134,002 A | 10/2000 | Stimson et al. |
| 6,134,003 A | 10/2000 | Tearney et al. |
| 6,152,938 A | 11/2000 | Curry |
| 6,152,951 A | 11/2000 | Hashimoto et al. |
| 6,160,826 A | 12/2000 | Swanson et al. |
| 6,175,669 B1 | 1/2001 | Colston et al. |
| 6,176,871 B1 | 1/2001 | Pathak et al. |
| 6,183,432 B1 | 2/2001 | Milo |
| 6,193,676 B1 | 2/2001 | Winston et al. |
| 6,206,898 B1 | 3/2001 | Honeycutt et al. |
| 6,228,076 B1 | 5/2001 | Winston et al. |
| 6,241,744 B1 | 6/2001 | Imran et al. |
| 6,283,957 B1 | 9/2001 | Hashimoto et al. |
| 6,285,903 B1 | 9/2001 | Rosenthal et al. |
| 6,290,668 B1 | 9/2001 | Gregory et al. |
| 6,294,775 B1 | 9/2001 | Seibel et al. |
| 6,299,622 B1 | 10/2001 | Snow et al. |
| 6,307,985 B1 | 10/2001 | Murakami et al. |
| 6,375,615 B1 | 4/2002 | Flaherty et al. |
| 6,402,719 B1 | 6/2002 | Ponzi et al. |
| 6,416,527 B1 | 7/2002 | Berg et al. |
| 6,445,939 B1 | 9/2002 | Swanson et al. |
| 6,445,944 B1 | 9/2002 | Ostrovsky |
| 6,447,525 B2 | 9/2002 | Follmer et al. |
| 6,451,036 B1 | 9/2002 | Heitzmann et al. |
| 6,454,717 B1 | 9/2002 | Pantages et al. |
| 6,454,779 B1 | 9/2002 | Taylor |
| 6,482,216 B1 | 11/2002 | Hiblar et al. |
| 6,482,217 B1 | 11/2002 | Pintor et al. |
| 6,485,413 B1 | 11/2002 | Boppart et al. |
| 6,497,649 B2 | 12/2002 | Parker et al. |
| 6,501,551 B1 | 12/2002 | Tearney et al. |
| 6,503,261 B1 | 1/2003 | Bruneau et al. |
| 6,511,458 B2 | 1/2003 | Milo et al. |
| 6,517,528 B1 | 2/2003 | Pantages et al. |
| 6,542,665 B2 | 4/2003 | Reed et al. |
| 6,544,230 B1 | 4/2003 | Flaherty et al. |

(56) References Cited

U.S. PATENT DOCUMENTS

| | | |
|---|---|---|
| 6,546,272 B1 | 4/2003 | MacKinnon et al. |
| 6,551,302 B1 | 4/2003 | Rosinko et al. |
| 6,563,105 B2 | 5/2003 | Seibel et al. |
| 6,564,087 B1 | 5/2003 | Pitris et al. |
| 6,565,588 B1 | 5/2003 | Clement et al. |
| 6,572,563 B2 | 6/2003 | Ouchi et al. |
| 6,572,643 B1 | 6/2003 | Gharibadeh |
| 6,575,995 B1 | 6/2003 | Huter et al. |
| 6,579,298 B1 | 6/2003 | Bruneau et al. |
| 6,615,071 B1 | 9/2003 | Casscells, III et al. |
| 6,629,953 B1 | 10/2003 | Boyd |
| 6,638,233 B2 | 10/2003 | Corvi et al. |
| 6,645,217 B1 | 11/2003 | MacKinnon et al. |
| 6,657,727 B1 | 12/2003 | Izatt et al. |
| 6,666,874 B2 | 12/2003 | Heitzmann et al. |
| 6,687,010 B1 | 2/2004 | Horii |
| 6,728,571 B1 | 4/2004 | Barbato |
| D489,973 S | 5/2004 | Root et al. |
| 6,730,063 B2 | 5/2004 | Delaney et al. |
| 6,758,854 B1 | 7/2004 | Butler et al. |
| 6,760,112 B2 | 7/2004 | Reed et al. |
| 6,800,085 B2 | 10/2004 | Selmon et al. |
| 6,818,001 B2 | 11/2004 | Wulfman et al. |
| 6,824,550 B1 | 11/2004 | Noriega et al. |
| 6,830,577 B2 | 12/2004 | Nash et al. |
| 6,845,190 B1 | 1/2005 | Smithwick et al. |
| 6,852,109 B2 | 2/2005 | Winston et al. |
| 6,853,457 B2 | 2/2005 | Bjarklev et al. |
| 6,856,712 B2 | 2/2005 | Fauver et al. |
| 6,867,753 B2 | 3/2005 | Chinthammit et al. |
| 6,879,851 B2 | 4/2005 | McNamara et al. |
| 6,947,787 B2 | 9/2005 | Webler |
| 6,961,123 B1 | 11/2005 | Wang et al. |
| 6,970,732 B2 | 11/2005 | Winston et al. |
| 6,975,898 B2 | 12/2005 | Seibel |
| 7,068,878 B2 | 6/2006 | Crossman-Bosworth et al. |
| 7,074,231 B2 | 7/2006 | Jang |
| 7,126,693 B2 | 10/2006 | Everett et al. |
| 7,172,610 B2 | 2/2007 | Heitzmann et al. |
| 7,242,480 B2 | 7/2007 | Alphonse |
| 7,261,687 B2 | 8/2007 | Yang |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |
| 7,366,376 B2 | 4/2008 | Shishkov et al. |
| 7,382,949 B2 | 6/2008 | Bouma et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |
| 7,455,649 B2 | 11/2008 | Root et al. |
| 7,474,407 B2 | 1/2009 | Gutin |
| 7,485,127 B2 | 2/2009 | Nistal |
| 7,488,340 B2 | 2/2009 | Kauphusman et al. |
| 7,530,948 B2 | 5/2009 | Seibel et al. |
| 7,530,976 B2 | 5/2009 | MacMahon et al. |
| 7,538,859 B2 | 5/2009 | Tearney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,682,319 B2 | 3/2010 | Martin et al. |
| 7,706,863 B2 | 4/2010 | Imanishi et al. |
| 7,728,985 B2 | 6/2010 | Feldchtein et al. |
| 7,729,745 B2 | 6/2010 | Maschke |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,785,286 B2 | 8/2010 | Magnin et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,944,568 B2 | 5/2011 | Teramura et al. |
| 7,952,718 B2 | 5/2011 | Li et al. |
| 7,972,299 B2 | 7/2011 | Carter et al. |
| 8,059,274 B2 | 11/2011 | Splinter |
| 8,062,316 B2 | 11/2011 | Patel et al. |
| 8,068,921 B2 | 11/2011 | Prakash et al. |
| 8,313,493 B2 | 11/2012 | Fischer |
| 8,361,097 B2 | 1/2013 | Patel et al. |
| 8,548,571 B2 | 10/2013 | He et al. |
| 8,548,603 B2 | 10/2013 | Swoyer et al. |
| 8,632,557 B2 | 1/2014 | Thatcher et al. |
| 8,644,913 B2 | 2/2014 | Simpson et al. |
| 8,647,335 B2 | 2/2014 | Markus |
| 8,696,695 B2 | 4/2014 | Patel et al. |
| 8,911,459 B2 | 12/2014 | Simpson et al. |
| 9,119,662 B2 | 9/2015 | Moberg |
| 9,125,562 B2 | 9/2015 | Spencer et al. |
| 9,333,007 B2 | 5/2016 | Escudero et al. |
| 9,345,398 B2 | 5/2016 | Tachibana et al. |
| 9,345,406 B2 | 5/2016 | Spencer et al. |
| 9,345,510 B2 | 5/2016 | Patel et al. |
| 9,345,511 B2 | 5/2016 | Smith et al. |
| 9,351,757 B2 | 5/2016 | Kusleika |
| 9,498,247 B2 | 11/2016 | Patel et al. |
| 9,498,600 B2 | 11/2016 | Rosenthal et al. |
| 9,557,156 B2 | 1/2017 | Kankaria |
| 9,572,492 B2 | 2/2017 | Simpson et al. |
| 9,592,075 B2 | 3/2017 | Simpson et al. |
| 9,642,646 B2 | 5/2017 | Patel et al. |
| 9,788,790 B2 | 10/2017 | Black et al. |
| 9,854,979 B2 | 1/2018 | Smith et al. |
| 9,918,734 B2 | 3/2018 | Patel et al. |
| 9,949,754 B2 | 4/2018 | Newhauser et al. |
| 2001/0005788 A1 | 6/2001 | McGuckin, Jr. |
| 2001/0020126 A1 | 9/2001 | Swanson et al. |
| 2002/0019644 A1 | 2/2002 | Hastings et al. |
| 2002/0072706 A1 | 6/2002 | Hiblar et al. |
| 2002/0082585 A1 | 6/2002 | Carroll et al. |
| 2002/0082626 A1 | 6/2002 | Donohoe et al. |
| 2002/0111548 A1 | 8/2002 | Swanson et al. |
| 2002/0115931 A1 | 8/2002 | Strauss et al. |
| 2002/0147459 A1 | 10/2002 | Bashiri et al. |
| 2002/0158547 A1 | 10/2002 | Wood |
| 2003/0002038 A1 | 1/2003 | Mawatari |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1 | 5/2003 | Frot |
| 2003/0097044 A1 | 5/2003 | Rovegno |
| 2003/0120150 A1 | 6/2003 | Govari |
| 2003/0120295 A1 | 6/2003 | Simpson et al. |
| 2003/0125756 A1 | 7/2003 | Shturman et al. |
| 2003/0125757 A1 | 7/2003 | Patel et al. |
| 2003/0125758 A1 | 7/2003 | Simpson et al. |
| 2003/0139751 A1 | 7/2003 | Evans et al. |
| 2003/0181855 A1 | 9/2003 | Simpson et al. |
| 2004/0002650 A1 | 1/2004 | Mandrusov et al. |
| 2004/0039371 A1 | 2/2004 | Tockman et al. |
| 2004/0057667 A1 | 3/2004 | Yamada et al. |
| 2004/0059257 A1 | 3/2004 | Gaber |
| 2004/0082850 A1 | 4/2004 | Bonner et al. |
| 2004/0092915 A1 | 5/2004 | Levatter |
| 2004/0093001 A1 | 5/2004 | Hamada |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0186368 A1 | 9/2004 | Ramzipoor et al. |
| 2004/0193140 A1 | 9/2004 | Griffin et al. |
| 2004/0202418 A1 | 10/2004 | Ghiron et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |

(56) References Cited

U.S. PATENT DOCUMENTS

| | | |
|---|---|---|
| 2004/0254599 A1 | 12/2004 | Lipoma et al. |
| 2004/0260236 A1 | 12/2004 | Manning et al. |
| 2005/0020925 A1 | 1/2005 | Kleen et al. |
| 2005/0043614 A1 | 2/2005 | Huizenga et al. |
| 2005/0054947 A1 | 3/2005 | Goldenberg |
| 2005/0075660 A1 | 4/2005 | Chu et al. |
| 2005/0085708 A1 | 4/2005 | Fauver et al. |
| 2005/0085721 A1 | 4/2005 | Fauver et al. |
| 2005/0105097 A1 | 5/2005 | Fang-Yen et al. |
| 2005/0141843 A1 | 6/2005 | Warden et al. |
| 2005/0154407 A1 | 7/2005 | Simpson |
| 2005/0159712 A1 | 7/2005 | Andersen |
| 2005/0159731 A1 | 7/2005 | Lee |
| 2005/0171478 A1 | 8/2005 | Selmon et al. |
| 2005/0177068 A1 | 8/2005 | Simpson |
| 2005/0182295 A1 | 8/2005 | Soper et al. |
| 2005/0187571 A1 | 8/2005 | Maschke |
| 2005/0192496 A1 | 9/2005 | Maschke |
| 2005/0197623 A1 | 9/2005 | Leeflang et al. |
| 2005/0201662 A1 | 9/2005 | Petersen et al. |
| 2005/0203553 A1 | 9/2005 | Maschke |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0011820 A1 | 1/2006 | Chow-Shing et al. |
| 2006/0032508 A1 | 2/2006 | Simpson |
| 2006/0046235 A1 | 3/2006 | Alexander |
| 2006/0049587 A1 | 3/2006 | Cornwell |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235262 A1 | 10/2006 | Arnal et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |
| 2006/0264741 A1 | 11/2006 | Prince |
| 2006/0264743 A1 | 11/2006 | Kleen et al. |
| 2006/0264907 A1 | 11/2006 | Eskridge et al. |
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038125 A1 | 2/2007 | Kleen et al. |
| 2007/0038173 A1 | 2/2007 | Simpson |
| 2007/0078469 A1 | 4/2007 | Soito et al. |
| 2007/0078500 A1 | 4/2007 | Ryan et al. |
| 2007/0081166 A1 | 4/2007 | Brown et al. |
| 2007/0088230 A1 | 4/2007 | Terashi et al. |
| 2007/0106155 A1 | 5/2007 | Goodnow et al. |
| 2007/0135712 A1 | 6/2007 | Maschke |
| 2007/0167710 A1 | 7/2007 | Unal et al. |
| 2007/0196926 A1 | 8/2007 | Soito et al. |
| 2007/0219484 A1 | 9/2007 | Straub |
| 2007/0250080 A1 | 10/2007 | Jones et al. |
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0288036 A1 | 12/2007 | Seshadri |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bei et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0049234 A1 | 2/2008 | Seitz |
| 2008/0058629 A1 | 3/2008 | Seibel et al. |
| 2008/0065124 A1 | 3/2008 | Olson |
| 2008/0065125 A1 | 3/2008 | Olson |
| 2008/0065205 A1 | 3/2008 | Nguyen et al. |
| 2008/0095421 A1 | 4/2008 | Sun et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0132929 A1* | 6/2008 | O'Sullivan ........ A61B 17/1615 606/170 |
| 2008/0139897 A1 | 6/2008 | Ainsworth et al. |
| 2008/0146942 A1 | 6/2008 | Dala-Krishna |
| 2008/0147000 A1 | 6/2008 | Seibel et al. |
| 2008/0154293 A1 | 6/2008 | Taylor et al. |
| 2008/0177138 A1 | 7/2008 | Courtney et al. |
| 2008/0186501 A1 | 8/2008 | Xie |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |
| 2008/0275485 A1 | 11/2008 | Bonnette et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024084 A1 | 1/2009 | Khosla et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0028507 A1 | 1/2009 | Jones et al. |
| 2009/0043191 A1 | 2/2009 | Castella et al. |
| 2009/0073444 A1 | 3/2009 | Wang |
| 2009/0076447 A1 | 3/2009 | Casas et al. |
| 2009/0093764 A1 | 4/2009 | Pfeffer et al. |
| 2009/0099641 A1 | 4/2009 | Wu et al. |
| 2009/0125019 A1 | 5/2009 | Douglass et al. |
| 2009/0135280 A1 | 5/2009 | Johnston et al. |
| 2009/0137893 A1 | 5/2009 | Seibel et al. |
| 2009/0152664 A1 | 6/2009 | Tian et al. |
| 2009/0185135 A1 | 7/2009 | Volk |
| 2009/0196554 A1 | 8/2009 | Irisawa |
| 2009/0198125 A1 | 8/2009 | Nakabayashi et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0221920 A1 | 9/2009 | Boppart et al. |
| 2009/0235396 A1 | 9/2009 | Wang et al. |
| 2009/0244485 A1 | 10/2009 | Walsh et al. |
| 2009/0244547 A1 | 10/2009 | Ozawa |
| 2009/0264826 A1 | 10/2009 | Thompson |
| 2009/0284749 A1 | 11/2009 | Johnson et al. |
| 2009/0292199 A1 | 11/2009 | Bielewicz et al. |
| 2009/0306520 A1 | 12/2009 | Schmitt et al. |
| 2009/0316116 A1 | 12/2009 | Melville et al. |
| 2009/0318862 A1 | 12/2009 | Ali et al. |
| 2010/0004544 A1 | 1/2010 | Toida |
| 2010/0021926 A1 | 1/2010 | Noordin |
| 2010/0049225 A1 | 2/2010 | To et al. |
| 2010/0080016 A1 | 4/2010 | Fukui et al. |
| 2010/0082000 A1 | 4/2010 | Honeck et al. |
| 2010/0125253 A1 | 5/2010 | Olson |
| 2010/0130996 A1 | 5/2010 | Doud et al. |
| 2010/0217245 A1 | 8/2010 | Prescott |
| 2010/0241147 A1 | 9/2010 | Maschke |
| 2010/0253949 A1 | 10/2010 | Adler et al. |
| 2010/0292539 A1 | 11/2010 | Lankenau et al. |
| 2010/0292721 A1 | 11/2010 | Moberg |
| 2010/0312263 A1 | 12/2010 | Moberg et al. |
| 2010/0317973 A1 | 12/2010 | Nita |
| 2010/0324472 A1 | 12/2010 | Wulfman |
| 2011/0023617 A1 | 2/2011 | Yu et al. |
| 2011/0028977 A1 | 2/2011 | Rauscher et al. |
| 2011/0040238 A1 | 2/2011 | Wulfman et al. |
| 2011/0058250 A1 | 3/2011 | Liu et al. |
| 2011/0060186 A1 | 3/2011 | Tilson et al. |
| 2011/0071401 A1 | 3/2011 | Hastings et al. |
| 2011/0092955 A1 | 4/2011 | Purdy et al. |
| 2011/0106004 A1 | 5/2011 | Eubanks et al. |

(56) References Cited

U.S. PATENT DOCUMENTS

| | | |
|---|---|---|
| 2011/0118660 A1 | 5/2011 | Torrance et al. |
| 2011/0130777 A1 | 6/2011 | Zhang et al. |
| 2011/0144673 A1 | 6/2011 | Zhang et al. |
| 2011/0201924 A1 | 8/2011 | Tearney et al. |
| 2011/0208222 A1 | 8/2011 | Ljahnicky et al. |
| 2011/0257478 A1 | 10/2011 | Kleiner et al. |
| 2011/0264125 A1 | 10/2011 | Wilson et al. |
| 2011/0270187 A1 | 11/2011 | Nelson |
| 2011/0295148 A1 | 12/2011 | Destoumieux et al. |
| 2011/0301625 A1 | 12/2011 | Mauch et al. |
| 2011/0319905 A1 | 12/2011 | Palme et al. |
| 2012/0002928 A1 | 1/2012 | Irisawa |
| 2012/0004506 A1 | 1/2012 | Tearney et al. |
| 2012/0123352 A1 | 5/2012 | Fruland et al. |
| 2012/0238869 A1 | 9/2012 | Schmitt et al. |
| 2012/0259337 A1 | 10/2012 | del Rio et al. |
| 2012/0289971 A1 | 11/2012 | Segermark et al. |
| 2013/0035692 A1 | 2/2013 | Sorensen et al. |
| 2013/0072787 A1 | 3/2013 | Wallace et al. |
| 2013/0096589 A1 | 4/2013 | Spencer et al. |
| 2013/0211221 A1 | 8/2013 | Sunnarborg et al. |
| 2013/0223798 A1 | 8/2013 | Jenner et al. |
| 2013/0223801 A1 | 8/2013 | Bhagavatula et al. |
| 2013/0255069 A1 | 10/2013 | Higashi et al. |
| 2013/0266259 A1 | 10/2013 | Bhagavatula et al. |
| 2013/0287282 A1 | 10/2013 | Yokota et al. |
| 2013/0296695 A1 | 11/2013 | Spencer et al. |
| 2013/0317519 A1 | 11/2013 | Romo et al. |
| 2013/0325003 A1 | 12/2013 | Kapur et al. |
| 2014/0005534 A1 | 1/2014 | He et al. |
| 2014/0128893 A1 | 5/2014 | Guggenheimer et al. |
| 2014/0187949 A1 | 7/2014 | Zhao et al. |
| 2014/0222047 A1 | 8/2014 | Vreeman |
| 2014/0275996 A1 | 9/2014 | Stigall |
| 2014/0291985 A1 | 10/2014 | Cabrera et al. |
| 2014/0343410 A1 | 11/2014 | Graf et al. |
| 2014/0371718 A1 | 12/2014 | Alvarez et al. |
| 2015/0025310 A1 | 1/2015 | Everingham et al. |
| 2015/0036146 A1 | 2/2015 | Staloff |
| 2015/0141816 A1* | 5/2015 | Gupta ............... A61B 1/00165 600/427 |
| 2015/0164530 A1 | 6/2015 | Carver et al. |
| 2015/0208922 A1 | 7/2015 | Simpson et al. |
| 2015/0320975 A1 | 11/2015 | Simpson et al. |
| 2016/0008025 A1 | 1/2016 | Gupta et al. |
| 2016/0038030 A1 | 2/2016 | Smith et al. |
| 2016/0135832 A1 | 5/2016 | Simpson et al. |
| 2016/0144155 A1 | 5/2016 | Simpson et al. |
| 2016/0262791 A1 | 9/2016 | Patel et al. |
| 2016/0262839 A1 | 9/2016 | Spencer et al. |
| 2016/0338582 A1 | 11/2016 | Tachibana et al. |
| 2017/0065293 A1 | 3/2017 | Rosenthal et al. |
| 2017/0065295 A1 | 3/2017 | Patel et al. |
| 2017/0238803 A1 | 8/2017 | Kankaria |
| 2017/0238808 A1 | 8/2017 | Simpson et al. |
| 2017/0273711 A1 | 9/2017 | Simpson et al. |
| 2018/0042520 A1 | 2/2018 | Patel et al. |
| 2018/0049700 A1 | 2/2018 | Black et al. |
| 2018/0146978 A1 | 5/2018 | Patel et al. |
| 2018/0192880 A1 | 7/2018 | Patel et al. |

FOREIGN PATENT DOCUMENTS

| | | |
|---|---|---|
| CN | 101601581 A | 12/2009 |
| CN | 103027727 A | 4/2013 |
| DE | 202006018883.5 U | 2/2007 |
| EP | 0347098 A2 | 12/1989 |
| EP | 0808638 A1 | 11/1997 |
| EP | 0845692 B1 | 11/2005 |
| EP | 1859732 A1 | 11/2007 |
| EP | 2090245 A1 | 8/2009 |
| EP | 2353526 B1 | 9/2013 |
| JP | S62-275425 A | 11/1987 |
| JP | 03502060 A | 2/1990 |
| JP | 05103763 A | 4/1993 |
| JP | 06027343 A | 2/1994 |
| JP | 07308393 A | 11/1995 |
| JP | 2002214127 A | 7/2002 |
| JP | 2004509695 A | 4/2004 |
| JP | 2004516073 A | 6/2004 |
| JP | 2005114473 A | 4/2005 |
| JP | 2005230550 A | 9/2005 |
| JP | 2005249704 A | 9/2005 |
| JP | 2005533533 A | 11/2005 |
| JP | 2008175698 A | 7/2006 |
| JP | 2006288775 A | 10/2006 |
| JP | 2006313158 A | 11/2006 |
| JP | 2006526790 A | 11/2006 |
| JP | 2006326157 A | 12/2006 |
| JP | 200783053 A | 4/2007 |
| JP | 200783057 A | 4/2007 |
| JP | 2007225349 A | 9/2007 |
| JP | 2007533361 A | 11/2007 |
| JP | 2008023627 | 2/2008 |
| JP | 2008128708 A | 6/2008 |
| JP | 2008145376 A | 6/2008 |
| JP | 2008183208 A | 8/2008 |
| JP | 2008253492 A | 10/2008 |
| JP | 200914751 A | 1/2009 |
| JP | 2009509690 A | 3/2009 |
| JP | 200978150 A | 4/2009 |
| JP | 2009066252 A | 4/2009 |
| JP | 2009201969 A | 9/2009 |
| JP | 2010042182 A | 2/2010 |
| JP | 2010518900 A | 6/2010 |
| JP | 2011521747 A | 7/2011 |
| JP | 2012143558 A | 8/2012 |
| JP | 2012229976 A | 11/2012 |
| JP | 2012533353 A | 12/2012 |
| JP | 2013/524930 A | 6/2013 |
| JP | 2016508758 A | 3/2016 |
| KR | 2007/0047221 A | 5/2007 |
| RU | 2185859 C2 | 7/2002 |
| RU | 2218191 C2 | 12/2003 |
| WO | WO91/17698 A1 | 11/1991 |
| WO | WO99/23958 A1 | 5/1999 |
| WO | WO00/54659 A1 | 9/2000 |
| WO | WO01/15609 A1 | 3/2001 |
| WO | WO01/76680 A1 | 10/2001 |
| WO | WO2006/133030 A2 | 12/2006 |
| WO | WO2008/005888 A2 | 1/2008 |
| WO | WO2008/029506 A1 | 3/2008 |
| WO | WO2008/042987 A2 | 4/2008 |
| WO | WO2008/051951 A1 | 5/2008 |
| WO | WO2008/065600 A2 | 6/2008 |
| WO | WO2008/086613 A1 | 7/2008 |
| WO | WO2008/087613 A2 | 7/2008 |
| WO | WO2009/005779 A1 | 1/2009 |
| WO | WO2009/006335 A1 | 1/2009 |
| WO | WO2009/009799 A1 | 1/2009 |
| WO | WO2009/009802 A1 | 1/2009 |
| WO | WO2009/023635 A1 | 2/2009 |
| WO | WO2009/024344 A1 | 2/2009 |
| WO | WO2009/094341 A2 | 7/2009 |
| WO | WO2009/140617 A2 | 11/2009 |
| WO | WO2009/148317 A1 | 12/2009 |
| WO | WO2010/039464 A1 | 4/2010 |
| WO | WO2010/056771 A1 | 5/2010 |
| WO | WO2011/044387 A2 | 4/2011 |
| WO | WO2011/062087 A1 | 5/2011 |
| WO | WO2012/057940 A1 | 5/2012 |
| WO | WO2012/061935 A1 | 5/2012 |
| WO | WO2012/123737 A1 | 9/2012 |
| WO | WO2012/166332 A1 | 12/2012 |
| WO | WO2013/033490 A1 | 3/2013 |
| WO | WO2013/056262 A1 | 4/2013 |

(56) References Cited

FOREIGN PATENT DOCUMENTS

WO   WO2014/077870 A1   5/2014
WO   WO2014/093148 A2   6/2014

OTHER PUBLICATIONS

Aziz et al.; Chronic total occlusions—a stiff challege requiring a major breakthrough: is there light at the end of the tunnel?; Heart; vol. 91; suppl. III; pp. 42-48; Jun. 2005.

Emkey et al.; Analysis and evaluation of graded-index fiber-lenses; Journal of Lightwave Technology; vol. LT-5; No. 9; pp. 1156-1164; Sep. 1987.

Gonzalo et al.; Optical coherence tomography patterns of stent restenosis; Am. Heart J.; 158(2); pp. 284-293; Aug. 2009.

Han et al.; In situ Frog Retina Imaging Using Common-Path OCT with a Gold-Coated Bare Fiber Probe; CFM6; San Jose, California; CLEO, May 4, 2008; 2 pages.

Linares et al.; Arbitrary single-mode coupling by tapered and nontapered grin fiber lenses; Applied Optics; vol. 29; No. 28; pp. 4003-4007; Oct. 1, 1990.

Muller et al.; Time-gated infrared fourier-domain optical coherence tomography; CFM5; San Jose, California; CLEO May 4, 2008; 2 pages.

Sharma et al.; Optical coherence tomography based on an all-fiber autocorrelator using probe-end reflection as reference; CWJ13; San Francisco, California; CLEO May 16, 2004; 4 pages.

Shinkle et al.; Evaluation of stent placement and outcomes with optical coherence tomography; Interv. Cardiol.; 2(4); pp. 535-543; (manuscript version, 12 pages); Aug. 2010.

Suparno et al.; Light scattering with single-mode fiber collimators; Applied Optics; vol. 33; No. 30; pp. 7200-7205; Oct. 20, 1994.

Tanaka et al.; Challenges on the frontier of intracoronary imaging: atherosclerotic plaque macrophage measurement by optical coherence tomography; Journal of Biomedical Optics; 15(1); pp. (011104-1)-(011104-8); Jan.-Feb. 2010.

Wang et al.; Common-path endoscopic Fourier domain OCT with a reference Michelson interferometer; Proceedings of the SPIE; vol. 7566; pp. 75660L-75660L-7; Jan. 2010.

Smith et al.; U.S. Appl. No. 15/854,579 entitled "Chronic total occlusion crossing devices with imaging," filed Dec. 26, 2017.

Zung et al.; US. Appl. No. 15/741,773 entitled "Self-alignment mechanism for imaging catheter and drive assembly," filed Jan. 4, 2018.

Patel et al.; U.S. Appl. No. 15/922,058 entitled "Catheter system and method for boring through blocked vascular passages," filed Mar. 15, 2018.

Stamper et al.; Plaque characterization with optical coherence tomography. Journal of the American College of Cardiology. 47(8); pp. 69-79; Apr. 18, 2006.

Patel et al,, U.S. Appl. No. 16/681,807 entitled "Atherectomy catheters and occlusion crossing devices," filed Nov. 12, 2019.

Bayer Material Science.; Snap-Fit Joints for Plastics; 26 pages; retrieved from the Internet: ( https://web.archive.org/web/20121119232733if_/http://fab.cba.mit.edu:80/classes/S62.12/people/vemelle.noel/Plastic_Snap_fit_design.pdf) on Sep. 26, 2018.

Rosenthal et al.; U.S. Appl. No. 16/105,743 entitled "Atherectomy catheter with laterally-displaceable tip," filed Aug. 20, 2018.

Patel et al.; U.S. Appl. No. 16/148,246 entitled "Atherectomy catheter with serrated cutter," filed Oct. 1, 2018.

Simpson et al.; U.S. Appl. No. 16/194,183 entitled "Indetification of elastic lamina to guide interventional therapy," filed Nov. 16, 2018.

Fernandez et al., U.S. Appl. No. 16/305,136 entitled "Catheter device with detachable distal end," filed Nov. 28, 2018.

Patel et al.; U.S. Appl. No. 16/310,470 entitled "Atherectomy catheter with shapeable distal tip," filed Dec. 17, 2019.

Patel et al.; U.S. Appl. No. 16/490,903 entitled "Atherctomy catheter," filed Jul. 2, 2019.

Black et al; U.S. Appl. No. 16/506,851 entitled "Optical coherence tomography for biological imaging," filed Jul. 9, 2019.

Patel et al.; U.S. Appl. No. 16/516,093 entitled "High speed chronic total occlusion crossing devices," filed Jul. 18, 2019.

Choma et al.; Sensitivity advantage of swept source and fourier domain optical coherence tomography; Optics Express; 11(18); pp. 2183-2189; Sep. 8, 2003.

De Boer et al.; Improved signal-to-noise ratio in spectral-domain compared with time-domain optical coherence tomography; Optics Letters; 28(21); pp. 2067-2069; Nov. 2003.

Leitgeb et al.; Performance of fourier domain vs time domain optical coherence tomography; Optics Express; 11(8); pp. 889-894; Apr. 21, 2003.

Rollins et al.; Optimal interferometer designs for optical coherence tomography; Optics Letters; 24(21); pp. 1484-1486; Nov. 1999.

Tachibana et al.; U.S. Appl. No. 16/372,112 entitled "Atherectomy catheter drive assemblies," filed Apr. 1, 2019.

Radjabi et al.; U.S. Appl. No. 16/347,840 entitled "Methods, systems and apparatuses for displaying real-time catheter position," filed May 7, 2019.

Schmitt et al.; A new rotational thrombectomy catheter: System design and first clinical experiences; Cardiovascular and Interventional Radiology; Springer-Verlag; 22(6); pp. 504-509.

Sharma et al.: Common-path optical coherence tomography with side-viewing bare fiber probe for endoscopic optical coherence tomography; vol. 78: 113102; 5 pages; Nov. 6, 2007.

Patel et al.: U.S. Appl. No. 16/801,047 entitled "Micro-molded anamorphic reflector lens for image guided therapeutic/diagnostic catheters," filed Feb. 25, 2020.

* cited by examiner

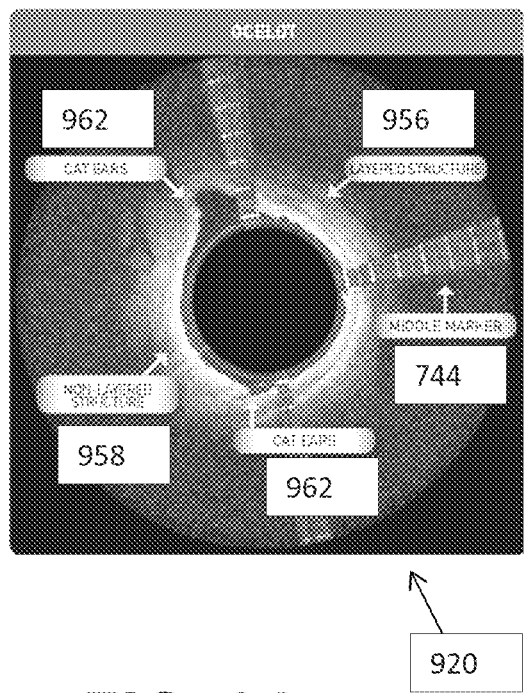
FIG. 9A
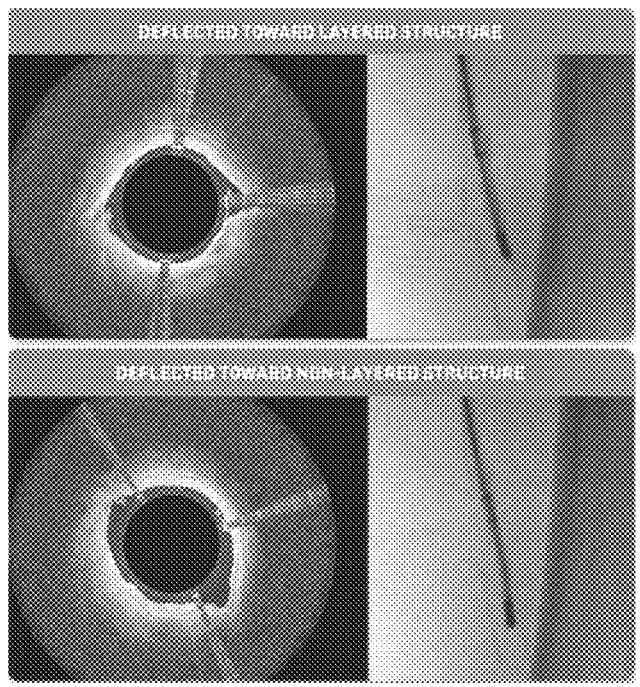
FIG. 9B
FIG. 9C

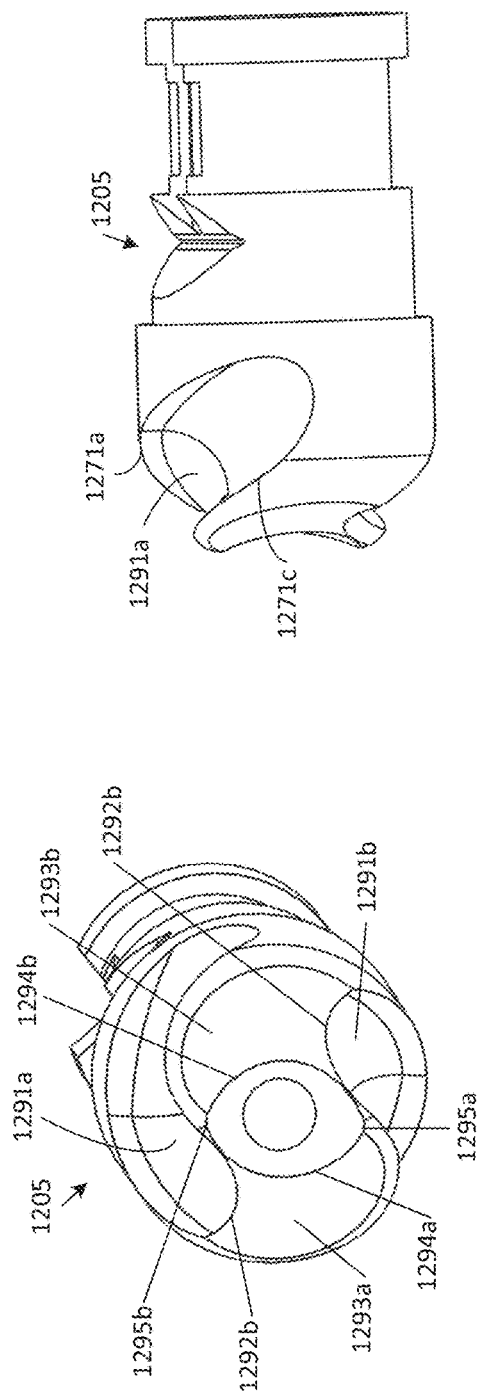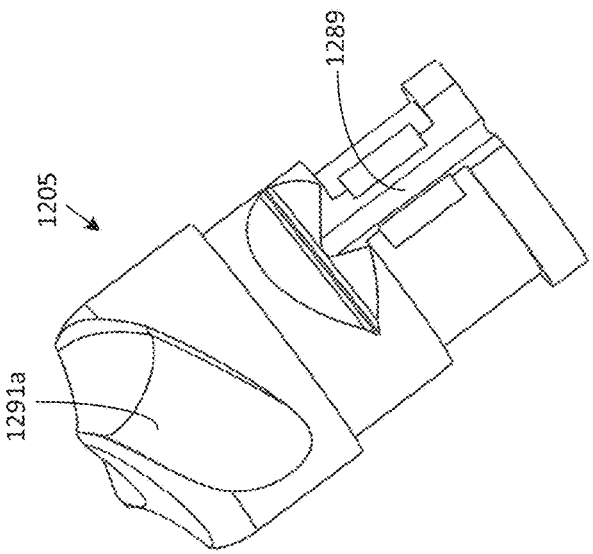
FIG. 12C
FIG. 12D
FIG. 12B

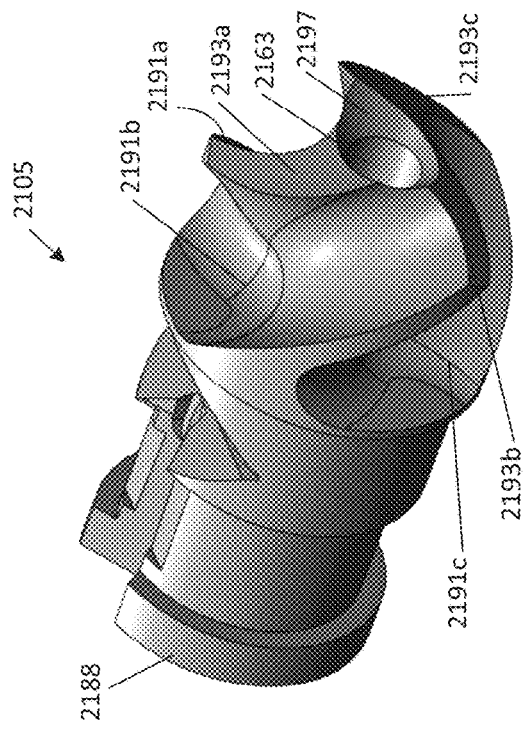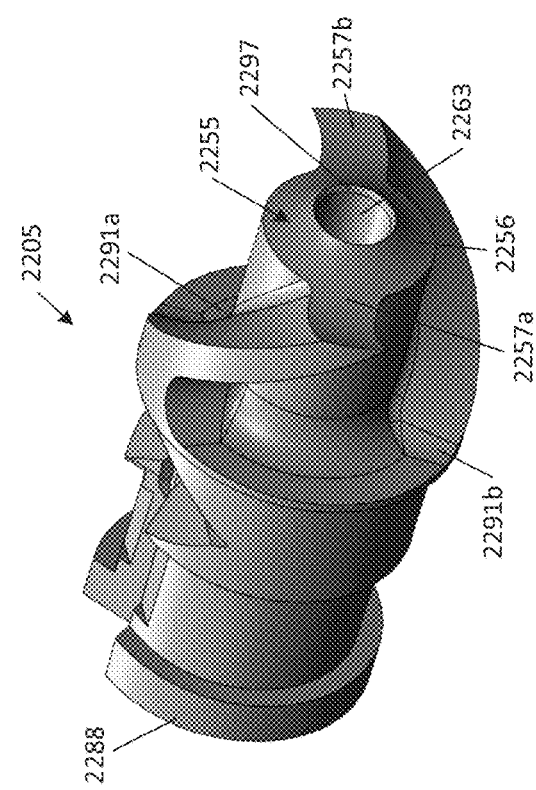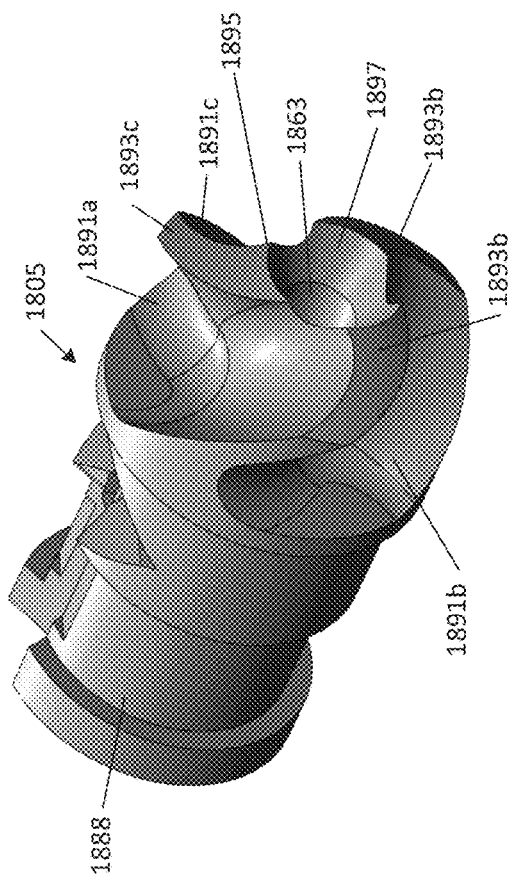
FIG. 15E
FIG. 15D
FIG. 15A

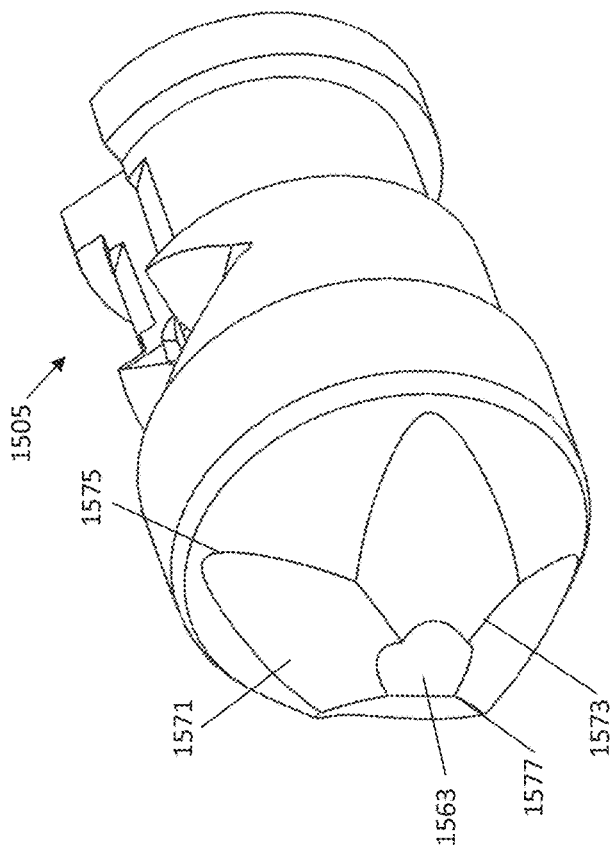
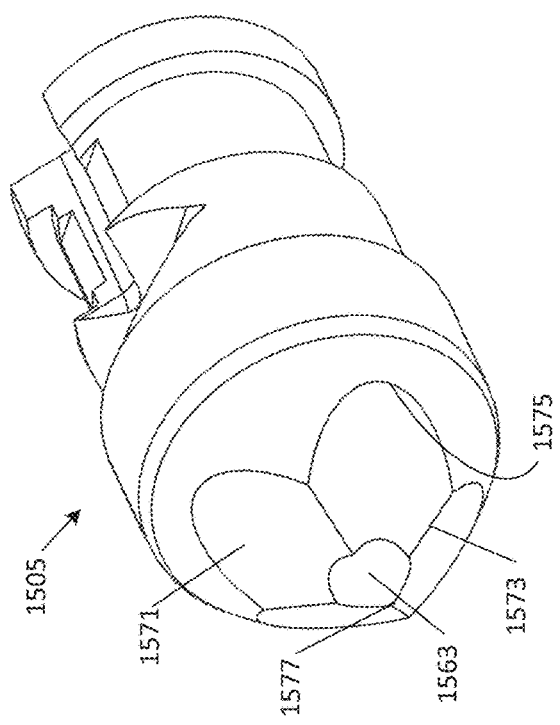

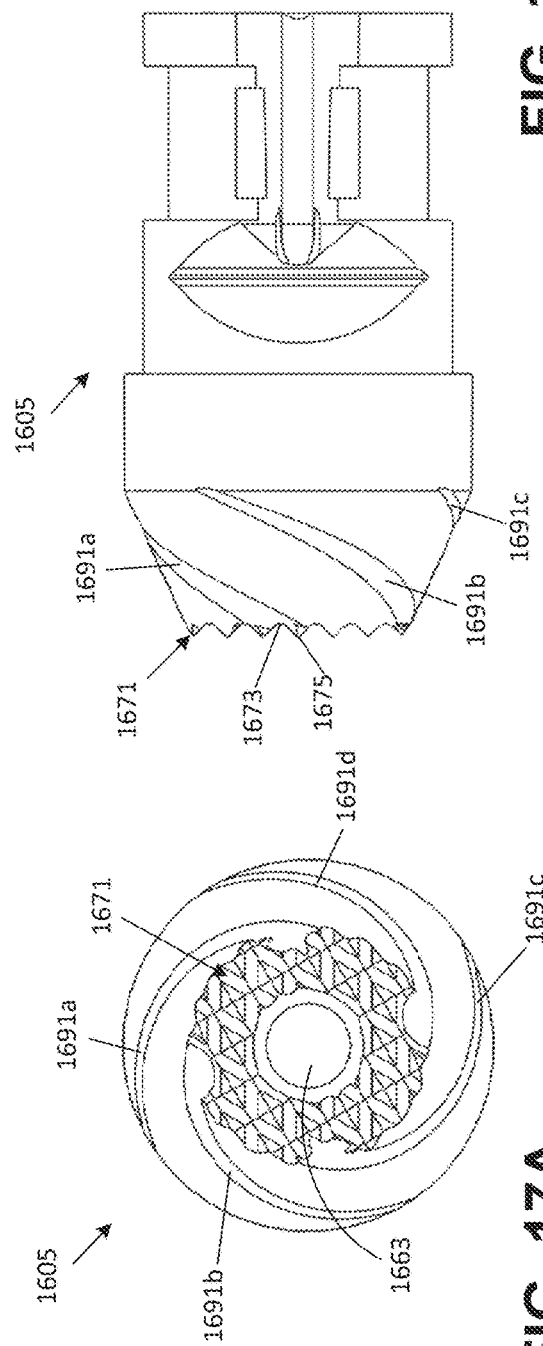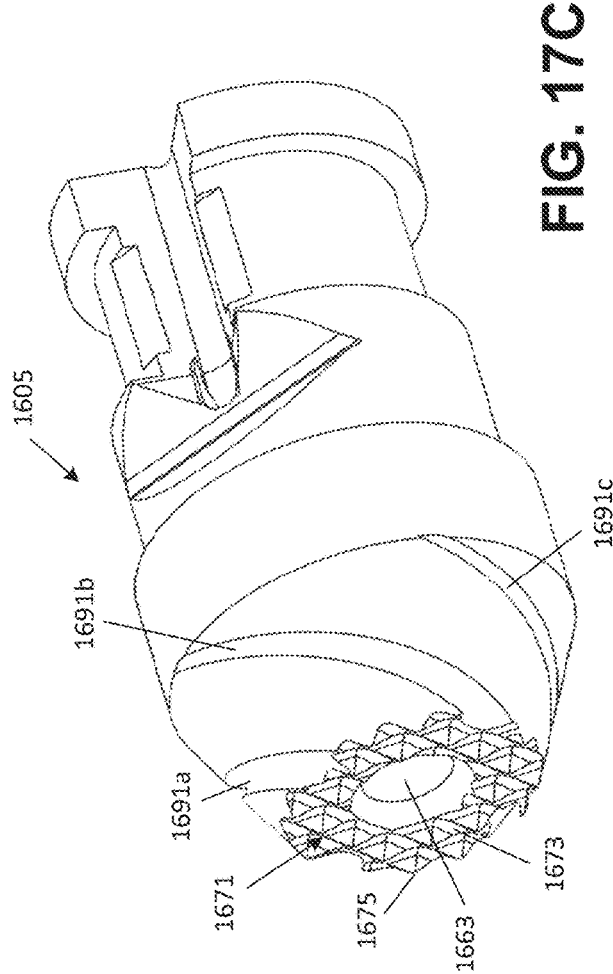
FIG. 17A
FIG. 17B
FIG. 17C

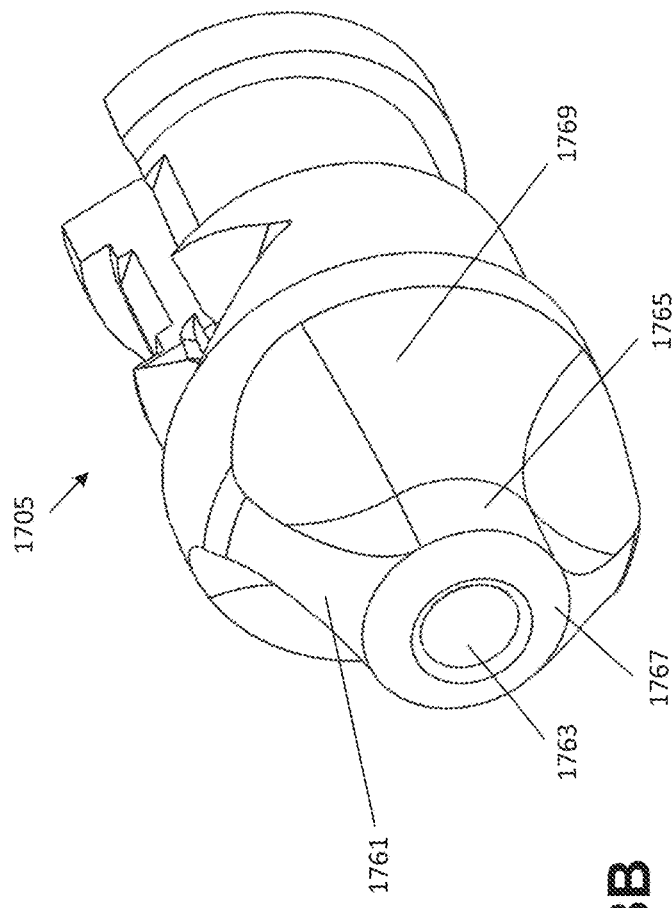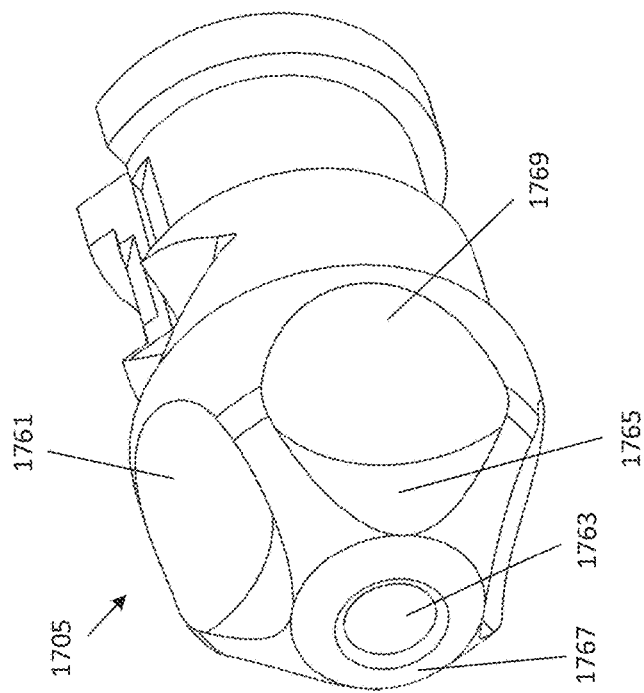

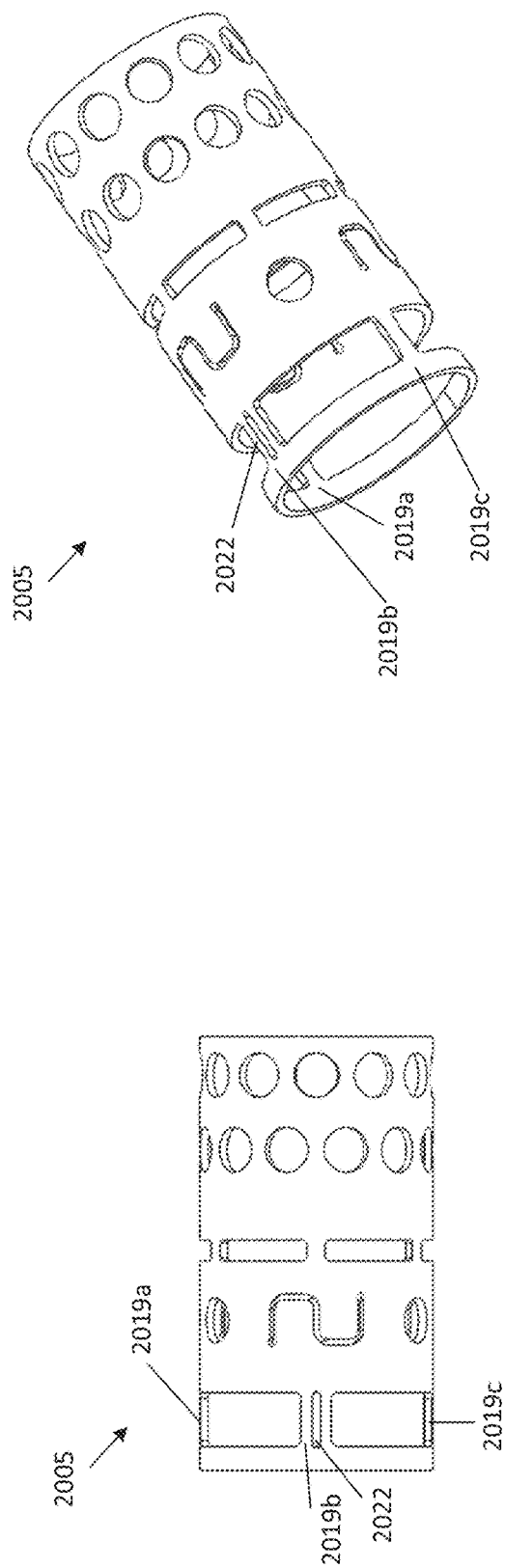
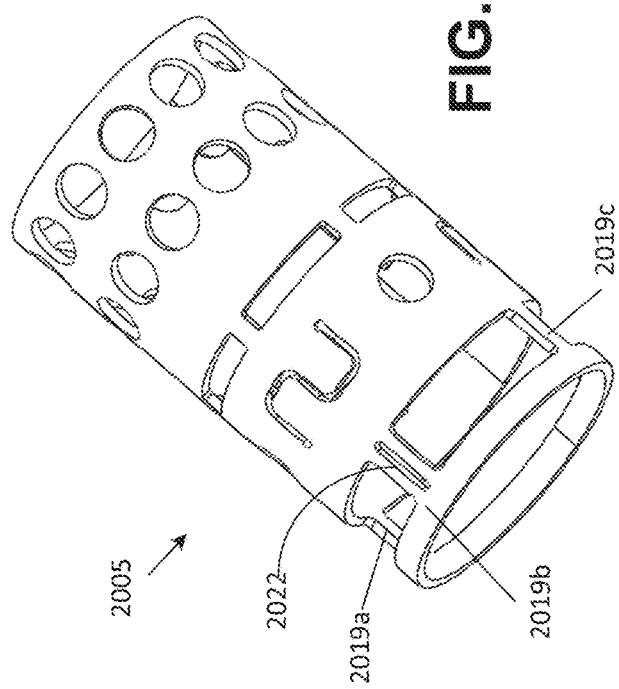
FIG. 20A
FIG. 20B
FIG. 20C

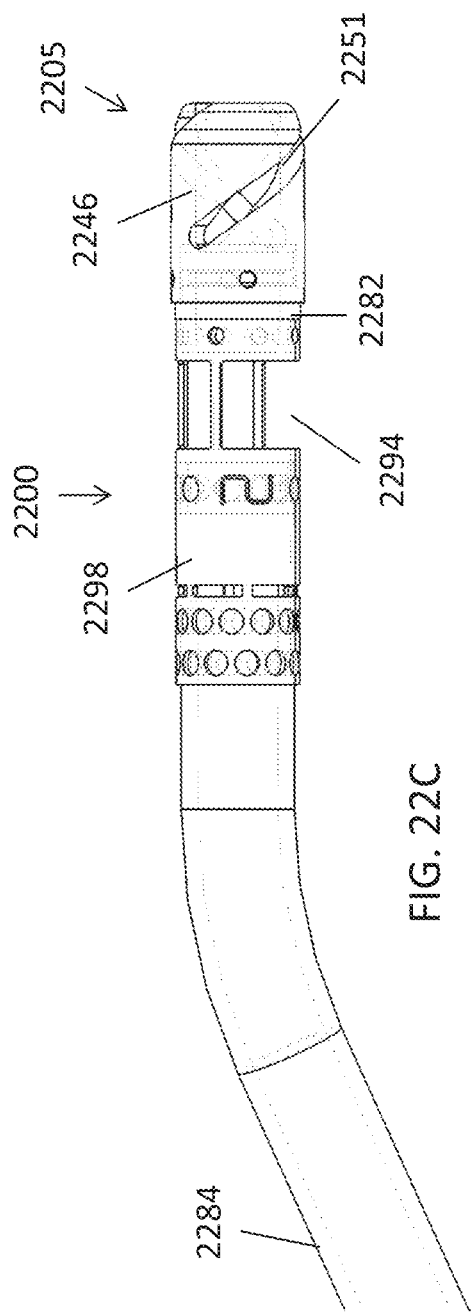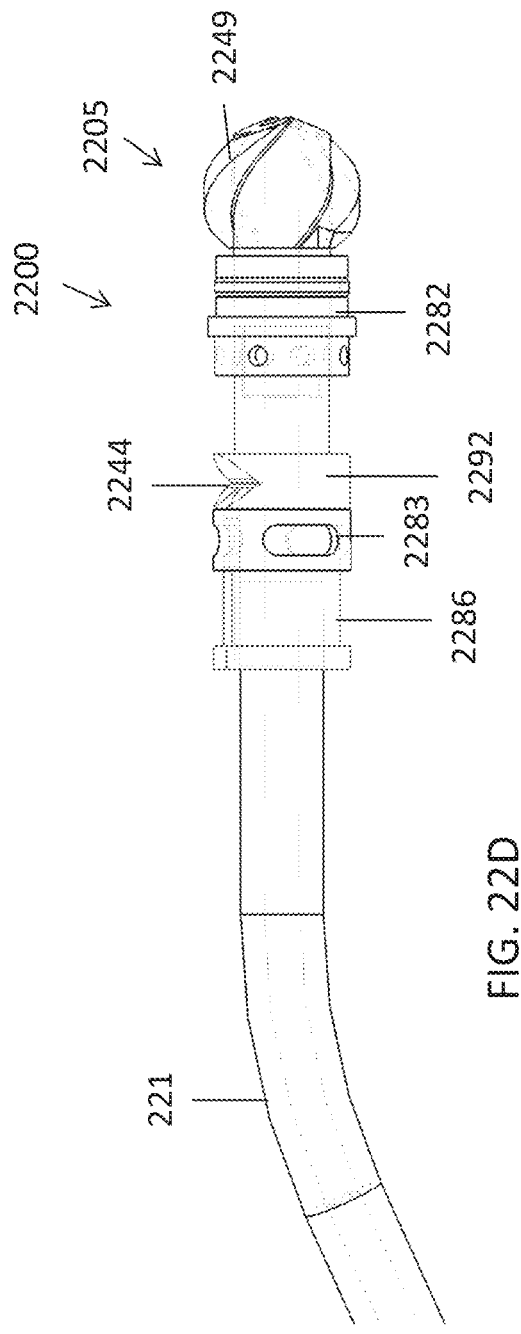

OCCLUSION-CROSSING DEVICES

CROSS REFERENCE TO RELATED APPLICATIONS

This application is a continuation of U.S. application Ser. No. 14/433,786, titled "OCCLUSION-CROSSING DEVICES", filed Apr. 6, 2015, which is a 371 of PCT/US2013/064346, titled "OCCLUSION-CROSSING DEVICES," filed Oct. 10, 2013, which claims priority to U.S. Provisional Patent Application No. 61/712,149, titled "OCCLUSION-CROSSING DEVICES," filed Oct. 10, 2012 and to U.S. Provisional Patent Application No. 61/799,505, titled "OCCLUSION-CROSSING DEVICES," filed Mar. 15, 2013. U.S. application Ser. No. 14/433,786, titled "OCCLUSION-CROSSING DEVICES", filed Apr. 6, 2015 is also a continuation-in-part of U.S. patent application Ser. No. 13/433,049, filed Mar. 28, 2012, titled "OCCLUSION-CROSSING DEVICES, IMAGING, AND ATHERECTOMY DEVICES," now U.S. Pat. No. 8,644,913, which claims priority to U.S. Provisional Patent Application No. 61/468,396, filed Mar. 28, 2011 and titled "OCCLUSION-CROSSING DEVICES, IMAGING, AND ATHERECTOMY DEVICES" and U.S. Provisional Patent Application No. 61/548,179, filed Oct. 17, 2011 and titled "OCCLUSION-CROSSING DEVICES, IMAGING, AND ATHERECTOMY DEVICES, each of which are incorporated by reference in their entirety."

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are catheters and specifically, catheters that may include a rotating distal tip having both a directional cutting element and an OCT imaging sensor. More specifically, occlusion-crossing catheters having both imaging and a tip configured to extend in and out of a protective housing are described herein.

BACKGROUND

Peripheral artery disease (PAD) affects millions of people in the United States alone. PAD is a silent, dangerous disease that can have catastrophic consequences when left untreated. PAD is the leading cause of amputation in patients over 50 and is responsible for approximately 160,000 amputations in the United States each year.

Peripheral artery disease (PAD) is a progressive narrowing of the blood vessels most often caused by atherosclerosis, the collection of plaque or a fatty substance along the inner lining of the artery wall. Over time, this substance hardens and thickens, which may interfere with blood circulation to the arms, legs, stomach and kidneys. This narrowing forms an occlusion, completely or partially restricting flow through the artery. Blood circulation to the brain and heart may be reduced, increasing the risk for stroke and heart disease.

Interventional treatments for PAD may include endarterectomy and/or atherectomy. Endarterectomy is surgical removal of plaque from the blocked artery to restore or improve blood flow. Endovascular therapies such as atherectomy are typically minimally invasive techniques that open or widen arteries that have become narrowed or blocked. Other treatments may include angioplasty to open the artery. For example, a balloon angioplasty typically involves insertion of a catheter into a leg or arm artery and positioning the catheter such that the balloon resides within the blockage. The balloon, connected to the catheter, is expanded to open the artery. Surgeons may then place a wire mesh tube, called a stent, at the area of blockage to keep the artery open.

Such minimally invasive techniques (e.g., atherectomy, angioplasty, etc.) typically involve the placement of a guidewire through the occlusion. Using the guidewire, one or more interventional devices may be positioned to remove or displace the occlusion. Unfortunately, placement of the guidewire, while critical for effective treatment, may be difficult. In particular, when placing a guidewire across an occlusion, it may be difficult to pass the guidewire through the occlusion while avoiding damage to the artery. For example, it is often difficult to prevent the guidewire from directing out of the lumen into the adventitia and surrounding tissues, potentially damaging the vessel and preventing effective treatment of the occlusion.

As a result, occlusion-crossing devices, intended to assist in the passing of the guidewire through the occlusion, have been developed. Many of the devices, however, suffer from having poor cutting surfaces that either drill through the occlusion off-center or mash the occlusion rather than drilling therethrough.

Accordingly, occlusion crossing catheter devices having cutting surfaces that are designed to address some of these concerns are described herein.

SUMMARY OF THE DISCLOSURE

The present invention relates to catheters having a rotating distal tip region that includes an OCT imaging sensor and may include one or more tissue dissecting elements. These catheters may also include a central passage or lumen that opens distally, extending along the length of the catheter body, that may be used to pass a guidewire. In general, the catheters described herein may be configured as: (1) guidewire support/placement catheters; (2) support/placement imaging catheters; (3) occlusion crossing catheters or (4) occlusion crossing imaging catheters. Any of these catheter variations may include one or more of the elements described herein, and any of these catheter variations may be used to treat a disorder, particularly peripheral artery disease. Systems including any of these catheters are also described. For convenience, in the description below, these catheters may be referred to as occlusion crossing catheters. It is to be understood that any of the catheters described herein may be configured as occlusion crossing catheters.

In general, a catheter may include a flexible elongate body, a proximal handle (or handle region), and a distal rotating tip. The distal tip may have a corkscrew-like rotating tip which is configured to rotate to enhance forward motion (e.g., at low rates of rotation) without cutting or drilling through the tissue. Rather than drilling, the tip may be configured to prevent or reduce static friction, avoiding damage to the luminal walls of the vessel and preventing the tip from passing through the adventitia.

The tip may be configured to rotate at very low speeds (e.g., less than about 300 revolutions/min, less than 100 rev/min, less than 50 rev/min, less than 30 rev/min, e.g., between about 1 and about 30 rev/min, etc.) at a constant or variable rate. In many variations, particularly but not necessarily those including an imaging modality (e.g., OCT) with an imaging sensor affixed to the rotating tip, the tip may rotate automatically both clockwise and counterclockwise, alternately. For example, the device or system may be configured to rotate the distal tip first clockwise, then counterclockwise. The clockwise and counterclockwise rotations may be performed continuously for a predetermined number of revolutions or partial revolutions, such as more than one revolution (e.g., approximately 2 revolutions, 2.5 revolutions, 3 revolutions, 5 revolutions, 8 revolutions, 10 revolutions, 12 revolutions, 20 revolutions, 50 revolutions, 100 revolutions, or any number of revolution between 1 and 500, including fractions of revolutions). In some variations, the number of rotations is not predetermined, but may be based on timing or on feedback from the catheter or system. For example, the distal tip (and therefore the OCT imaging sensor) may be rotated in a first direction until a tension or resistance threshold is reached, then rotated in the opposite direction until a tension or resistance threshold is reached in that direction. This process may then be repeated.

Any of the catheters described herein may include one or more tissue dissecting cutting edges on the rotating distal tip. In some variations, the forward edge of the catheter includes one or more helical edges, which may be referred to as wedges. The helical edges may be arranged at the distal end of the device. The edge may have a small diameter, particularly as compared with the ultimate diameter of the device. In one embodiment, the rotatable distal tip includes helical flutes that terminate in distal cutting surfaces. The distal cutting surfaces can come together at sharp points configured to slice through tissue. The rotatable distal tip can further include a countersink surrounding the guidewire lumen configured to center the tip around the occlusion. Other tip designs are possible. For example, the tip can include grinding edges and/or paddles.

Any of the catheter variations described herein may include a central lumen through which a guidewire may be passed for placement across an occlusion using the device. The central lumen typically extends along the length of the device from the proximal end or a region distal to the proximal end, to the distal end of the catheter. Thus, the catheter may include a distal opening. This central lumen may be referred to as a guidewire lumen. In some variations, the device is configured to pass through a lesion or occlusion (or an occluded region or regions of a vessel) to position the catheter beyond the occlusion before a guidewire is passed through the catheter. Alternatively, the guidewire may be housed or held within the lumen while the device is advanced through the occlusion or occluded region of a vessel, such as an artery, vein, or duct, for example a peripheral artery, vein, or bile duct.

The catheters described herein can be configured to apply optical coherence tomography (OCT) to image the tissue. Thus, the catheters described herein can include an imaging sensor, such as an OCT imaging sensor. An OCT imaging sensor may include the distal end of an optical fiber and a mirror for directing light in/out of the optical fiber. The optical fiber may be affixed to the distal tip structure. The imaging sensor may be oriented to image the vessel ahead of the device, perpendicular to the device, and/or behind the device tip. The mirror or reflector may be used to direct the light path entering and exiting the end of the optical fiber to fix the imaging direction for the device. For example, the optical fiber and mirror may be fixed to the rotating distal tip region and may be embedded in a transparent or translucent medium (including transparent cement or other fixative).

An optical fiber of the OCT system can be attached only to the rotating distal tip and at a proximal end but be free to move within the device lumen. As the distal end or tip of the device rotates, the optical fiber may wrap and unwrap around the inner lumen as the distal end/tip is rotated clockwise and counterclockwise. Thus, the length of the optical fiber extending from this affixed region at the rotatable distal tip to the proximal end of the catheter is loose within the catheter body and free to wind/unwind around the catheter body. The inventors have discovered that this loose arrangement of the optical fiber creates advantages compared to systems in which an optical fiber is held along its length or prohibited from off-axis winding, including ease of construction and enhanced catheter flexibility. Thus, any of the catheters described herein may be adapted to allow and control the winding/unwinding of the optical fiber within the catheter, and the optical fiber may be located within the catheter in an off-axis position.

In general, in one embodiment, a catheter device for crossing occlusions includes an elongate catheter shaft, a rotatable tip configured to rotate relative to the elongate catheter shaft, a drive shaft, and an OCT imaging sensor. The rotatable tip includes a housing coupled with the elongate catheter shaft and cutting wedges extendable from the housing. The drive shaft has a central lumen extending therethrough and extends within the elongate catheter shaft. The drive shaft is coupled with the wedges and is configured to rotate the rotatable tip. The OCT sensor includes an optical fiber coupled with the rotatable tip and configured to rotate therewith. The elongate catheter shaft is configured to move axially over the drive shaft to extend and retract the wedges from the housing while maintaining a fixed position of the imaging sensor relative to the cutting wedges.

This and other embodiments can include one or more of the following features. A handle can be axially fixed to the drive shaft, and the elongate catheter shaft can be configured to move axially relative to the handle to control the extension of the wedges from the housing. The elongate catheter shaft can be configured to move distally over the drive shaft to position the wedges in a retracted configuration and to move proximally over to the drive shaft to position the wedges in an extended configuration. Distal movement of the catheter shaft can push the housing over the wedges, and proximal movement of the catheter can pull the housing off of the wedges. The cutting wedges can include spiral wedges. The housing can include spiral slots configured such that the spiral wedges are extendable therethrough. The optical fiber can be configured to wrap around the drive shaft. A torque knob can be connected to the elongate catheter shaft and configured to translate the elongate catheter shaft without translating the drive shaft or the optical fiber. The elongate catheter shaft can include includes an imaging window therein, and the imaging window can have a length that is greater than or equal to a length of the wedges when the wedges are extended from the housing. The drive shaft can include a central lumen extending therethrough configured to pass a guidewire.

In general, in one embodiment, a method of crossing occlusion includes inserting a catheter into a lumen, the catheter including an elongate catheter shaft and a rotatable tip; extending cutting wedges from a housing of the rotatable tip by pulling the elongate catheter shaft proximally; rotating the housing and the cutting wedges by rotating a drive shaft attached to the cutting wedges to cut through tissue within the lumen; and imaging the lumen with an OCT sensor attached to the rotatable tip In general, this and other embodiments include one or more of the following features. The method can further include retracting the wedges into the housing by pushing the elongate catheter shaft distally. Imaging the lumen can include maintaining the OCT sensor at a fixed location relative to the wedges both when the wedges are extended from the housing and when the wedges are retracted into the housing. Extending the cutting wedges can include activating a mechanism on a handle attached to the catheter. The imaging sensor can include an optical fiber, and the method can further include wrapping the optical fiber around the drive shaft. Rotating the housing and the cutting wedges can include rotating the housing and cutting wedges alternately clockwise and counterclockwise. Each alternate rotation can include a substantially equivalent number of revolutions. The drive shaft can include a central lumen therein, and the method further include extending a guidewire through the central lumen.

In general, in one embodiment, a catheter device for crossing occlusions includes an elongate body. The catheter device further includes a central lumen extending within the elongate body from a proximal end of the elongate body to a distal end of the elongate body. The catheter device further includes a rotatable tip at the distal end of the elongate body and configured to rotate relative to the elongate body. The rotatable tip includes helical flutes that terminate in distal cutting surfaces and a countersink surrounding the central lumen.

This and other embodiments can include one or more of the following features. The helical flutes can be rimmed by cutting edges that extend radially between the helical flutes. The distal cutting surfaces can come together at sharp distal-facing points configured to slice through tissue. The rotatable tip can include a substantially smooth, curved outer surface that presents an atraumatic tissue-contacting surface when rotated in a first direction and that further presents a dissecting surface when rotated in a second direction. Each of the helical flutes can extend less than half way around a circumference of the tip. The countersink can be framed by knife-like edges at the distal-most end of the tip. The knife-like edges can be formed by the junction of the distal cutting surfaces and the countersink. The helical flutes can have a pitch of greater than 0.10 inches. The rotatable tip can further include a proximal stem portion having a channel therein configured to hold a distal end of an optical fiber for optical coherence tomography imaging. The channel can have a rounded base.

In general, in one embodiment, a catheter device for crossing occlusions includes an elongate catheter shaft having a fixed jog therein proximal to a distal end of the catheter. The fixed jog has a coiled reinforcement therearound. The catheter device further includes a central lumen extending within the elongate catheter shaft from a proximal end of the elongate body to a distal end of the elongate body. The catheter device further includes a rotatable tip at the distal end of the elongate body and configured to rotate relative to the elongate body and an OCT imaging sensor comprising an optical fiber extending through the elongate catheter body and coupled with the rotatable tip so as to rotate therewith.

BRIEF DESCRIPTION OF THE DRAWINGS

FIGS. 9A-9C show screen captures used to aid steering an exemplary catheter device.

FIGS. 12A-12F show a variation of a rotating tip having helical flutes and a countersink.

FIGS. 15A-15E show variations of a rotating tip having helical flutes, a countersink, and different designs of aggressive cutting edges.

FIGS. 16A-16B show variations of a rotating tip having slanted surfaces forming grinding edges.

FIGS. 17A-17C show a variation of a rotating tip having a distal grinding surface with an array of sharp points therein.

FIGS. 18A-18B show variations of a rotating tip having paddles.

FIG. 19A shows the wedges extended. FIG. 19B shows the wedges retracted.

FIG. 19C shows the torque knob position when the distal wedges are extended. FIG. 19D shows the torque knob position when the distal wedges are retracted.

FIGS. 20A-20C shows an exemplary spine or marker arrangement for orienting a catheter during OCT imaging.

FIGS. 22A-22F show another embodiment of an exemplary occlusion-crossing catheter having a rotating distal tip and extendable wedges. FIG. 22A shows the wedges retracted. FIG. 22B shows the wedges extended. FIG. 22C shows the outer shaft assembly. FIG. 22D shows the inner shaft assembly. FIG. 22E shows the housing over the inner shaft assembly of FIG. 22D with the wedges retracted. FIG. 22F shows the housing over the inner shaft assembly of FIG. 22D with the wedges extended.

FIG. 23A shows the housing over the inner shaft assembly with the wedges are retracted. FIG. 23B shows the housing over the inner shaft assembly with the wedges extended.

DETAILED DESCRIPTION

Catheters, such as occlusion crossing catheters, including guidewire placement and/or support catheters (which may be referred to as "occlusion crossing catheters" for convenience) may be used to cross an occlusion or lesion. These catheters may be used to place a guidewire within an occluded lumen of a vessel. Any of the catheters described herein may include a guidewire lumen spanning all or most of the length of the device and a rotating and/or oscillating (clockwise and/or counterclockwise relative to the long axis of the catheter) distal tip.

The catheters described herein can be dimensioned to fit within vessels of the body, such as blood vessels. For example, the catheters can be configured to be placed within the peripheral blood vessels. Thus, the catheters can have an outer diameter of less than 0.1 inch, such as less than 0.09 inches, such as less than or equal to 0.08 inches.

In one embodiment, a catheter device includes a distal tip that is rotatable and an onboard imaging system for visualizing the vessel as the device is positioned. In this example, the system includes an OCT imaging system for visualizing the structure and morphology of the vessel walls. The system can see a distance of up to 3 mm, such as up to 2 mm, into the depth of the vessel walls.

In one embodiment, the distal tip of an occlusion-crossing catheter can include one or more dissecting (e.g., cutting) surfaces. The rotatable distal tip region may be used to position a catheter through an occluded lumen of a vessel, including for treatment of chronic total occlusions.

Figure 1:
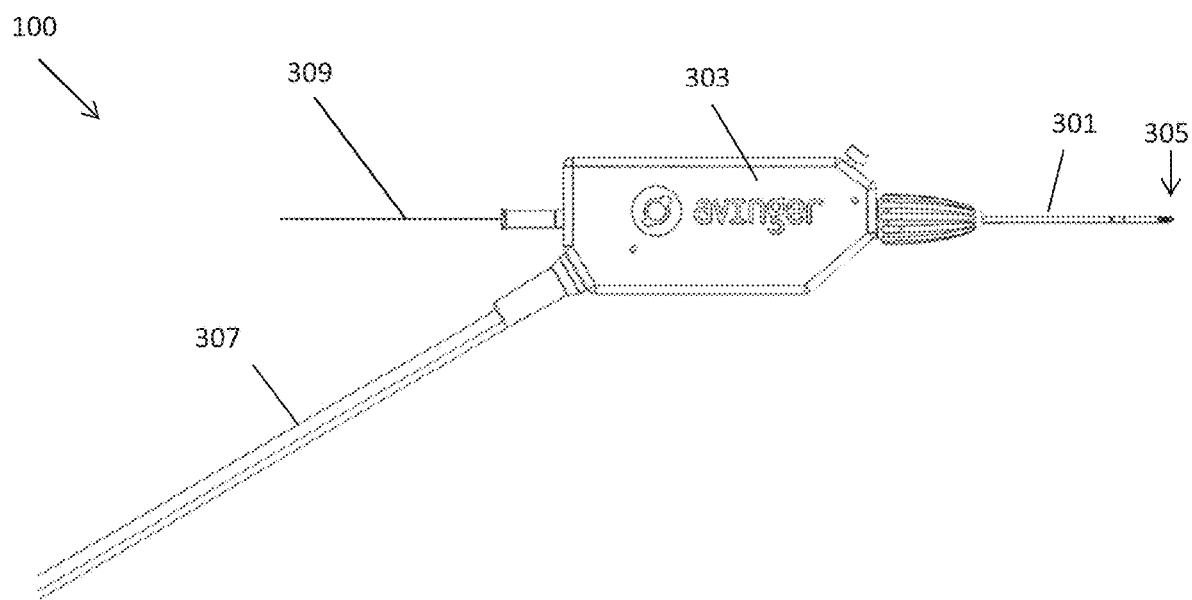
FIG. 1 is a side perspective view of one variation of a catheter device.

Referring to FIG. 1, a catheter (which may be used as a guidewire positioning catheter) 100 includes an elongate flexible shaft 301 and a rotatable distal tip 305 having an imaging sensor, such as an OCT sensor, connected thereto. The shaft 301 extends from a handle region 303 and terminates in the rotatable distal tip 305. The device 100 in FIG. 1 is not necessarily shown to scale, as the length of the shaft has been reduced to show the other features at a more appropriate scale.

A guidewire 309 can extend through the guidewire catheter device 100, such as through a guidewire lumen in the shaft 301. The guidewire 309 may be held resident in the device 100 as it is positioned within a patient or it may be inserted after the distal end of the shaft 301, or at least the distal tip 305, has been positioned within the lumen of the vessel, such as past an occlusion or lesion. The guidewire lumen can be housed inside of a drive shaft (not shown in FIG. 1) configured to rotate the tip 305. Thus, in some variations the drive shaft is a tubular shaft such that the drive shaft may surround the guidewire lumen. In other variations, the drive shaft is a solid shaft which extends through the length of the catheter, and runs alongside (e.g., adjacent to) the guidewire lumen.

The system can include an optical fiber (not shown in FIG. 1) that is fixed at one end to the distal tip 305, but is otherwise free to move around, such as within an internal lumen between a lumen housing the guidewire 309 and an outer casing of the shaft 301. Power and imaging lines 307 ("cabling") may extend from the handle region 303 to connect the optical fiber with a power source and a light source for the OCT system.

The handle region 303 can house the control mechanism for controlling the rotation of the distal tip (and OCT reflector/sensor at the end of the optical fiber). The control mechanism controls the direction of the distal tip as well as the number of revolutions before switching direction. In some embodiments, the handle region 303 can also control the rate of rotation. As discussed further below, the rate of rotation, as well as the number of clockwise and/or counterclockwise rotations, may be optimized to advance the distal end of the device though an otherwise occluded lumen of a vessel while generating a cross sectional image of the lumen, i.e., 360 degrees. The rate and number of rotations may also be optimized to prevent damage to the optical fiber used for the OCT imaging which is attached only at the distal end of the device such that the rest of the fiber can extend along the length of the shaft 301 can wrap, off-axis, around the internal lumen (e.g., guidewire lumen) of the catheter without breaking.

Figure 2A:
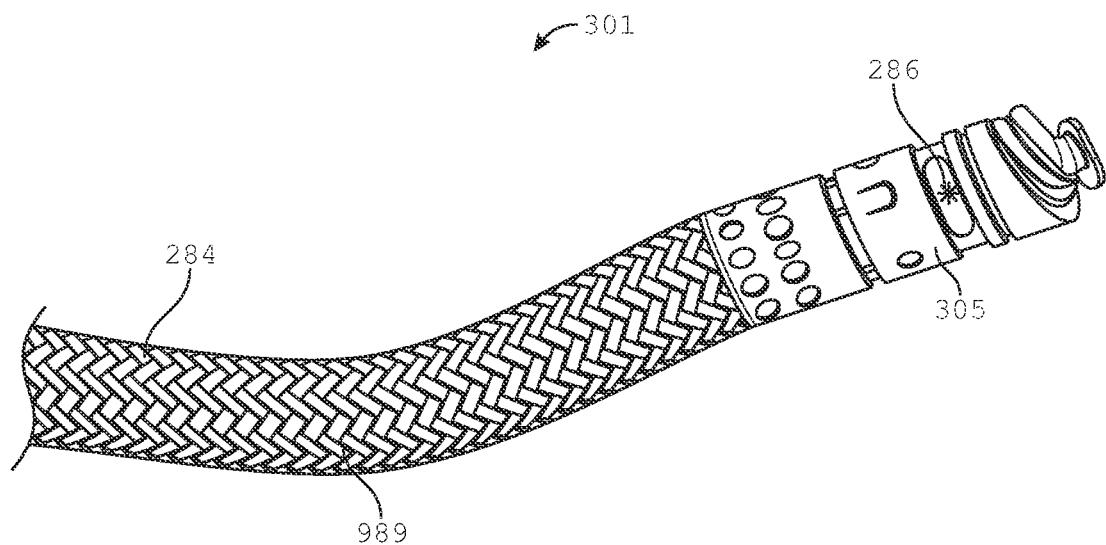
FIG. 2A shows the distal section of an exemplary catheter device.
Figure 2B:
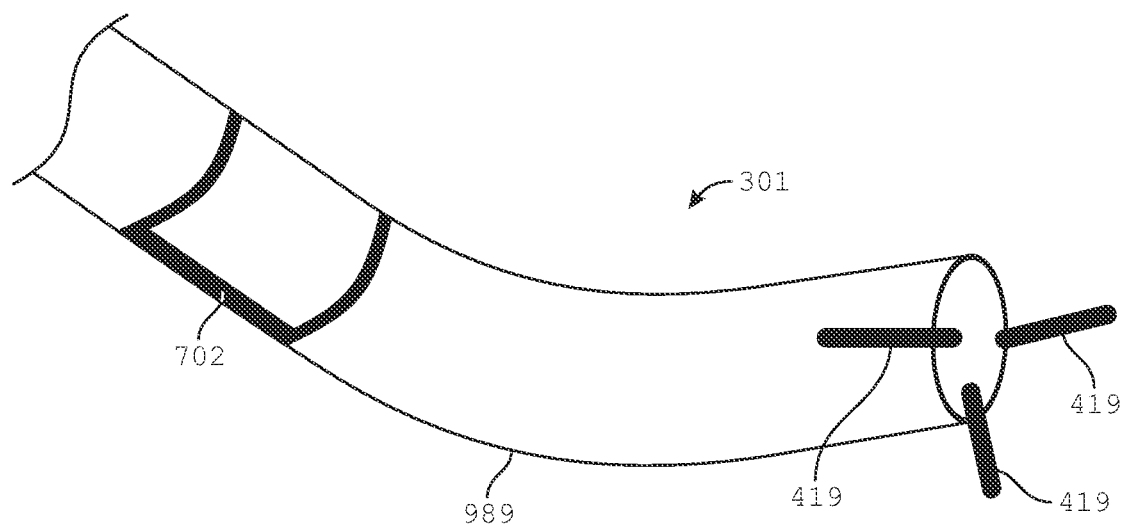
FIG. 2B is a diagram of a distal section of an exemplary catheter device showing the alignment of markers thereon.

Referring to FIGS. 2A and 2B, the shaft 301 can include a fixed jog 989, or a J-shaped bend, near or just proximal to the distal tip 305. The fixed jog 989 can have an angle of 10 to 45 degrees, such as between 20 and 30 degrees. In some embodiments, the jog is shapeable by the user prior to placing the catheter in the body lumen, i.e., the user can fix the jog 989 at the desired angle prior to use. As discussed further below, the fixed jog 989 can aid in steering the shaft 301 to the point of interest.

The shaft 301 can include an outer sheath 284. The outer sheath 284 can include a braided material, such as stainless steel, elgiloy, cobalt-chromium alloys, carbon fiber, or Kevlar. The braided material can improve the stiffness of the catheter to help navigate the catheter through vessel. Further, the shaft 301 can include a guidewire lumen 363 (see FIG. 3B) extending within a drive shaft 421 (see FIGS. 3A-3D) from the proximal end to the distal end of the catheter. The guidewire lumen 363 can end in an opening in a distal tip 305 of the device. The guidewire lumen 363 can thus be configured to pass a guidewire therethrough. Further, the distal tip 305 can include an imaging sensor, such as an OCT sensor 286 configured to capture images within a lumen.

Figure 2C:
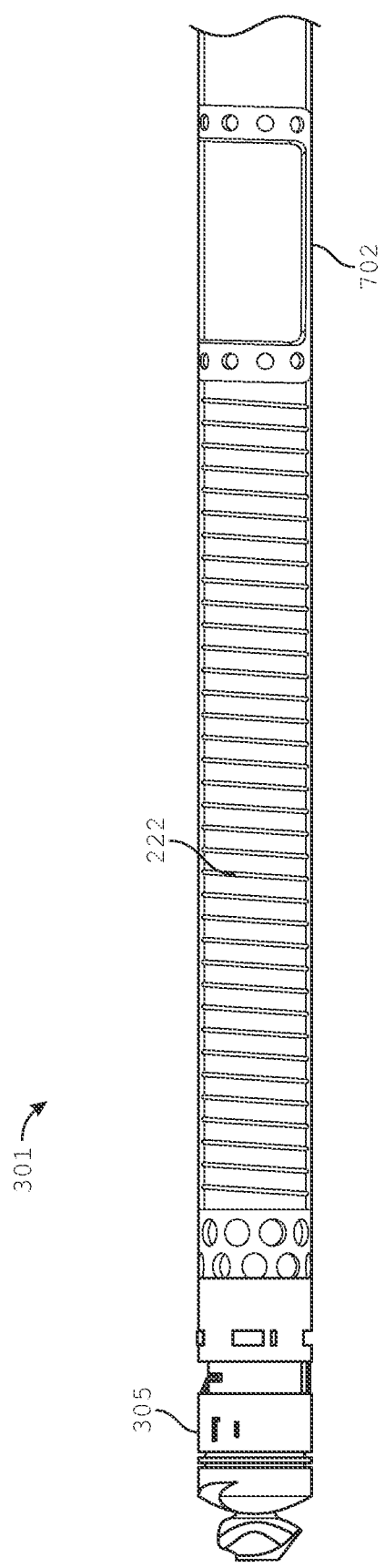
FIG. 2C shows an exemplary coiled reinforcement along the shaft of a catheter device.

Referring to FIG. 2C, in some embodiments, the shaft 301 can have a coiled reinforcement 222 along a portion of its length. The coiled reinforcement 222 can be, for example, a spiral extending around the shaft 301 (as shown in FIG. 2C). The spiral can advantageously reduce kinking or ovalizing of the shaft profile while still allowing for flexion in all directions. In other embodiments, the coiled reinforcement 222 can be a series of rings connected together with a spine, which allows for flexion that is biased in one direction. In some embodiments, the coiled reinforcement 222 can be made of metal, such as stainless steel.

The coiled reinforcement 222 can be configured such that it provides radial hoop strength while still providing enough flexibility for bending. For example, the pitch of the coil can be adjusted to provide the desired flexibility and strength. While a high pitch can advantageously provide flexibility, a low pitch can provide more hoop strength and prevent kink points. In some embodiments, the pitch can be approximately 0.005" to 0.050." In an exemplary embodiment, the pitch is 0.010" for a shaft having an outer diameter of 0.070" to 0.080." Further, the thickness of the coil (in the radial direction) can be adjusted to provide the desired flexibility and strength. While a higher thickness can provide more hoop strength, a lower thickness will provide more flexibility and will keep the outer diameter of the shaft low. In some embodiments, the thickness can be approximately.

The coiled reinforcement 222 can be located at the distal end of the shaft 301, such as between the distal tip 305 and the fluoroscopy marker 702 (described further below). The coiled reinforcement 222 can advantageously provide radial hoop strength to the distal end of the shaft 301 where bending is more likely to occur. Further, in some embodiments, the coiled reinforcement 222 can be aligned with a bending point or fixed jog in the catheter, such as the fixed jog 989 described above. Having the coiled reinforcement 222 in line with these bending points can advantageously help avoiding kinking at the bending point. Moreover, the coiled reinforcement 222 can help maintain the circular cross-section of the shaft 301, thereby providing clearance between the fiber and the inner diameter of the shaft 301 even as radial stresses are applied to the shaft 301 as it travels through tortuous anatomy.

In some embodiments, the coiled reinforcement 222 can be part of the outer sheath 284. In such embodiments, the coiled reinforcement can be placed over the braided material. The coiled reinforcement 222 can then be laminated under a polymer layer, such as polyether block amide (Pebax®). The flexibility and stiffness of the shaft can be optimized based on the durometer or hardness of the polymer layer. For example, the durometer can be between 30 and 40D. In exemplary embodiments, 35D or 40D Pebax is used as the outer layer, which is soft enough for trackability but can hold the bend of a heat-set fixed bend at the end of the device. In some embodiments, a lubricious and flexible liner, such as PTFE, can be placed between the coiled reinforcement 222 and the braid to allow relative movement between the two.

In some embodiments, the coiled reinforcement 222 can be used to hold any preset curvature in the device (such as the jog 989). For example, where the coiled reinforcement 222 includes a series of rings connected together by a spine, the rings can maintain the round cross-section while the spine can hold any preset curvature in the device. In embodiments where the coiled reinforcement 222 is a spiral, the reinforcement 222 can still be used to hold any preset curvature by designing the reinforcement 222 to include a shape-set material, such as nitinol. Further, in either embodiment, the deflection of the coiled reinforcement 222 can be reinforced by using various durometers of polymer laminate. For example, on the inner radius or inside strip of the curve, a higher durometer material may be used while a lower durometer material can be used on the outside of the curve.

The coiled reinforcement 222 can be closed end (i.e., full loop at the ends) or open ended. Using a closed end can advantageously help attach the coiled reinforcement 222 to the shaft by providing more surface area to weld or solder adjacent components thereto.

In some embodiments, part or all of the coiled reinforcement 222 can be used as a radiopaque marker band to indicate the directionality of the shaft 301.

Referring to FIGS. 3A-3D, one variation of the distal end of the shaft 301 can have a distal tip 305 that is roughly corkscrew or helically shaped. The distal tip 305 can thus include spiral flutes, such as two spiral flutes. In this variation, the distal tip 305 rotates and does not extend or retract into a housing, i.e. remains exposed from the shaft 301. The distal tip 305 can be attached to a drive shaft 421 that rotates within the outer sheath 284 and can be configured to rotate in both the clockwise and counterclockwise directions. Further, the distal tip 305 can include a substantially smooth, curved outer surface 322 that presents an atraumatic tissue-contacting surface when rotated in one direction, i.e., the counterclockwise direction in FIGS. 3A-3D, and that further presents a sharp, tissue-cutting surface or edge 403 when rotated in the opposite direction, i.e. the clockwise direction in FIGS. 3A-3D.

At least a portion of the tip 305, such as the proximal portion of the tip 305, i.e., the proximal portion of the cutting geometry, can have a diameter that is substantially equal to or greater than the diameter of the shaft 301. That is, the cutting edge 403 can be helical such that at the distal end, the diameter of the cutting geometry is reduced to the size of the guidewire lumen and gradually increases to the approximate outer diameter of the shaft 301 as it moves proximally. Further, the tip 305 can be configured such that it cuts only in the forward direction and not substantially in the lateral direction. That is, the cutting edge 403 can be substantially forward-facing. Additional tip designs are discussed further below.

An OCT imaging sensor 286 (including the distal end of the optical fiber 411 and the mirror 412) can be fixed to the rotatable distal tip 305 and rotate with it. The distal end of the optical fiber 411 can be secured in a notch 344 formed in the rotatable distal tip 305. An epoxy or other securing material that has a refractive index appropriately mismatched with the end of the optical fiber 411 can hold the end of the optical fiber 411 in the notch 344, as described in U.S. patent application Ser. No. 12/790,703, titled "OPTICAL COHERENCE TOMOGRAPHY FOR BIOLOGICAL IMAGING," filed May 28, 2010, Publication No. US-2010-0305452-A1, the entirety of which is incorporated by reference herein. The imaging sensor 286 can direct the optical beam for OCT imaging from the distal tip 305 of the catheter into the tissue. In one embodiment, the imaging system is oriented so that the mirror 412 directs the optical beam approximately or substantially perpendicular to the catheter axis. In some variations, this angle is different or is adjustable. For example, the orientation of the mirror 412 may be changed (including adjusted by the user) to change the direction of imaging and/or image more distally or proximally. As used here, substantially perpendicular may include plus or minus 10 degrees, plus or minus 5 degrees, or plus or minus 2 degrees, off of the 90 degree angle that is perpendicular from the elongate axis of the distal tip and/or catheter body.

The sensor 286 can be located close the distal end of the tip 305, such as just proximal to the cutting edge 403. For example, the sensor 286 can be located within 5 mm of the distal end of the tip 305, such as less than 3 mm, such as approximately 2 mm. Advantageously, by minimizing the distance between the sensor 286 and the distal end of the tip 305, the resulting image will be a closer approximation of the exact tissue or material being passed by the distal end. The sensor 286 may be directed laterally (e.g., to image the sides of the vessel in which the catheter is traveling), or angled forward or backward. The sensor 286 can be located off of the central axis of the shaft 301 and close to the outer diameter of the tip 305, such as within 0.05 inches, e.g. less than 0.3 inches, less than 0.02 inches, or less than or substantially equal to 0.01 inches of the outer diameter of the tip 305. Advantageously, by having the sensor 286 close to the outer diameter, the depth that the OCT system can see into the tissue will be greater, i.e., the amount of tissue lying within the OCT imaging range is increased.

As shown in FIGS. 3A-3E, the rotating tip 305 is held in a chassis 405 that is fixed relative to the shaft 301, i.e., that does not rotate with the rotating tip 305. The chassis 405 is any structure within which the distal tip 305 can rotate and which secures the drive shaft 421 and/or the distal tip 305 to the end of the shaft 301; it may also be referred to as a housing. The outer sheath 284 can be connected to the chassis 405 such that the outer sheath also remains stationary while the distal tip 305 rotates.

Figure 3A:
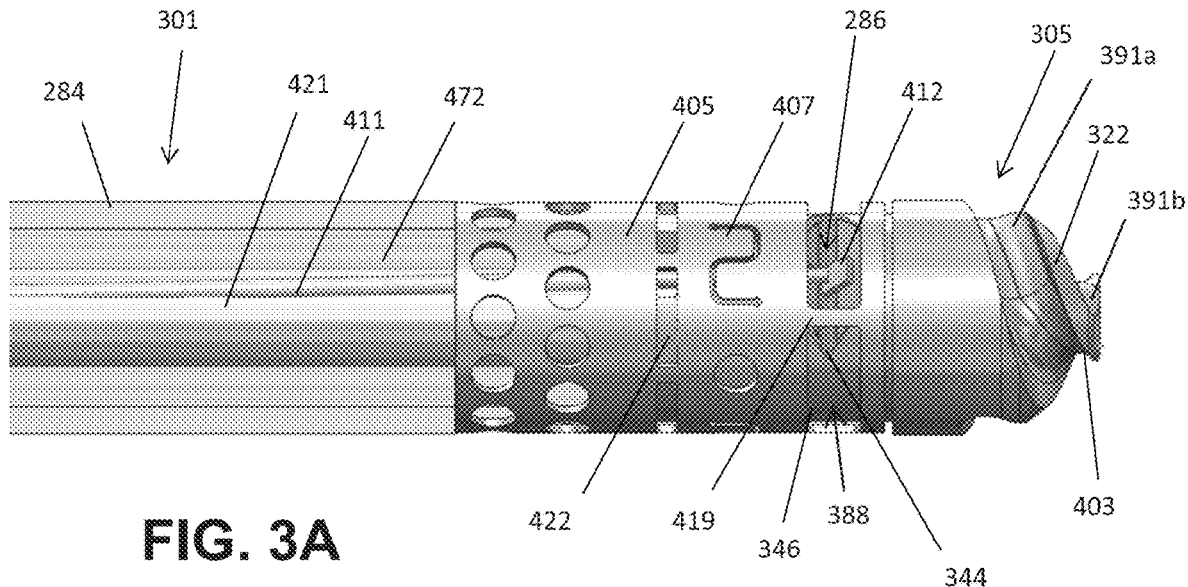
FIGS. 3A-3B show various side perspective views of the distal end an exemplary catheter device.
Figure 3B:
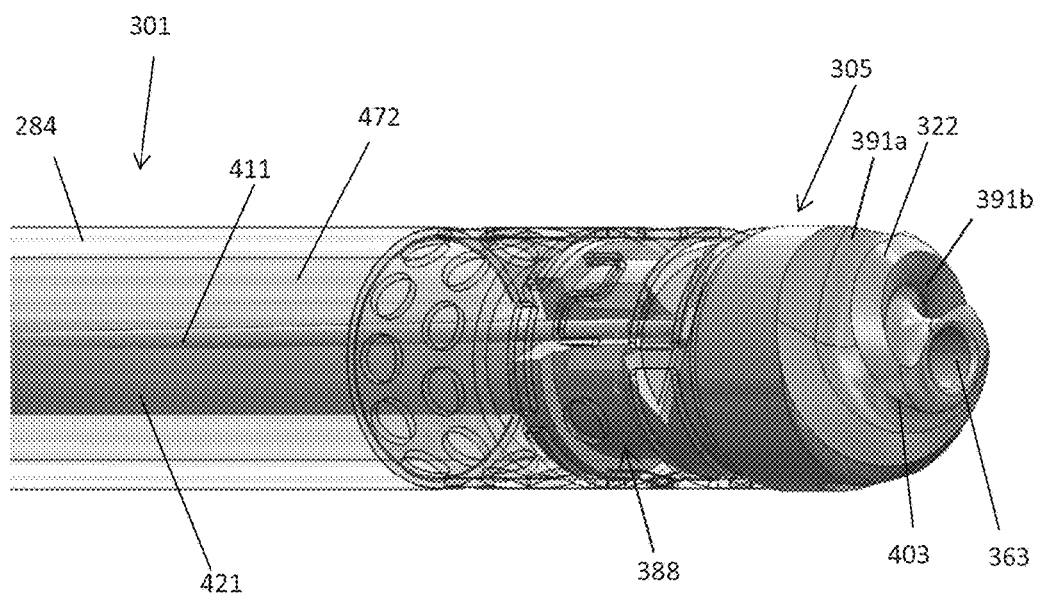

The chassis 405 can have one or more "window" regions through which the OCT imaging sensor 286 can view the tissue. For example, as shown in FIGS. 3A and 3B, the chassis 405 can include three window regions 346 separated by spines 419 (which may be referred to as posts, struts, dividers, separators, etc.) arranged annularly around the chassis 405. These spines 419 may serve as reference markers as the imaging sensor 286 rotates, as discussed below. The spines 419 may be separated from one another by different distances. For example, one of the windows may be larger than the other two, or smaller than the other two. This asymmetric sizing may provide a visual reference on the display of the OCT imaging.

Thus, in one example, there are three spines 419 arranged such that there is a 90° window between the first and second spine, a 90° degree window between the second and third spine, and a 180° degree window between the first and third spine. The spines 419 can have a predetermined and fixed location relative to the jog 989 in the catheter. For example, one of the spines 419 can be aligned relative to the jog 989. In one embodiment, shown in FIG. 2B, the second spine 419 is aligned opposite to the jog 989, i.e., such that the catheter points away from the second spine 419 (the inner curved portion of the jog 989 is opposite to the second spine 419 and the outer curved portion of the jog 989 is axially aligned with the second spine 419). This alignment can be used to help orient the device in a specific direction with respect to the image and/or vessel, as discussed further below. In some embodiments (as shown in FIGS. 3A-3E), the spines 419 can all have the same shape as one another. In other embodiments, the middle spine can have a different shape so as to provide further visual indication as to the orientation of the device.

For example, as shown in FIGS. 20A-20C, a chassis 2005 (which can be used in place of chassis 305 or 405) can include spines 2019a,b,c arranged such that there is 90° between spine 2019a and 2019b, 90° between spine 2019b and 2019c, and 180° between 2019c and 1019a. The middle spine 2019b, however, can have a different shape than the spines 2019a,c. As shown in FIGS. 20A-20C, for example, the middle spine 2019b can be thicker and/or include a slot 2022 therein. As described further below, this difference in shape can make it easier for the user to visualize the middle marker (which can be aligned, for example, such that the inner curved portion of the jog 989 is opposite to the marker 2019b).

Figure 3C:
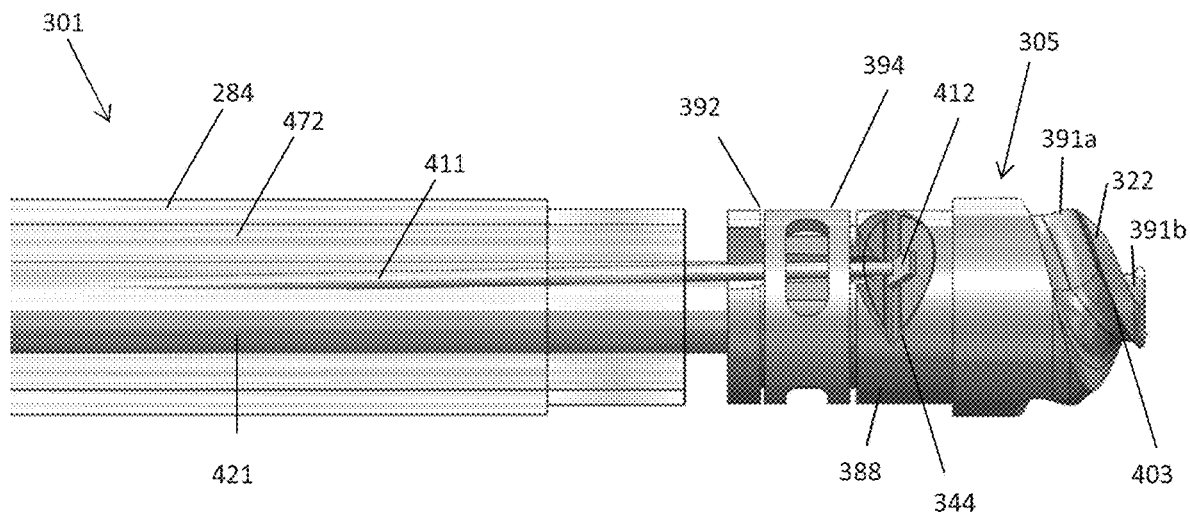
FIG. 3C shows the distal end of the device of FIGS. 3A-3B, but with the collar removed.
Figure 3D:
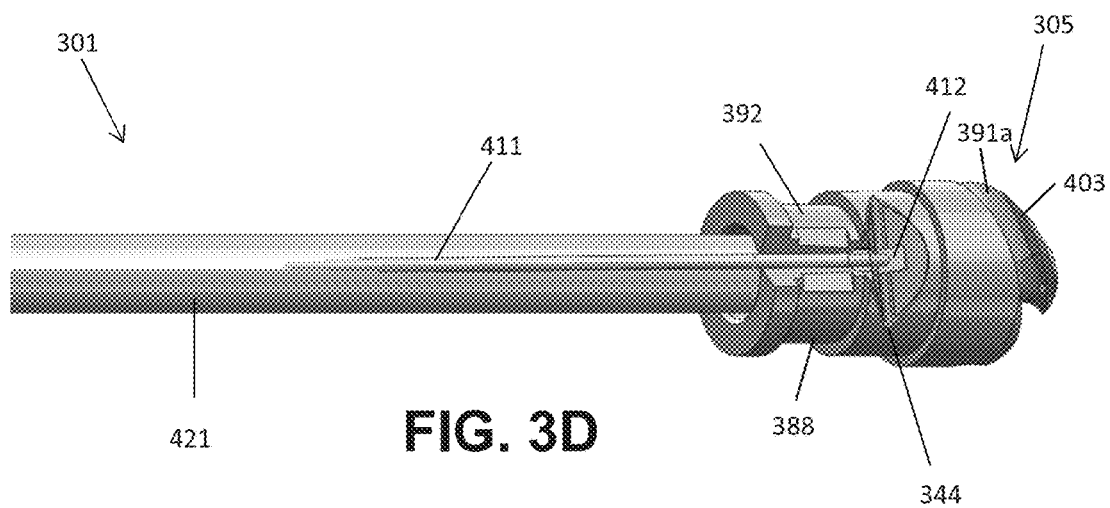
FIG. 3D shows the distal end of the device of FIGS. 3A-3C, but with the collar and outer sheath removed.

As shown in FIGS. 3C-D, the distal tip 305 can include a groove 392 at the proximal end to engage a bushing 394 (e.g., annular ring). The bushing 394 can remain fixed with respect to the shaft 301 and may provide a lubricious surface to eliminate or reduce friction and fix the longitudinal position of the distal tip 305. The bushing 394 may be made of PEEK or other hard lubricous material. In some embodiment, the groove 392 may be crimped or clamped to the stationary chassis 405, thereby allowing the rotatable distal tip 305 to have improved stability during rotation.

Figure 3E:
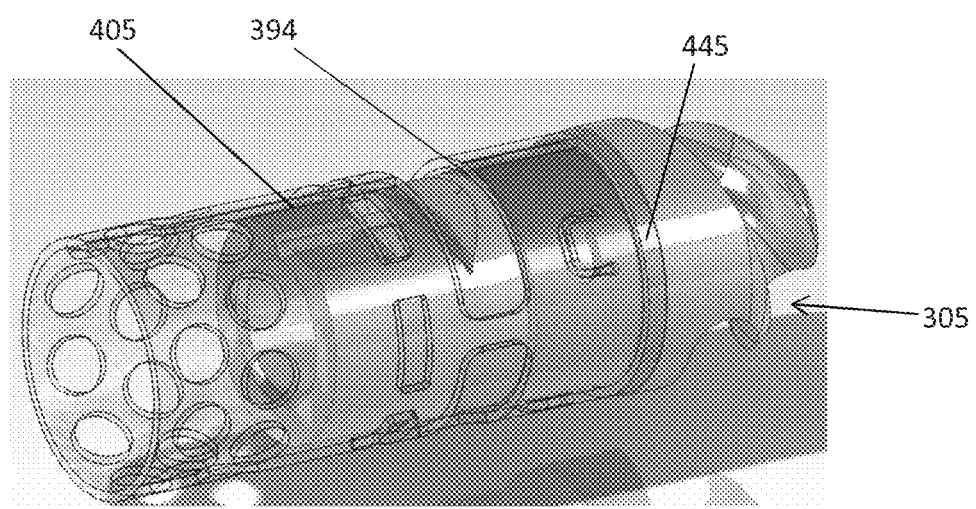
FIG. 3E shows an embodiment of the distal end of an exemplary catheter device wherein the bushing includes a shoulder.

Referring to FIG. 3E, in another embodiment, the bushing 394 includes a shoulder 445. The shoulder 445 can extend outward into the space between the distal edge of the chassis 405 and the distal tip 305. The shoulder 445 can be made of the same lubricous material as the rest of the bushing 394. The shoulder 445 prevents the distal edge of the chassis 405 from rubbing against the tip 305 and further reduces the friction of the system.

As shown in FIG. 3A, the chassis 405 may engage the groove 392 of the distal tip 305 directly, such as by one or more tabs 407 or locks that can be pushed in when the distal tip 905 is held within the chassis 405 to lock the bushing ring 394 and distal tip 305 in position. The chassis 405 or distal tip 305 can be made from a lubricious material.

Referring to FIGS. 3A-B, the chassis 405 can include one or more openings or ports 422 out of which a clearing fluid, such as saline or water, may be driven to help clear the pathway for imaging the walls of the vessel lumen as the device is operated. Blood, including red blood cells and other blood components, may degrade the ability of the OCT imaging system from imaging other tissues because OCT may not readily "see" through blood. Thus, the catheter may be configured to clear the blood from the region of interest, i.e., the region where the optical beam is emitted from the catheter for OCT imaging. The ports 422 can thus be configured to emit a clearing fluid from the catheter to clear blood from the imaging sensor. Thus, in this variation the port 422 is located directly adjacent to the imaging sensor and emits fluid to clear blood from the region where the optical beam is being emitted. The ports 422 can be less than 2 mm from the imaging sensor, such as less than 1.5 mm. Advantageously, by having the ports 422 close to the imaging sensor, the pressure and amount of clearing fluid required to clear the blood from the region of interest can be low. For example, less than 1 ml, such as less than 0.5 ml, e.g., less than 0.2 ml of clearing fluid can be required to clear the blood from the region of interest. Thus, the required pressure may be nominal and the flow of saline or other clearing fluid may be minimal and still effectively clear blood from the imaging space, greatly improving the resolution of the vessel walls and increasing the depth of penetration. Further, using small amounts of clearing fluid can advantageously avoid problems associated with having too much fluid in a small space, such as separation of tissue (e.g., dissection).

The shaft 301 can be configured such that the clearing fluid enters at the proximal end of the catheter and is transported to the distal end by flowing in a space 472 between the outer sheath 284 and the drive shaft 421. The clearing fluid may be pressurized from the proximal end (e.g., using a syringe, etc.) so that it is pushed out of the opening 422 to clear blood from the OCT pathway.

Figure 4:
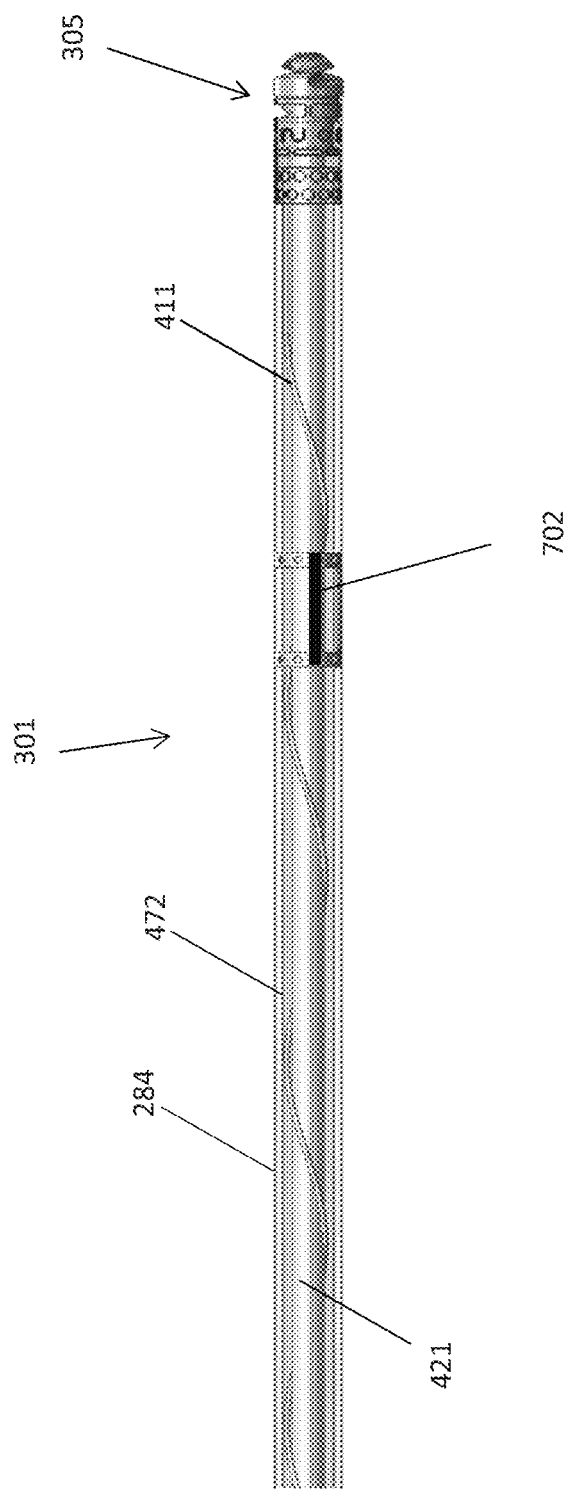
FIG. 4 shows an optical fiber wrapped around a drive shaft of an exemplary catheter device.

Referring to FIG. 4, the OCT portion of the catheter device 100 may be referred to as an off-axis imaging system because the management of the OCT optical fiber 411 is arranged asymmetrically, off-axis with reference to the long axis of the catheter. The fiber 411 can be configured to extend freely within the shaft 301 in the space 472 between the drive shaft 421 and the outer sheath 284 except where it is attached at the distal end of the device, e.g., at the rotatable distal tip 305. Accordingly, as shown in FIG. 4, when the drive shaft 421 is rotated to rotate the distal tip 305, the fiber 411 can wrap around the drive shaft 421. This arrangement can advantageously enhance the flexibility, i.e., allow for movement of the catheter without fracturing the optical fiber 411.

Because the optical fiber 411 winds and unwinds around the drive shaft 421 as it is rotated with the distal tip 305, both the rate of rotation and the number of rotations may be controlled to optimize performance, prevent the fiber 411 from binding within the shaft 301, and prevent the fiber 411 from snapping due to excessive twisting or rotation. For example, the distal tip 305 may be configured to alternate its rotation from clockwise to counter clockwise. Thus, the drive shaft 421 can be configured to rotate (with the distal tip 305) clockwise for a fixed number of rotations and to rotate counterclockwise for the same number of rotation before switching back to clockwise rotations and repeating the process. The number of rotations in the clockwise direction can be substantially equivalent to the number of counter clockwise rotations in order to relieve any residual twisting. Advantageously, by having a substantially equivalent number of rotations in the clockwise and counterclockwise directions, accumulation of fiber twisting can be avoided, thereby avoiding snapping of the fiber due to such accumulated twisting. In general, the device is configured to rotate the distal tip n rotations clockwise and n rotations counterclockwise, switching between clockwise and counterclockwise rotational direction after each n rotations. The number of rotations n can be any number, including fractional, typically between 1 and 100; preferably it is between 1 and 10, depending on the length of the catheter and the amount of stress the fiber can withstand. For example, the device may be configured to rotate approximately 6, 8.5, 10, 12.7, 15, etc. times clockwise, then counterclockwise the same number of rotations. Thus, the device is configured so that it doesn't continuously spin clockwise or counterclockwise, but has a limited number of rotations in either direction (e.g., less than 25 rotations, such as 10 rotations), after which it automatically switches to rotate the other direction. The transition between clockwise and counterclockwise rotation may be performed automatically, which is described in more detail with reference to FIGS. 5A-5E, below.

The rotation may be driven by a motor or other driver (e.g., within the handle) or it may be manual. Preferably, the rotation is automatic, and is driven at a constant speed that is typically between about 1 and 300 revolutions per minute (rpm); for example, the rotation rate may be about 10 rpm, 20 rpm, 30 rpm, 40 rpm, 50 rpm, 60 rpm, etc. In some variations, the distal tip is rotated between about 1 and about 100 rpm, e.g., between about 1 and 80 rpm, such as between about 30 and 60 rpm. The rate and the consistency of rotation may be optimized for penetration through the occlusion within the vessel, for image stability, and also to produce relatively streak-free imaging using the OCT. Thus, the rate of rotation may be limited to an upper limit speed that is held relatively constant. In addition, the rate of rotation may be sufficiently low (e.g., less than 150 or 100 or 50 rpm) so that the distal head rotates but does not 'drill' through the tissue, including one or more occlusions. In some embodiments, the user can control the rate of rotation, such as by setting the motor to rotate at a particular speed.

Referring to FIG. 5A-5E, the handle 303 of the device can be configured to control rotation and advancement of the shaft 301. The handle 303 can include a switch 562 configured to turn the system on or off (i.e. to start the rotation of the distal tip and/or the imaging system). The handle can be covered by a housing 501 which may be configured to conform to a hand or may be configured to lock into a holder (e.g., for connection to a positioning arm, a bed or gurney, etc.). Within the handle 303, a drive system, including a motor 503 and drive gears 515, 516, 517, may drive the drive shaft 421 to rotate the distal tip 305 of the device and/or the OCT imaging system relative to the shaft 301. In some variations, the drive system is controlled or regulated by a toggling/directional control subsystem for switching the direction of rotation of the drive shaft between the clockwise and counterclockwise direction for a predetermined number of rotations (e.g., 10).

In FIGS. 5A-5E, a mechanical directional control can be configured to switch the direction of rotation between clockwise and counterclockwise when the predetermined number of rotations have been completed. In this example, the directional control includes a threaded track (or screw) 511 which rotates to drive a nut 513 in linear motion; rotation of the threaded track by the motor 503 results in linear motion of the nut along the rotating (but longitudinally fixed) threaded track 511. As the motor 503 powers the drive shaft 421 in a first rotational direction (e.g., clockwise), the nut 513 moves linearly in a first linear direction (e.g., forward) until it hits one arm of a U-shaped toggle switch 516, driving the U-shaped toggle switch in the first linear direction and flipping a switch 523 (visible in FIG. 5D) to change the direction of the motor 503 to a second rotational direction (e.g., counterclockwise), and causing the nut to move linearly in a second linear direction (e.g., backward) until it hits the opposite side of the U-shape toggle switch 516, triggering the switch to again change the direction of rotation back to the first rotational direction (e.g., clockwise). This process may be repeated continuously as the motor is rotated. The motor 503 may be configured to rotate the drive shaft 421 in either direction at a constant speed. The system may also include additional elements (e.g., signal conditioners, electrical control elements, etc.) to regulate the motor as it switches direction.

The number of threads and/or length of the threaded track (screw) 511 may determine the number of rotations that are made by the system between changes in rotational direction. For example, the number of rotations may be adjusted by changing the width of the U-shaped toggle 514 (e.g., the spacing between the arms). Lengthening the arms (or increasing the pitch of the screw) would increase the number of rotational turns between changes in direction (n). The toggle may therefore slide from side-to-side in order to switch the direction of the motor. The length of the nut 513 can also determine the number of rotations that are made by the system between changes in rotational direction, i.e., the longer the nut, the fewer the number of rotations before switching direction.

In some variations, the motor 503 is rotated in a constant direction, and the switch between clockwise and counterclockwise is achieved by switching between gearing systems, engaging and disengaging an additional gear, or using gears that mechanically change the direction that the drive shaft is driven.

In the exemplary device shown in FIGS. 5A to 5E, the drive system includes the motor and three gears that engage each other to drive the drive shaft in rotation. For example, the motor 503 rotates a first gear 517, which is engaged with a second gear 516 (shown in this example as a 1:1 gearing, although any other gear ratio may be used, as appropriate). A third gear 515 engages with the second gear 516. The third gear may drive or regulate an encoder 507 for encoding the rotational motion. This encoded information may in turn be used by the drive system, providing feedback to the drive system, or may be provided to the imaging system.

Figure 5A:
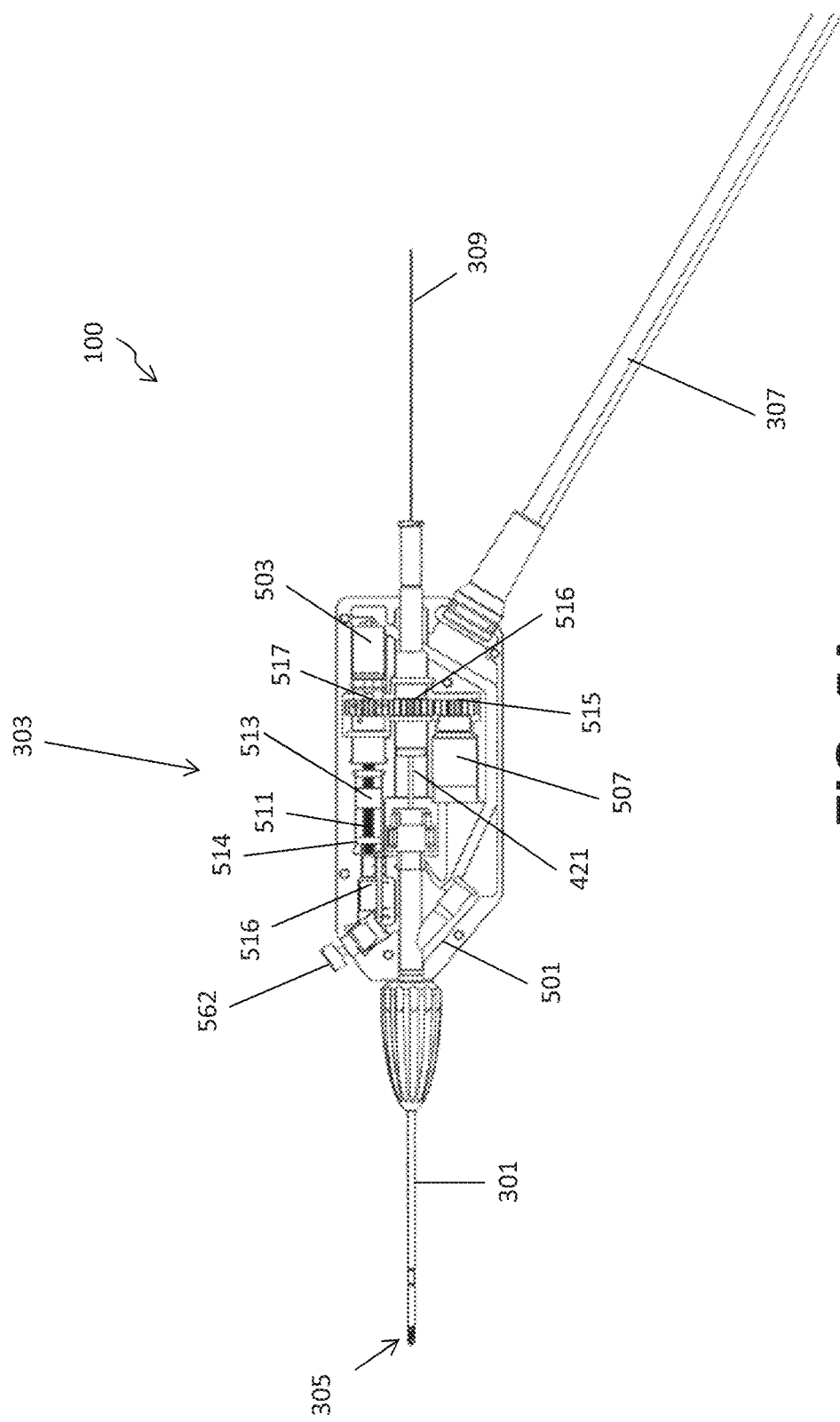
FIGS. 5A-5E show a handle assembly or partial handle assembly for an exemplary catheter device.
Figure 5B:
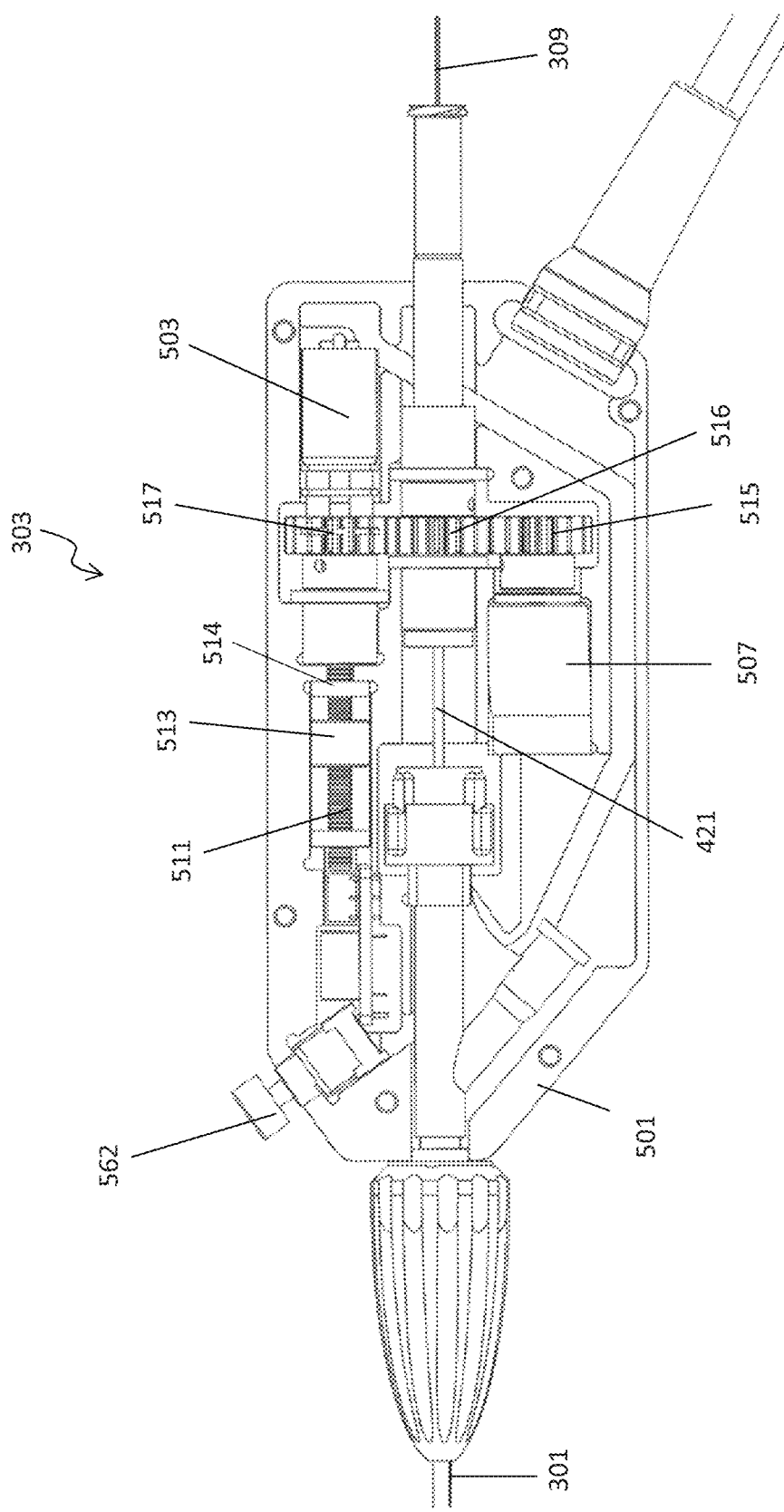
Figure 5C:
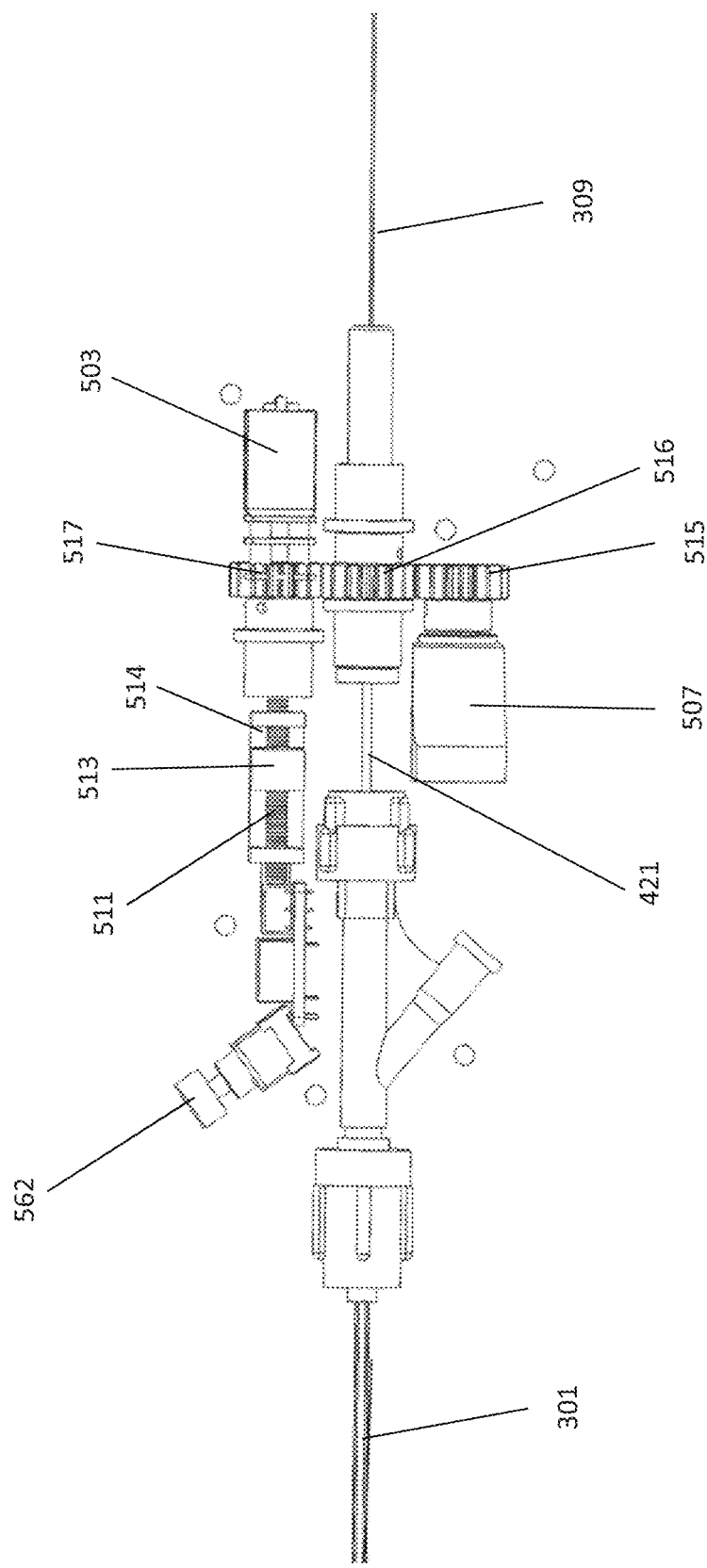
Figure 5D:
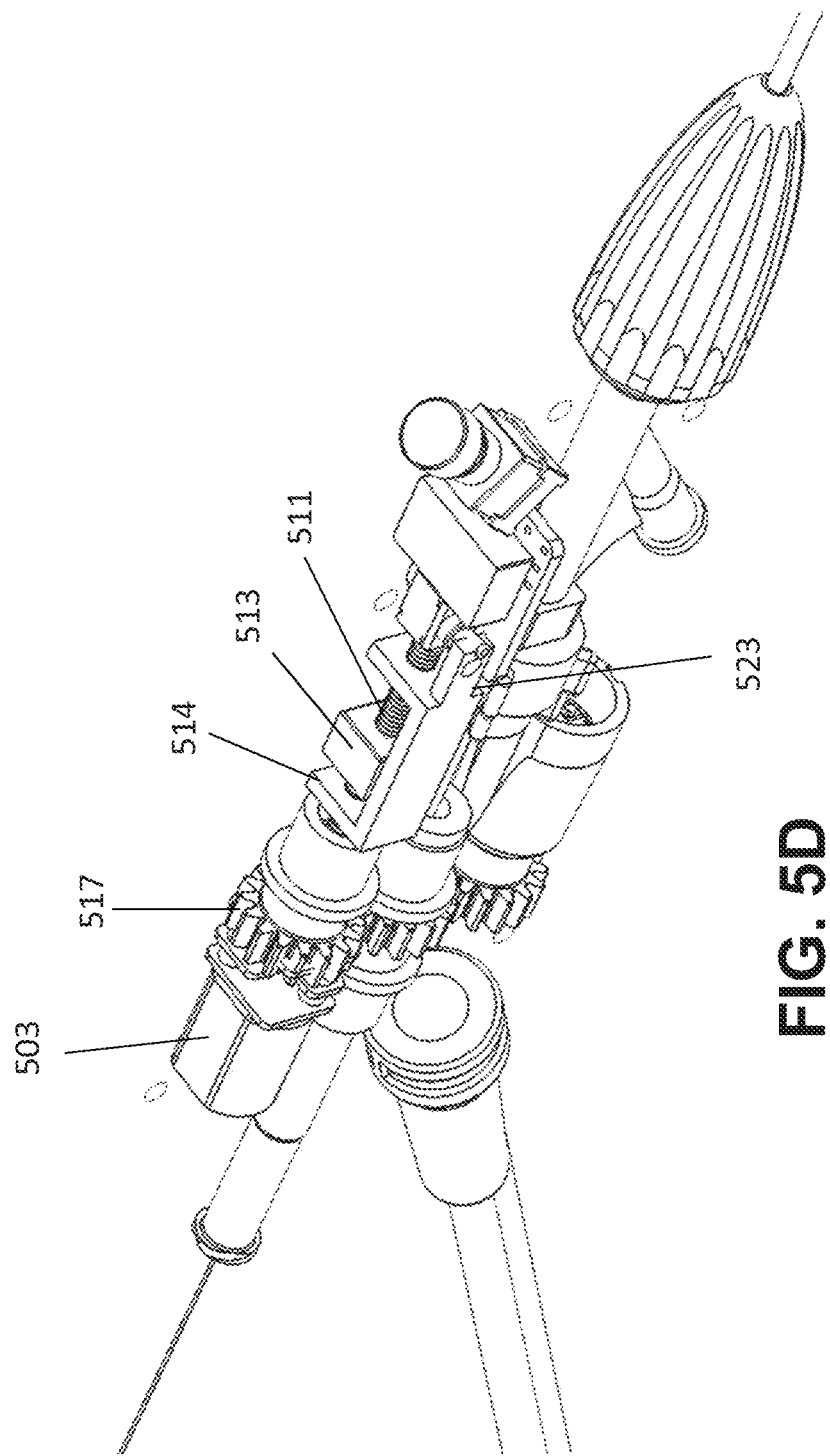
Figure 5E:
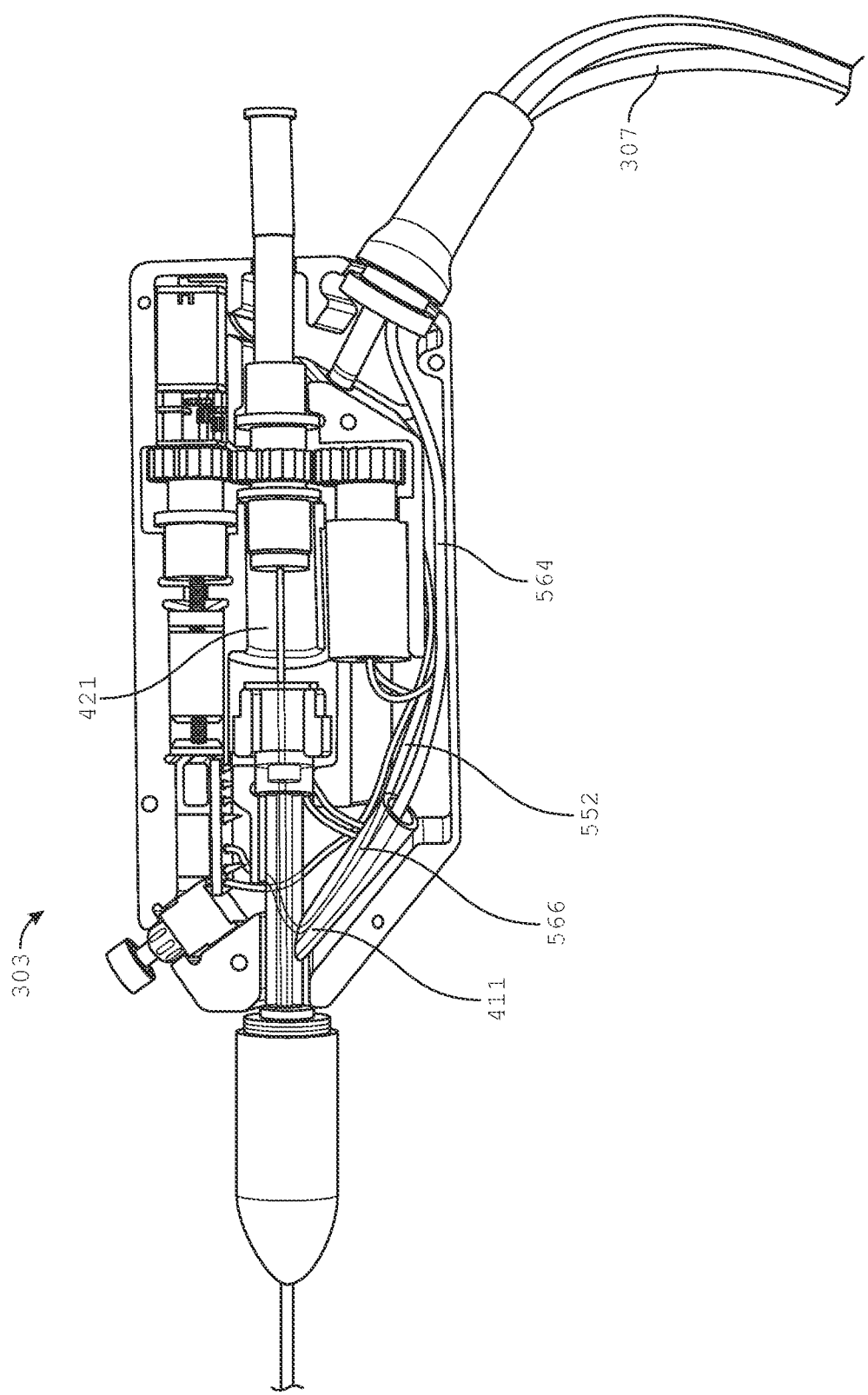

Referring to FIG. 5E, the cabling 307 can include both a fluid flush line 552 configured to be attached to a fluid source and an optical fiber 411 configured to be connected to the OCT system. The flush line 552 and the fiber 411 can both run through the handle 303. The fiber 411 and the flush line 552 can be bonded at a bonding point 566 in the handle 303, creating a seal to prevent fluid from leaking into the handle. The flush line 552 can end at the bonding point 566, allowing the fluid to exit the flush line and continue down the shaft 301 in the space 572 between the outer sheath 284 and the drive shaft 421. Further, the fiber 411 can extend through the bonding point 566 and wrap around the drive shaft 421 in the space 572. As shown, because the fiber 411 is configured to wrap around the guidewire lumen, a separate fiber management system is not necessary. In some embodiments, a protective coating 564 can surround the optical fiber until distal of the bonding point 566.

Figure 6:
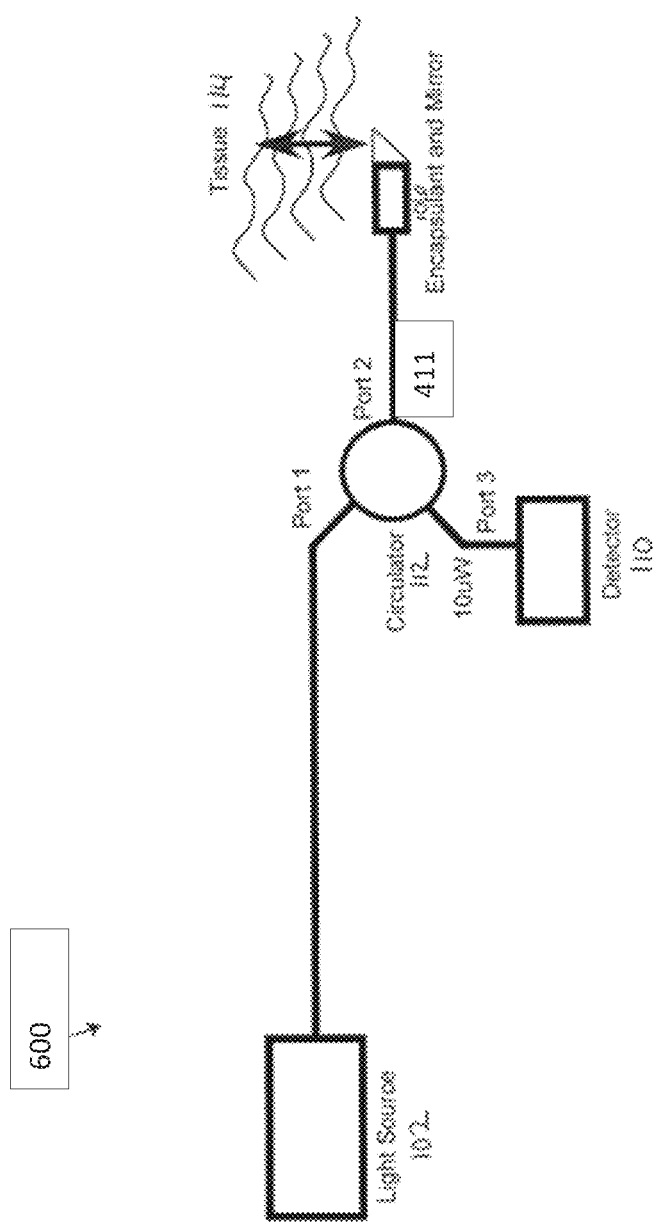
FIG. 6 shows an exemplary OCT system.

Referring to FIG. 6, the fiber 411 can be connected at the proximal end to a common-path OCT system 600. The common-path OCT system 600 includes a light source 102, such as a swept frequency laser. In an alternative arrangement, the light source could be a broadband light source such as a super-luminescent diode (to conduct Time Domain OCT or Spectral Domain OCT using an optical spectrometer). The optical fiber 411 transfers radiation from the light source 102 to the target 114. The optical fiber 411 is in optical contact with an interface medium 106, i.e. the light exiting the optical fiber and entering the interface medium sees only one interface. In some embodiments, as shown in FIG. 6, the end of the optical fiber is embedded in the interface medium 106. The interface medium 106 can be, for example, a glue or epoxy. In the common-path OCT system 600, the index of refraction of the interface medium 106 is different than the index of refraction of the core of the optical fiber 411. This creates a Fresnel reflection, in which part of the light exits the core, and part of the light is reflected back. Some of the light beam that exits the optical fiber 411 will encounter the target 114 and be reflected or scattered by the target 114. Some of this reflected or scattered light will, in turn, reenter the tip of the optical fiber 411 and travel back down the fiber 411 in the opposite direction. A Faraday isolation device 112, such as a Faraday Effect optical circulator, can be used to separate the paths of the outgoing light source signal and the target and reference signals returning from the distal end of the fiber. The reflected or scattered target light and the Fresnel-reflected reference light from the fiber face can travel back to a detector 110 located at the proximal end of the optical fiber 411.

Because the reflected or scattered target light in the OCT system 600 travels a longer distance than the Fresnel reflected reference light, the reflected or scattered target light can be displaced by frequency, phase and or time with respect to the reference beam. For example, if swept-source radiation is used, then the light from the target will be displaced in frequency. The difference in displacement in phase, time or frequency between the reflected or scattered target light and the reference light can be used to derive the path length difference between the end of the optical fiber tip and the light reflecting or light scattering region of the target. In the case of swept source OCT, the displacement is encoded as a beat frequency heterodyned on the carrier reference beam.

The light source 102 can operate at a wavelength within the biological window where both hemoglobin and water do not strongly absorb the light, i.e. between 800 nm and 1.4 μm. For example, the light source 102 can operate at a center wavelength of between about 1300 nm and 1400 nm, such as about 1310 nm to 1340 nm. The optical fiber 411 can be a single mode optical fiber for the ranges of wavelengths provided by the light source 102.

Figure 7A:
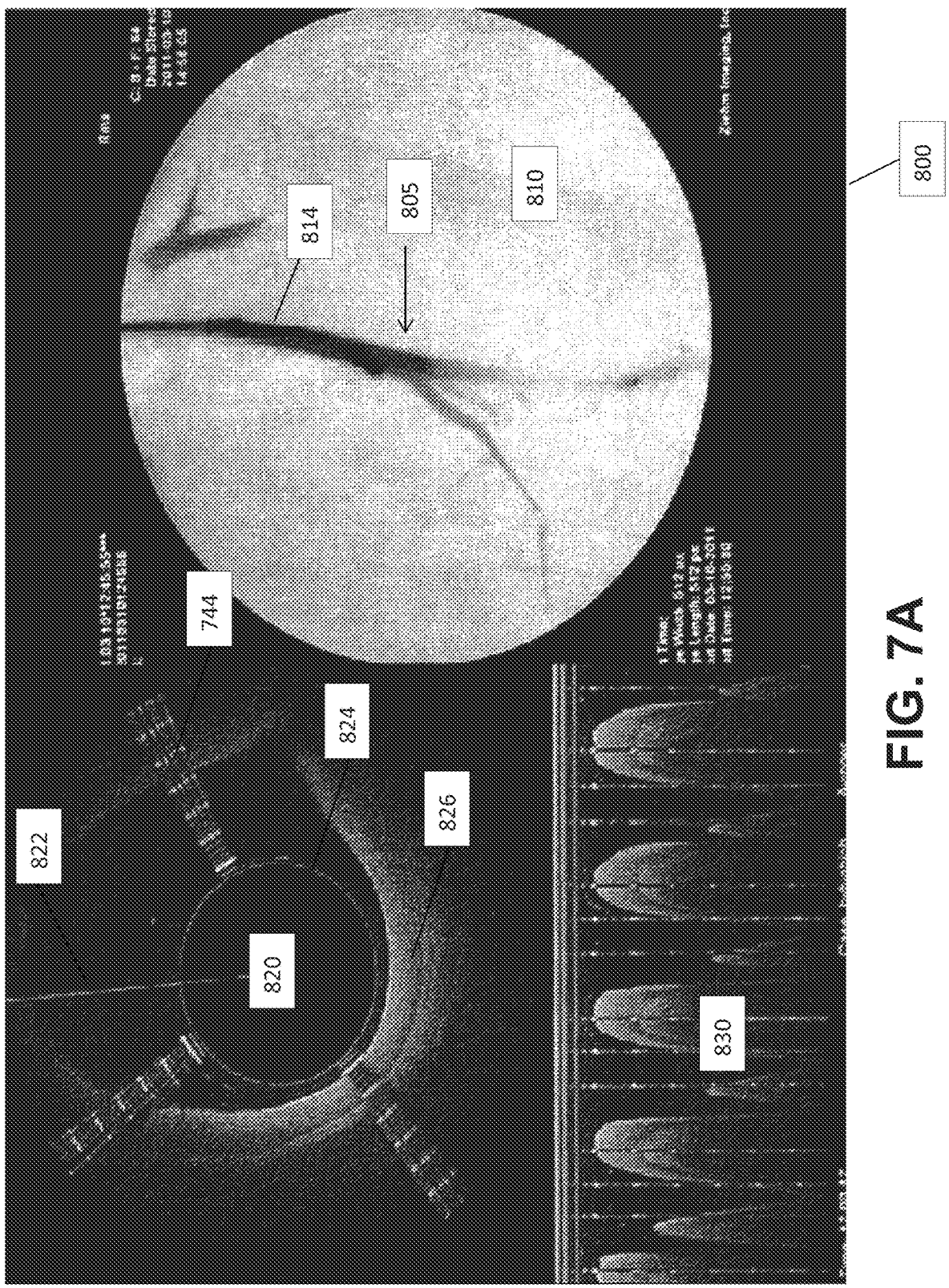
FIGS. 7A and 7B show screen captures of an exemplary catheter device including an OCT imaging system.
Figure 7B:
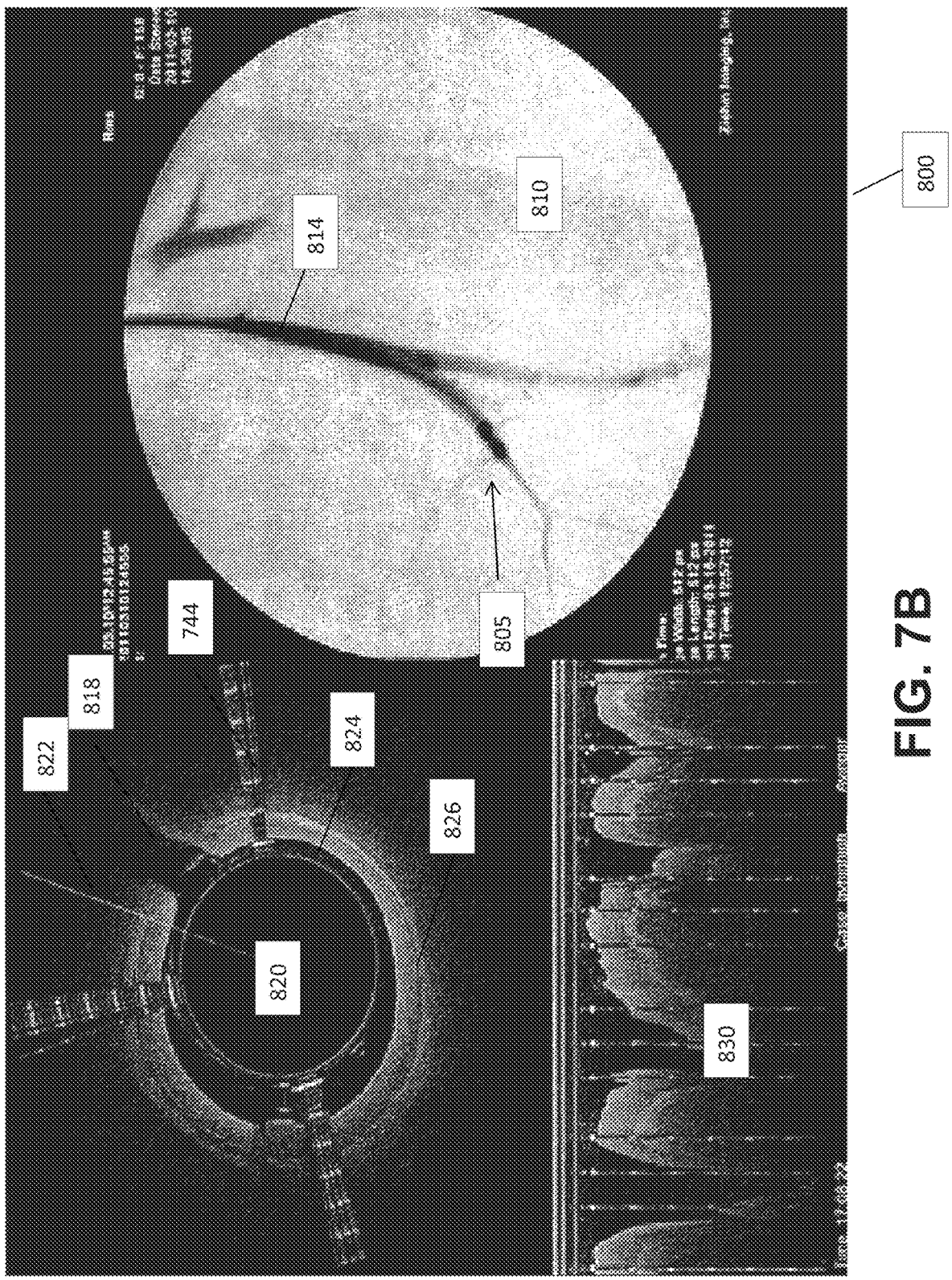

FIGS. 7A and 7B are exemplary screen captures of an imaging output from the system described herein. In FIGS. 7A and 7B, the displayed image 800 is divided into three components. On the right is a fluoroscopic image 810 showing the distal end 805 of the catheter within a vessel 814. Contrast has been inserted into the vessel 814 to show the extent of the vessel 814 and any occluded regions.

On the left is an OCT image 820. To obtain the OCT image 820, the distal tip of the catheter rotates at approximately 30 rpm, and the OCT system provides a continuous set of images as the catheter rotates within the vessel. The images are combined into a continuously updated OCT image 820 that corresponds to the inside of the lumen in which the catheter is inserted. That is, the OCT image 820 is an image trace of the interior of the vessel just proximal to the distal tip as it rotates. The line 822 (extending to almost 12 o'clock in the figure) indicates the current direction of the OCT laser beam as it is rotating. The circle 824 in the middle of the image 820 represents the diameter of the catheter, and thus the area surrounding the circle 824 indicates the vessel. The OCT imaging can extend more than 1 mm from the imaging sensor, such as approximately 2 mm or approximately 3 mm and thus will extend into the walls of the vessel (particularly in the closer region of the vessel) so that the different layers 826 of the vessel may be imaged. In this figure, the three striped rays 744 (extending at approximately 2 o'clock, between 7 and 8 o'clock, and approximately 11 o'clock) indicate the location of the three spines of the catheter and thus may act as directional markers, indicating the orientation of the distal end of the catheter within the body. As described in more detail below, the user may also be able to determine relative orientation of the OCT image (relative to the patient's body orientation) using these striped rays 744.

On the bottom left of the image 800 is a waterfall view 830 of the OCT image as it circles the radius of the body. This waterfall image 830 may be particularly useful in some applications of the system, for example, indicating the relative longitudinal position of a feature (e.g., layered structures, occlusions, branching region, etc.) as the device is moved longitudinally within the vessel. The waterfall view 830 typically includes a time axis (the x-axis) while the y-axis shows the image from the OCT sensor. In addition, the waterfall view 830 may provide an indication of when the catheter has crossed an occlusion. For example, the waterfall view 830 may show the patient's heartbeat when the walls of the vessel move relative to the heartbeat. In these cases, the waterfall view 830 may show the walls of the vessel moving with the heartbeat. In contrast, when the distal tip is within an occlusion the wall of the vessel, the waterfall view will not show movement of the walls since the occlusion material typically prevents the movement of the walls due to the heartbeat, while in healthy vessels the heartbeat is apparent. Thus it may be possible to determine when the catheter has crossed the occlusion based on the waterfall view 830. In some variations, this effect may be automated to provide an indication of when the device is within or has crossed an occlusion. In general, crossing the boundary of a total occlusion is not well defined and may result in inadvertently dissecting the vessel. When the catheter is within the true lumen, the vessel wall may move; if the catheter tip is not in the true lumen all or part of the vessel wall will not move. Thus, this movement of the wall during heartbeat may reflect the position within the true versus false lumen.

FIG. 7B shows another screen capture from the same procedure shown in FIG. 7A. As shown in the fluoroscopy image 810, the distal tip 305 is further within the vessel 814 than in FIG. 7B. In this example, the OCT image 820 shows a branch 818 of the vessel extending from the vessel in the 2 o'clock position.

Figure 8:
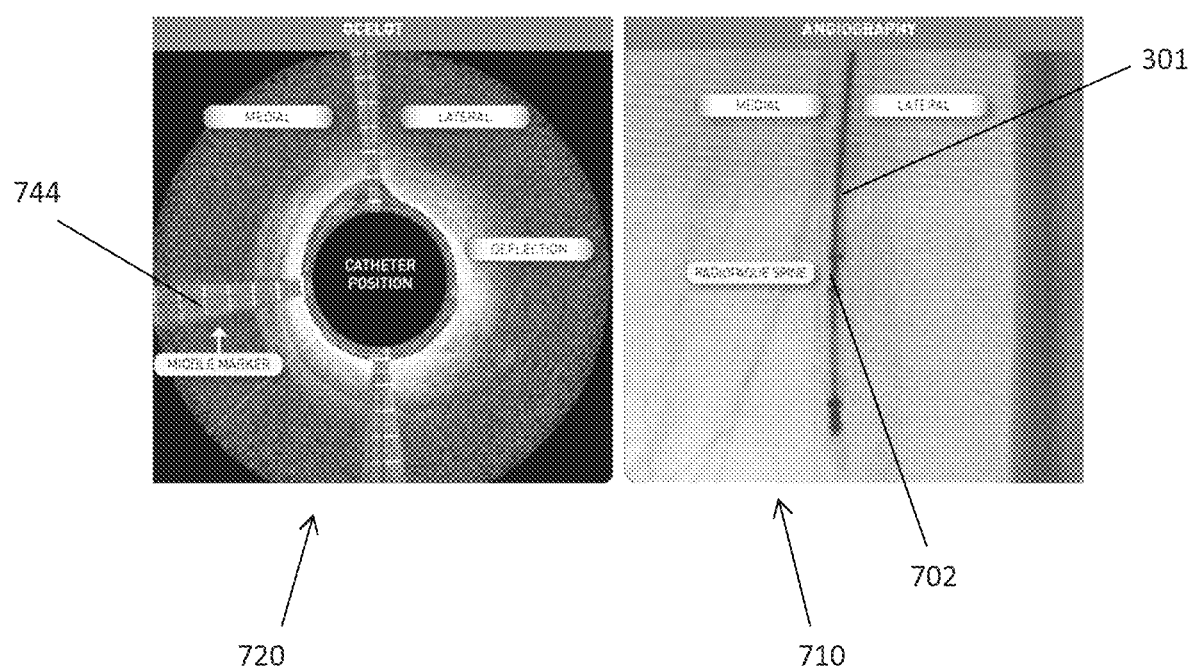
FIG. 8 shows the orientation of an OCT image relative to a fluoroscopy image from a catheter device.

The generated fluoroscopy images and OCT images can be oriented relative to one another, e.g., so that what the user sees on the right side of the OCT image is consistent with what the user sees on the right side of the fluoroscopy image. Referring to FIG. 8, the shaft 301 can include a fluoroscopy marker 702 (also shown in FIG. 2B and FIG. 4) that provides varying contrast in a fluoroscopy image depending on its radial orientation. The marker may be a radiopaque band with one or more asymmetric features such as a "C", "T", or dog bone shape that can be used to radially orient the shaft because the fluoroscopic image of the marker will change depending on its orientation. The fluoroscopy marker 702 can have a fixed location relative to the spines 419 and/or the jog 989. For example, as shown in FIG. 2B, the fluoroscopy marker 702 can be aligned opposite to the jog 989 and/or axially aligned with the second spine 419 described above. The fluoroscopy marker 702 can be used to align a fluoroscopy image 710 with an OCT image 720 during use of the catheter.

As shown in FIG. 8, to align the fluoroscopy image 710 with the OCT image 720, the shaft 301 can be rotated slightly such that the marker 702 is aligned to a particular side of the screen, such as at the 9 o'clock position. The up/down position of the catheter (i.e. whether the catheter is pointed down, as shown in FIG. 7, or pointed up) can also be determined. After the rotational position and the up/down position of the catheter have been determined using the fluoroscopy image 710, the OCT image can then be oriented such that striped ray 744 from the middle marker (the second spine 419 described above) of the shaft 301 is also at the 9 o'clock position in the OCT image 720. Such positioning can be termed "fluorosyncing." Fluorosyncing can be performed using manual input from the user, such as information regarding the up/down position and the rotational position, or can be performed automatically. To orient the OCT image 720 using this information, the software may draw the OCT image 720 either in a clockwise or counterclockwise direction (depending on the up/down orientation of the catheter in the fluoroscopy image 710) and will rotate the image 90°, 180°, or 270° (depending on the rotational position of the catheter in the fluoroscopy image 710).

Once the fluorosync has been completed, the absolute and relative position and orientation of the catheter within the patient's body may be determined. The markers on the chassis/imaging system (visible in the OCT system) may therefore provide sufficient orientation markers such that the fluoroscopic imaging may be reduced.

Figure 21:
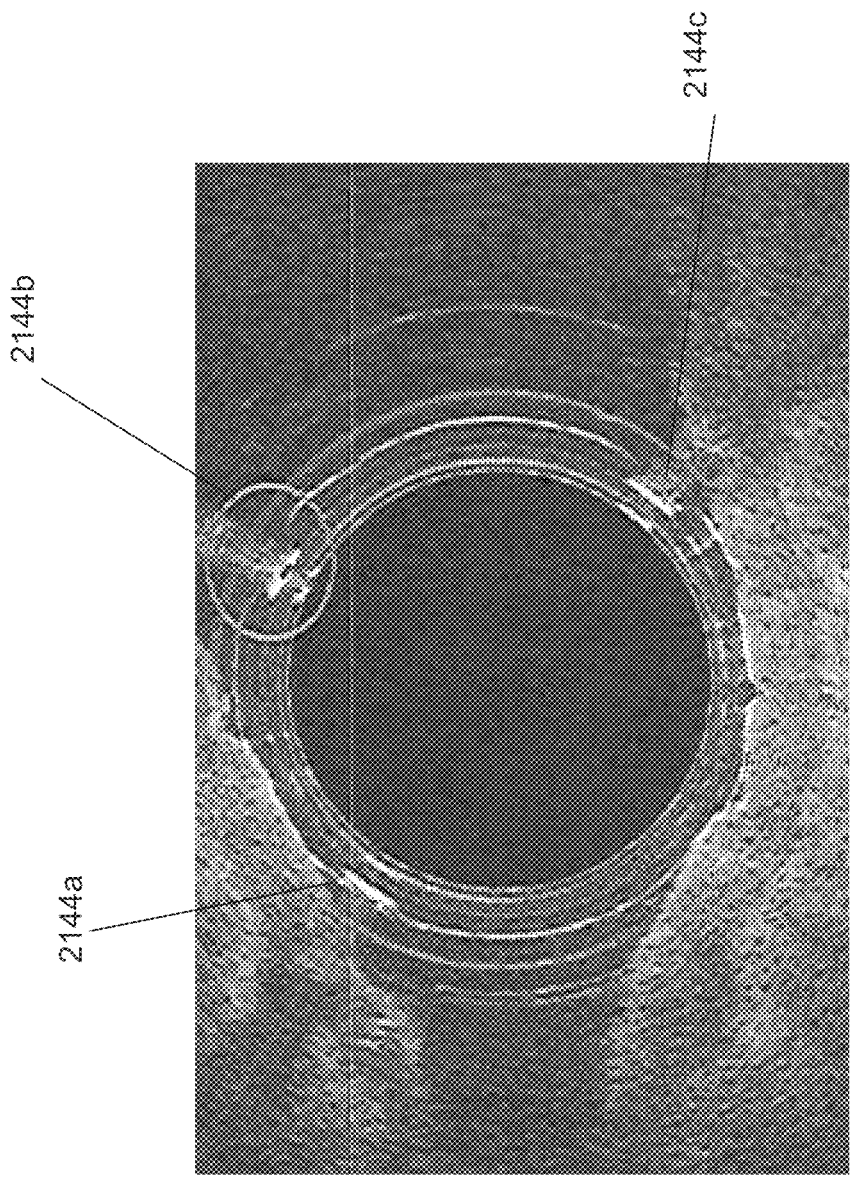
FIG. 21 shows an exemplary OCT image resulting from the spine arrangement shown in FIGS. 20A-20C.
Figure 22A:
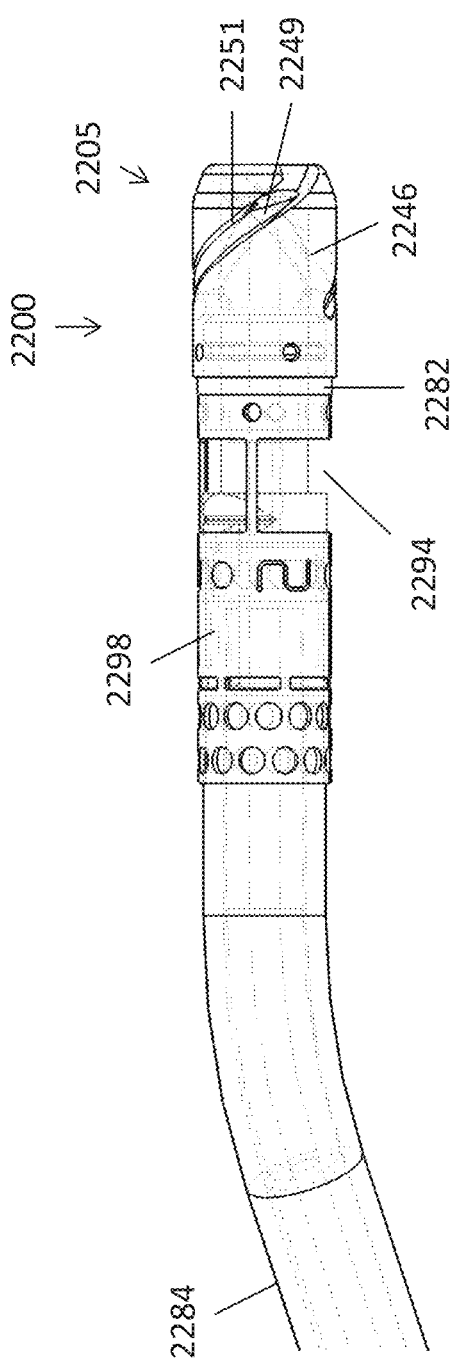
Figure 22B:
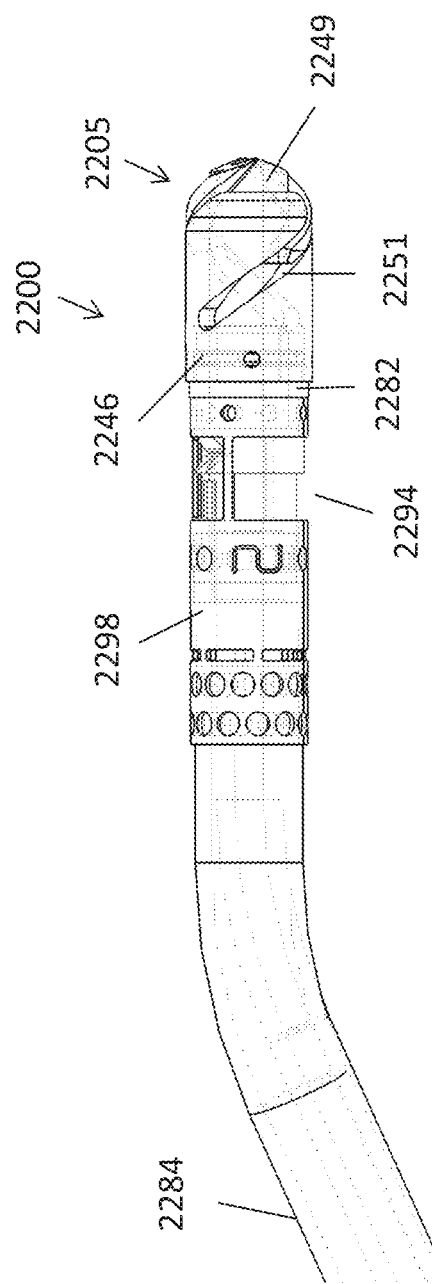
Figure 22E:
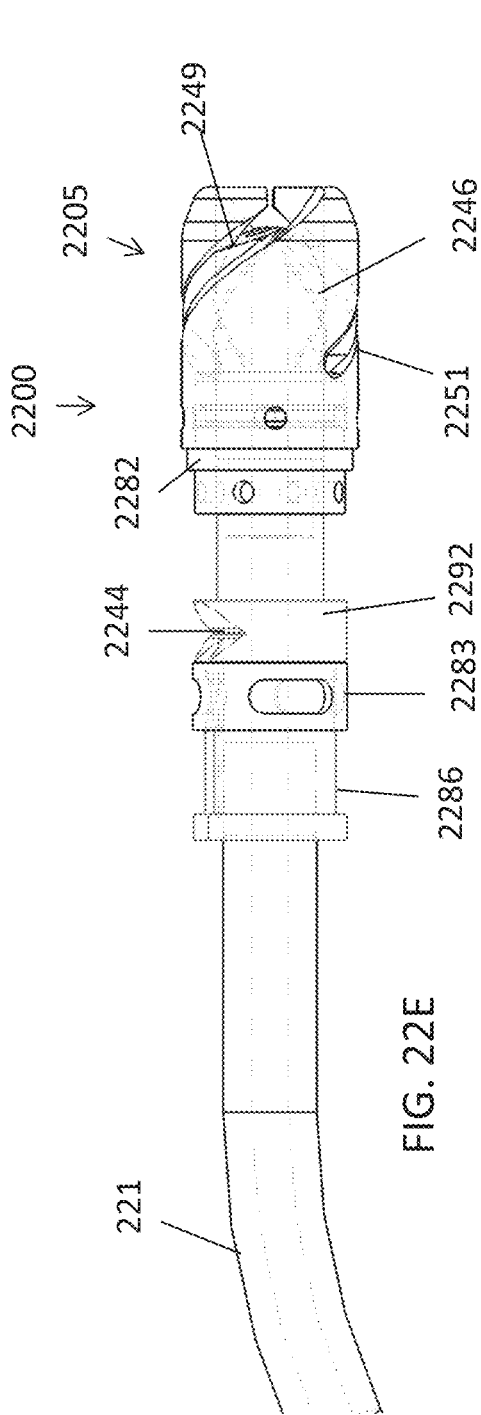
Figure 22F:
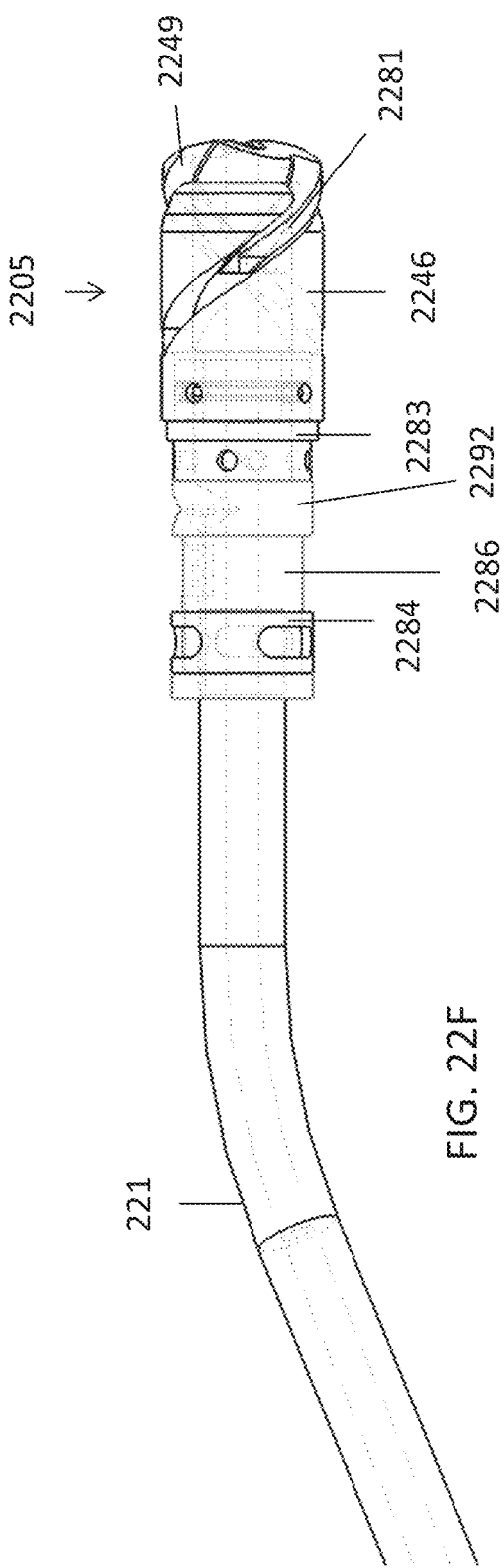

The displayed images can be used, in combination with steering mechanisms such as the OCT markers, the fluoroscopy marker, and the fixed jog of the device, to steer the catheter and rotatable tip to the desired location. Referring to FIG. 9A, the OCT image 920 shows healthy tissue 956 in the form of a layered structure and non-healthy tissue 958 in the form of a nonlayered structure. The cat ears 962 in the image show a region between the healthy and unhealthy tissue caused by a slight expansion of the vessel around the catheter at that location. Accordingly, during a CTO procedure, one goal may be to steer the catheter towards the unhealthy tissue. Because the middle spine 419 is aligned opposite to the jog 989 (as shown in FIG. 2B), the ray 744 corresponding to the middle spine 419 can be oriented opposite to the non-healthy tissue 958 to steer the catheter in the correct direction. Identifying the middle spine can be made easier by differentiating the middle spine relative to the rest of the spines (as described with respect to FIGS. 20A-20C). That is, referring to FIG. 21, having a different spine shape (such as thicker and with a slot therein as in FIGS. 20A-20C) can result in a ray 2144$b$ having a different profile than the rest of the rays 2144$a,c$.

FIG. 9B shows the catheter deflected toward the layered, healthy tissue. FIG. 9C shows the catheter rotated such that it is deflected toward the unhealthy, non-layered structure. Thus, the system may be configured to allow the orientation of the catheter to be rotated into the correct position using the fixed directional markers from the chassis that are visualized by the OCT. In some variations, the distal end of the device may be steerable and may be steered while still rotating the distal end of the device.

Additional steering members may also be included, such as a selective stiffening member, which may be withdrawn/inserted to help steer the device, and/or one or more tendon members to bend/extend the device for steering.

Figure 10:
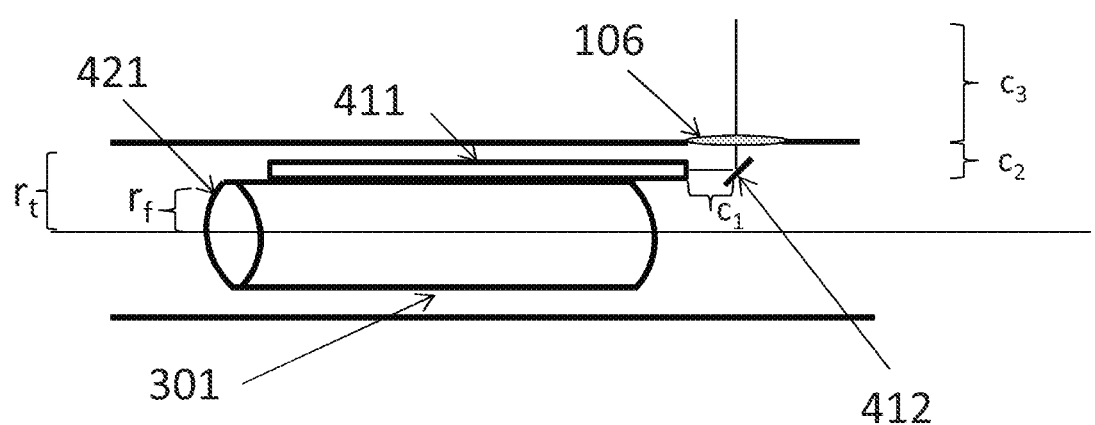
FIG. 10 shows an exemplary diagram used to determine the amount of central masking required for an OCT image of an exemplary catheter device.

Image correction can be performed on the resulting OCT images in order to mask out unwanted or unnecessary portions of the image. For example, referring to FIG. 10, the fiber 411 can be configured such that it ends within the shaft 301. As a result, the fiber 411 will image the distance $c1$ between the fiber 411 distal end and the mirror 412 as well as the axial distance $c2$ between the mirror 412 and the outer diameter of the shaft 301. The resulting image would therefore include portions that correspond to the interior of the shaft. Accordingly, image processing can be performed such that distance $c1$, $c2$, or $c1+c2$ is masked out in the displayed image. In the case where $c1$ and $c2$ are masked out, only the area $c3$ would show up on the image (where the total imaging distance or capability of the fiber is equal to $c1+c2+c3$). For example, up to 100 pixels can be masked out, such as between 20 and 60 pixels, for example approximately 40 pixels.

Additional image processing is possible. For example, the image can be corrected to account for lag of the optical fiber in the amount of rotation at the handle vs. at the distal end of the catheter. Images for lag correction can be captured automatically. Further, images can be exported and stored, for example in a movie format. The images can optionally viewed in adjustable grayscale. Further, the speed of the waterfall view can be adjusted. In some variations, and offset or "ghost" image may be overlaid atop the OCT to indicate the difference between the predicted and actual rotational orientation of the catheter.

The catheter variation described immediately above provides an internal motor for rotating the distal tip. In some variations, a manually rotatable device may be used with an adjunctive device providing a motorized movement of the distal tip. In this variation, the handle portion of the device may set and be secured within a housing that includes a motor and gearing to automatically rotate the distal tip at a predetermined or adjustable speed. Thus, this motorized accessory device may adapt an otherwise manual device to automatically rotate.

In the examples provided above, the distal tip of the device is rotated through multiple complete rotations (both clockwise and counterclockwise) to move the distal tip and/or any attached imaging sensor in rotation around the elongate longitudinal axis of the device. In some variations the distal tip of the device to create an oscillating motion.

In general, the tips described herein can include cutting surfaces configured to slice or grind through tissue as the tip is driven forward. The tips can have a maximum diameter of less than 1", such as less than 0.9" in diameter, such as approximately 0.8".

In one embodiment, the rotating distal end comprises two or more wedges that are radially separated around the tip region (e.g., spaced equally apart radially). It may be advantageous to have three or more wedges spaced around the tip, which may improve centering of the device, as described herein.

In some variations, the rotating distal end can have a distal tip that is roughly corkscrew or helically shaped with spiral flutes extending around the guidewire lumen. The distal tip can be configured to rotate in both the clockwise and counterclockwise directions and to provide a sharper cutting surface in one direction than the other.

For example, referring back to FIGS. 3A-3D, distal tip 305 includes a proximal stem portion 388 configured to slide at least partly into the chassis 405 and to hold the optical fiber for imaging. Two helical flutes 391a,b can extend from the proximal stem portion 388 to the distal end of the tip 1305. The helical flutes 391a,b form a substantially smooth, curved outer surface 322 therebetween that spirals distally to the distal end of the guidewire lumen 363. The smooth curved outer surface 322 provides an atraumatic tissue-contacting surface when rotated in one direction, i.e., the counterclockwise direction in FIGS. 3A-3D. The curved outer surface 322 is rimmed by a sharp edge 403 that extends continuously from the proximal stem portion 388 to the distal end of the tip. The edge 403 provides a tissue-cutting edge when rotated in the opposite direction, i.e. the clockwise direction in FIGS. 3A-3D. The flutes 391a,b form a conic helix such that the diameter of the cutting geometry at the proximal end is approximately the diameter of the catheter outer shaft while the diameter of the cutting geometry at the distal end is reduced to approximately the size of the guidewire lumen.

As another example, referring to FIGS. 12A-12F, a distal tip 1205 includes a proximal stem portion 1288 configured to slide at least partly into a chassis and to hold the optical fiber for imaging. Two conic helical flutes 1291a,b can extend from the proximal stem portion 1288 to the distal end of the tip 1305. The flutes 1291a,b can have a higher pitch relative to the flutes 391a,b of distal tip 305 shown in FIGS. 3A-3D. For example, the pitch can be greater than 0.10 inches for a tip having a maximum diameter of 0.8", such as a pitch of approximately 0.15 inches. Due to the high pitch, each flute 1291a,b can extend less than half way around the circumference of the tip 1205. The helical flutes 1291a,b can be rimmed by cutting rim edges 1271 (see edges 1271a,c for flute 1291a and edge 1271b for flute 1291b in FIG. 12A). Because the helical flutes 1291a,b and cutting rim edges 1271 extend at a steeper angle, the tip 1205 can provide a more aggressive cutting geometry that will slice tissue efficiently and quickly as the tip is drilled through the tissue. The cutting rim edges 1271 can have a slight thickness (in the radial dimension) to them, providing for a buffer to the sharp edges on either side. Such cutting rim edges 1271 can advantageously help prevent the tip 1205 from cutting a sheath as it moves therethrough.

Further, the width of the flutes 1291a,b can be larger relative to the flutes 391a,b of the distal tip 305. For example, the width can be greater than 0.025 inches for a tip having a maximum diameter of approximately 0.8", such as width of greater than 0.030 inches, such as approximately 0.032 inches. The larger width can advantageously provide more space for clearing material or "chips" as the tip rotates through an occlusion, thereby allowing the tip to move more seamlessly through the occlusion.

The flutes 1291a,b can terminate at the distal end prior to reaching the guidewire lumen 1263. Angled flat sections 1293a,b can extend or slope distally from the distal end of each flute 1291a,b at a lower slope that the flutes 1291a,b. The angled flat sections 1293a,b can have a substantially flat surface with knife-like edges 1294a,b (see FIG. 12B) that meet to form pointed tips 1295a,b. The pointed tips 1295a,b can face distally (forward) and can form the distal-most portion of the tip 1205. The pointed tips 1295a,b can advantageously help pierce or cut through tissue as the tip 1205 is rotated. The angled flat sections 1293a,b can be slightly wider than the width of the flutes 1291a,b at the junction between the flat sections 1293a,b and the flutes 1291a,b, thereby creating angled blades 1292a,b (see FIG. 12I) on the distal end of the tip 1205.

The angled flat sections 1293a,b and the knife-like edges 1294a,b can frame or surround a countersink 1297 (otherwise called a counterbore) extending around the guidewire lumen 1263. The countersink 1297 can be an indented volcano-shaped section (e.g., caldera region) that sinks proximally from the knife-like edges 1294a,b and the pointed tips 1295a,b. The countersink 1297 can advantageously help center the tip 1205 on tissue through which it is being driven by allowing the tissue to extend into the countersink 1297 as the tip 1205 is moved distally.

The distal tip 1205 can be configured to cut more aggressively in one direction than in the other. For example, when rotated clockwise in the view of FIG. 12A, the tip 1205 would cut more aggressively than when rotated in the counterclockwise direction.

Figure 12A:
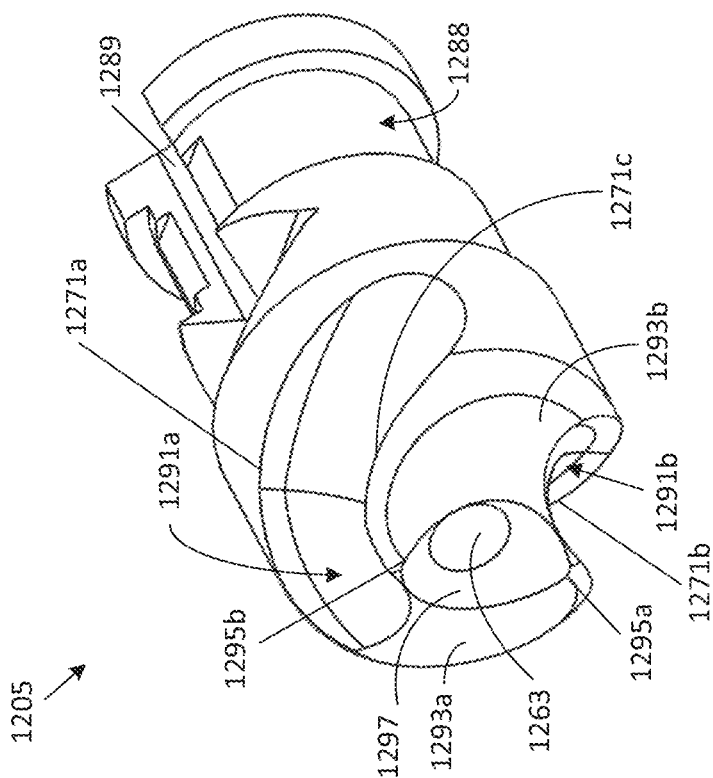
Figure 12F:
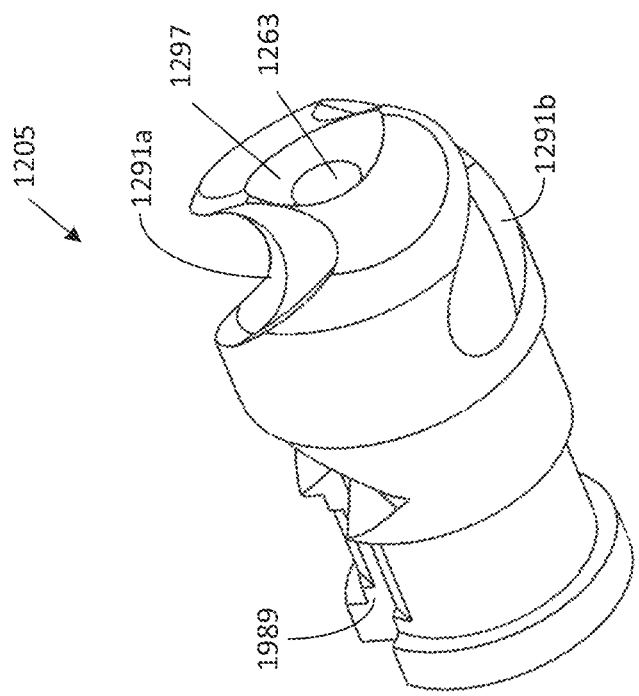
Figure 12E:
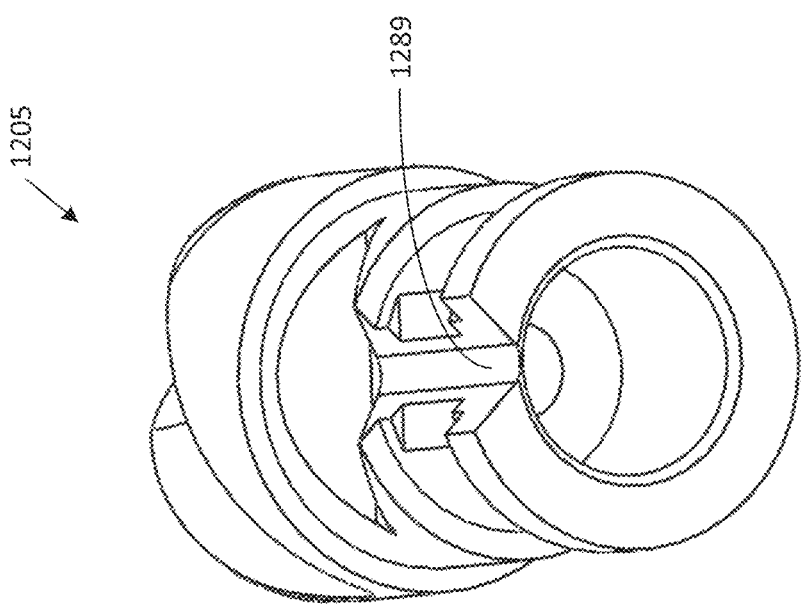

As shown best in FIGS. 12C-12E, the fiber channel 1289 in which the optical fiber sits can extend into the distal tip 1205. The fiber channel 1289 can be rounded along the bottom to allow for large-diameter fibers, such as GRIN fibers, to fit therein without increasing the diameter of the channel along the outer surface of the tip 1205.

Figure 13:
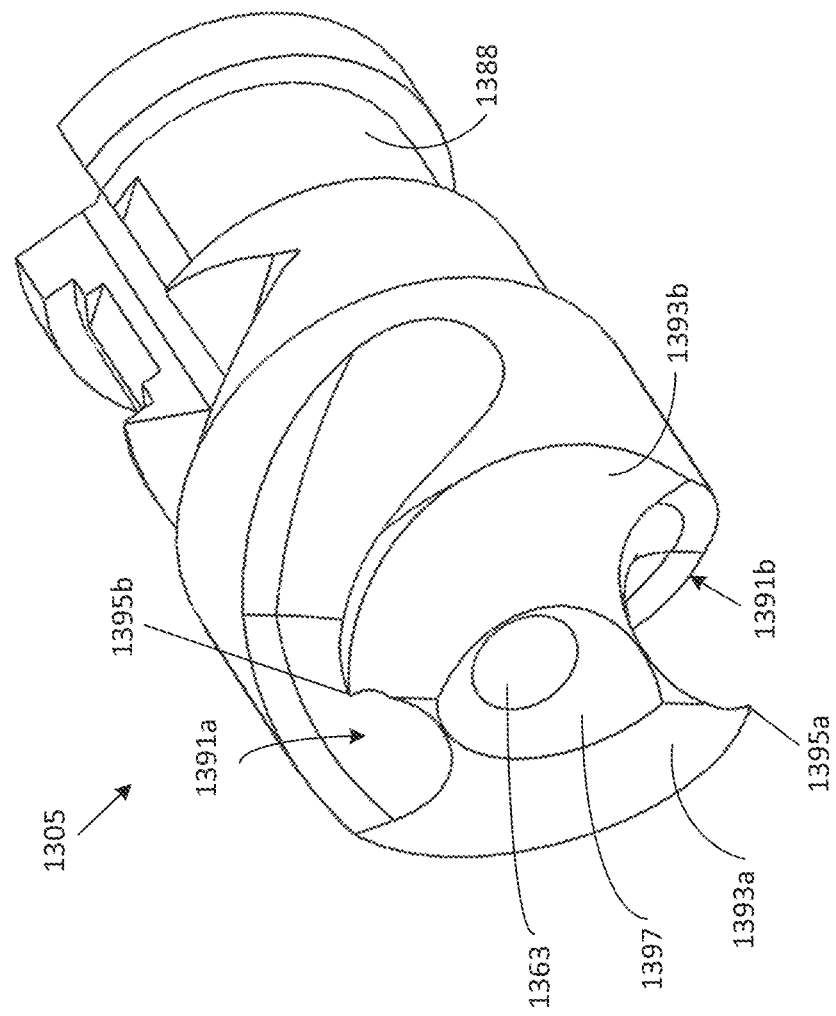
FIG. 13 shows a variation of a rotating tip having helical flutes, a countersink, and an aggressive leading edge.

Referring to FIG. 13, a tip 1305 can include many of the same features as tip 1205, including a proximal stem portion 1388, steep flutes 1391a,b extending therefrom, flat surfaces 1393a,b, sharp pointed tips 1395a,b, and a countersink 1397 around the guidewire lumen 1363. In contrast to tip 1305, however, the flat surfaces 1393a,b can be nearly perpendicular to the central axis of the tip 1305, thereby creating thinner and sharper tips 1395a,b, resulting in a more aggressive tip.

Figure 14:
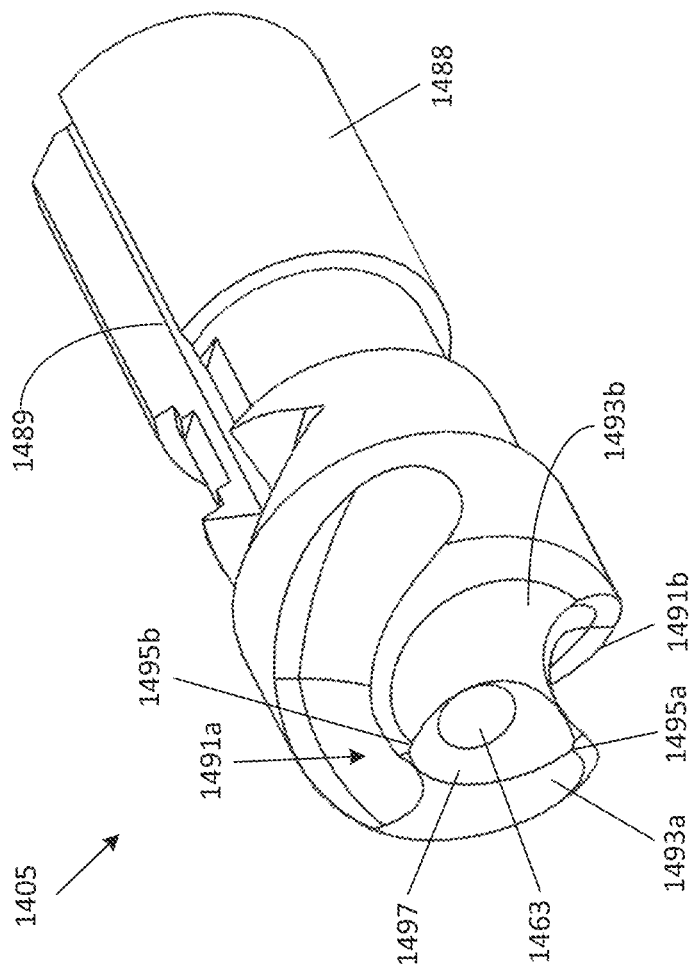
FIG. 14 show a variation of a rotating tip having helical flutes, a countersink, and an elongate proximal stem portion to provide a long optical fiber channel.

Referring to FIG. 14, a tip 1405 can include many of the same features as tip 1205, including a proximal stem portion 1488, steep flutes 1491a,b extending therefrom, angled flat sections 1493a,b, sharp pointed tips 1495a,b, and a countersink 1497 around the guidewire lumen 1463. In contrast to tip 1305, however, the proximal stem portion 1488 can be longer, such as at least 50%, 75% or 100% longer, than the stem portion 1388. For example, the proximal stem portion 1488 can be more than 4 mm, such as greater than 5 mm, such as approximately 6 mm. The longer proximal stem portion 1488 can advantageously provide a longer fiber channel 1489, thus providing additional support for fragile fibers, such as GRIN fibers.

Referring to FIG. 15A, a tip 1805 can include conic flutes extending therein and a rounded distal face. The tip 1805 can include many of the same features as tip 1205, including a proximal stem portion 1888, steep flutes 1891a,b,c extending therefrom, angled flat sections 1893a,b,c, and a countersink 1897 around the guidewire lumen 1863. In contrast to tip 1205, however, there can be three flutes instead of two, which can advantageously lead to more even rotation, less nonuniform rotational distortion (NURD) in the images, better engagement, and better centering of the tip. Further, the angled flat sections 1893a,b,c can be thicker and have sharper, less curved edges. The angled flat sections 1893a, b,c and the flutes 1891a,b,c can end at the countersink 1897. The junction of the flutes 1891a,b,c and the angled flat sections 1893a,b,c can form a plurality of sharp points 1895 around the rim of the countersink 1897, making the tip 1805 more aggressive.

Figures 15B, 15C:
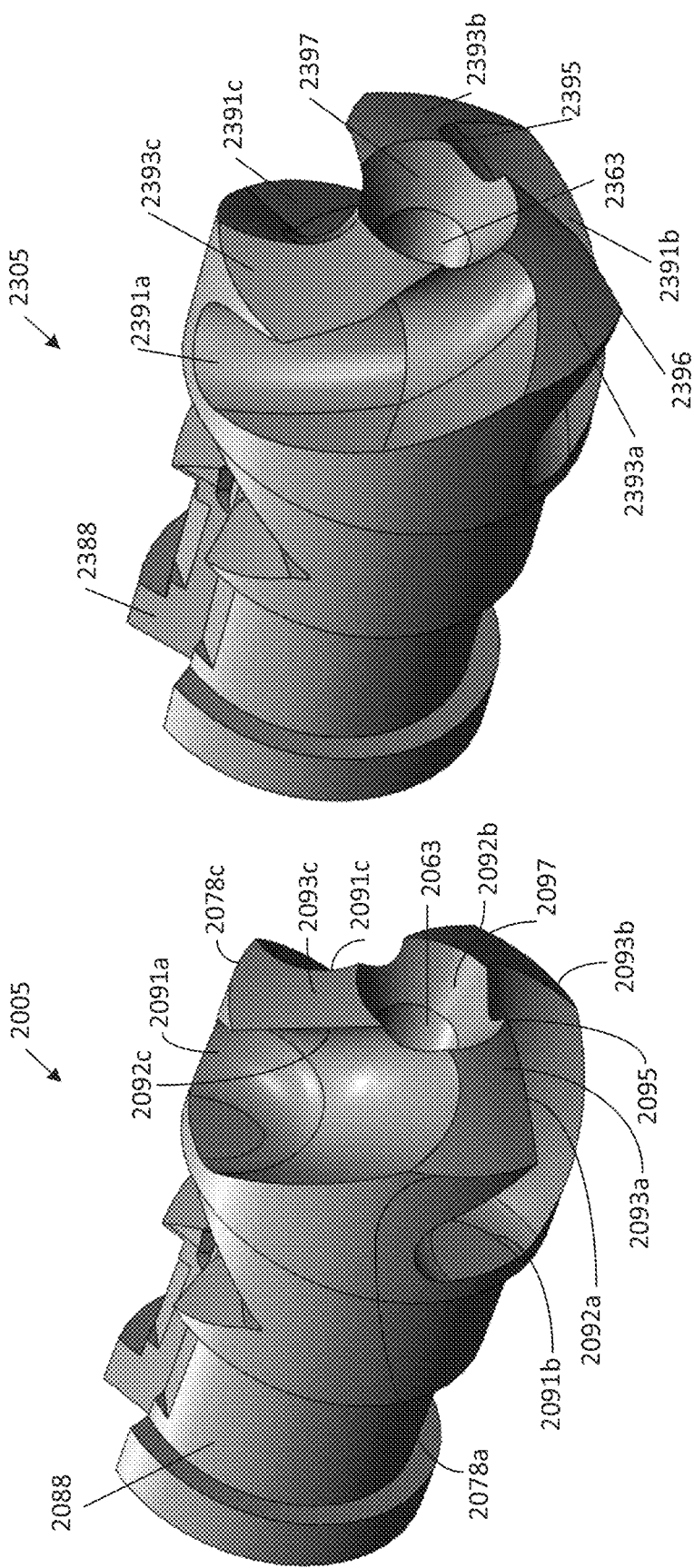

Referring to FIG. 15B, a tip 2005 can include conic flutes extending therein and a flat distal face. The tip 2005 can include many of the same features as tip 1205, including a proximal stem portion 2088, steep flutes 2091a,b,c extending therefrom, angled flat sections 2093a,b,c, and a countersink 2097 around the guidewire lumen 2063. In contrast to tip 1205, however, there can be three flutes instead of two. Further, the flutes 2091a,b can have a steeper slope, thereby advantageously helping to move tissue away from the leading edge of the tip 2005. Further, the angled flat sections 2093a,b,c can be thicker. Further, the angled flat sections 2093a,b,c can each have at least one relatively straight edge 2092a,b,c, along the outer perimeter of the tip 2005, which can create a more aggressive cutting geometry. Similar to the tip 1805 of FIG. 15a, the angled flat sections 2093a,b,c and the flutes 2091a,b,c of tip 2005 can end at the countersink 2097. The junction of the flutes 2091a,b,c and the angled flat sections 2093a,b,c can form a plurality of sharp points 2095 around the rim of the countersink 2097.

Referring to FIG. 15C, a tip 2305 can include conic flutes extending therein and a flat distal face. The tip can include many of the same features as tip 1205, including a proximal stem portion 2388, steep flutes 2191a,b,c extending therefrom, angled flat sections 2393a,b,c, and a countersink 2397 around the guidewire lumen 2363. In contrast to tip 1205, however, there can be three flutes instead of two. Further, the angled flat sections 2393a,b,c can be thicker. The angled flat sections 2393a,b,c can each have at least five sharp corners 2396 configured to create a more aggressive cutting geometry. Similar to the tip 1805 of FIG. 15a, the angled flat sections 2393a,b,c and the flutes 2391a,b,c of tip 2305 can end at the countersink 2397. The junction of the flutes 2391a,b,c and the angled flat sections 2393a,b,c can form a plurality of sharp points 2395 around the rim of the countersink 2397.

Referring to FIG. 15D, a tip 2205 can include flutes extending therein from the proximal end of the tip to the distal end of the tip. The proximal and distal ends can have substantially the same diameter (i.e., not taper towards the distal end). The tip 2205 can include many of the same features as tip 1205, including a proximal stem portion 2288, two steep flutes 2291a,b extending therefrom, angled flat sections 2293a,b,c, and a countersink 2297 around the guidewire lumen 2263. The flutes 2291a,b can end in a flat distal surface 2255 that is substantially perpendicular to the guidewire lumen 2263. The flat distal surface 2255 can have an annular portion 2256 and two wings 2257a,b that extend out to meet the rims 2271a,b between the flutes 2291a,b.

Referring to FIG. 15E, a tip 2105 can include conic flutes extending therein and a rounded distal face. The tip 2015 can include many of the same features as tip 1205, including a proximal stem portion 2188, steep flutes 2191a,b,c extending therefrom, angled flat sections 2193a,b,c, and a countersink 2197 around the guidewire lumen 2163. In contrast to tip 1205, however, there can be three flutes instead of two. Further, the flutes 2191a,b can have a steeper slope, thereby advantageously helping to move tissue away from the leading edge of the tip 2005. Further, the angled flat sections 2193a,b,c can be very thin, almost forming a knife-like surface to help incise tissue. Similar to the tip 1805 of FIG. 15a, the angled flat sections 2193a,b,c and the flutes 2191a, b,c of tip 2105 can end at the countersink 2197. The junction of the flutes 2191a,b,c and the angled flat sections 2193a,b,c can form a ring configured to center the device in the tissue.

Other tip embodiments are possible. For example, referring to FIGS. 16A-17C, some tips can be designed so as to effectively grind through hard tissue.

Referring to FIGS. 16A-16B, a tip 1505 can be configured to grind through hard tissue, such as calcium or fibrous tissue. The tip 1505 can thus include slanted surfaces 1571, such as four slanted surfaces, that frame the guidewire lumen 1463. The slanted surfaces 1571 can come together at sharp edges 1573 (which extend proximally from the guidewire lumen 1463). As shown in FIGS. 16A-16B, the surfaces 1571 can end in curved edges 1575 that form distal-facing arcs. The surfaces 1571 can be either approximately flat (as shown in FIG. 16A) or can be concave (as shown in FIG. 16B). The concave formation shown in FIG. 16B can result in more discrete, sharp cutting edges 1573. When rotated (clockwise and/or counterclockwise), the edges 1571 can advantageously slice back and forth through hard tissue, thereby grinding away at the tissue. The edges 1575 can be used to cut and/or clear material to the side.

At the distal end, near the guidewire lumen opening, the sharp edges of each surface (or cut out region) may also have a sharp distal-facing edge, and these distal-facing edges may meet at discrete sharp points 1577. In FIG. 16B, the more concave the surface forming these edges are, the steeper and more pronounced (more distal facing) the points will be. These points may also help cut through hard regions. As shown in FIGS. 16A-16B, the tip 1505 can be substantially symmetric therearound such that it will cut with substantially the same aggressiveness whether rotated in the forward or reverse directions.

Any of these variations may also include a countersink region before the guidewire opening (not shown in FIGS. 15A-15B).

Referring to FIGS. 17A-17C, a tip 1605 can be configured to grind through hard tissue, such as calcium or fibrous tissue. The tip 1605 can include a distal-most surface 1671 that is substantially perpendicular to the guidewire lumen 1663. A countersink 1297 can extend through the center of the surface 1671 around the guidewire lumen 1663.

As shown best in FIGS. 17B-17C, the surface 1671 can include a pattern of divots 1673 therein that meet to form a plurality of sharp points 1675. In some embodiments (as shown in FIGS. 17A-17C), the divots 1673 and sharp points 1675 can be formed of an array of pyramidal features machined into the surface 1671. In other embodiments, the divots and sharp points can be formed by an array of spirals arranged at a shallow pitch. The array of sharp points 1675 can advantageously be used to grind or slice through hard tissue as the tip is rotated clockwise and/or counterclockwise.

Proximal of the surface 1671, the tip 1605 can include conic flutes 1691 spiraling around the proximal end of the tip, such as four conic flutes 1691a,b,c,d. The conic flutes 1691 can be arranged such that the diameter of the cutting geometry at the proximal end is approximately the diameter of the catheter outer shaft while the diameter of the cutting geometry at the distal end (at surface 1671) is reduced, such as reduced by 30-60%. The conic flutes 1691 can advantageously facilitate the advancement of the device and can provide clearing of tissue away from the grinding surface 1671.

In some embodiments, rotating tips can be designed to push material aside rather than pull through material. For example, referring to FIGS. 18A-18B, a tip 1705 can include paddles 1761 extending from a proximal end of the tip 1705 to a distal end (around the guidewire lumen 1763). The paddles 1761 can have thin outer surfaces that slope towards a distal-facing rim 1767 that extends around the guidewire lumen 1763 at the distal end of the tip. As shown in FIGS. 18A and 18B, the rim 1767 can have a diameter that is smaller than a diameter of the tip 1705 at the proximal end.

A large notch 1769 can extend between each paddle 1761. The notches 1769 can advantageously provide space for plaque, etc. to move into as the tip 1705 bores through an occlusion. The tip 1705 can include any number of paddles, such as two (as shown in FIG. 18B) or four (as shown in FIG. 18A).

As shown in FIGS. 18A-18B, the tip 1705 can be substantially symmetric therearound such that it will cut with substantially the same aggressiveness whether rotated in the forward or reverse directions.

Figure 11A:
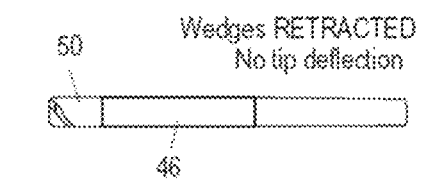
FIGS. 11A-11C illustrate one variation of an exemplary catheter having a rotating distal tip region (housing and wedges extendable from the housing) with the rotating wedges retracted into a rotating housing (FIG. 11A); with the rotating wedges extending from the rotating housing (FIG. 11B); and with the distal end region deflecting (FIG. 11C).
Figure 11B:
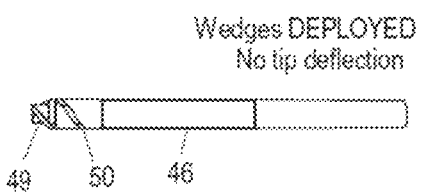
Figure 11C:
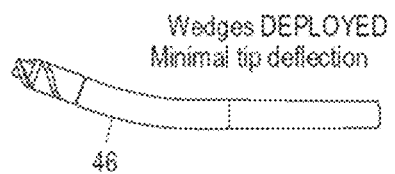

In some variations, the rotatable distal tip includes a fixed or rotatable housing from which dissection elements may retract or extend relative to an outer housing (i.e., the wedges can actively retract or extend from the housing or the housing can cover the wedges such that the wedges are in a retracted configuration and uncover the wedges such that the wedges are in an extended configuration). An imaging element, such as an OCT imaging element, may be included in this embodiment as well. Referring to FIGS. 11A-11C, in some variations, wedges 49 may be extended from a rotatable distal tip 50. In FIG. 11A, the device is shown with the wedges retracted into (or covered by) the rotatable distal tip 50. In FIG. 11B, the wedges 49 have been extended from the housing 46. The distal end of the device can be shared and is shown deflecting upwards (steering in one plane) in FIG. 11C while the wedges are extended from the housing.

Both the distal tip and the wedges can be configured to rotate. The wedges 49 (which may be sharp blades or may be blunt) can be extended from the distal housing and locked in any position (extended, partially extended or retracted) and rotated clockwise and/or counterclockwise while locked in a retracted, extended or partially extended position.

The wedges may be fully or partially retracted into a distal housing. The extension of the wedge from the distal housing may be limited. For example, the wedges may be prevented from extending fully out of the distal housing, thereby preventing material (such as a plaque or tissue) from getting caught between the wedges and the housing.

The wedges at the distal end may be referred to as a blade or blades, even though they may be substantially blunt. In some variations the wedges are configured so that they are forward-cutting, but not side-cutting. This means that they may include a forward-facing cutting edge, and the more lateral edges may be blunted or less sharp. In some variations, the rotating distal tip includes only a single wedge, rather than multiple wedges. The wedge (blade) may be helically arranged at the distal tip.

Figure 19A:
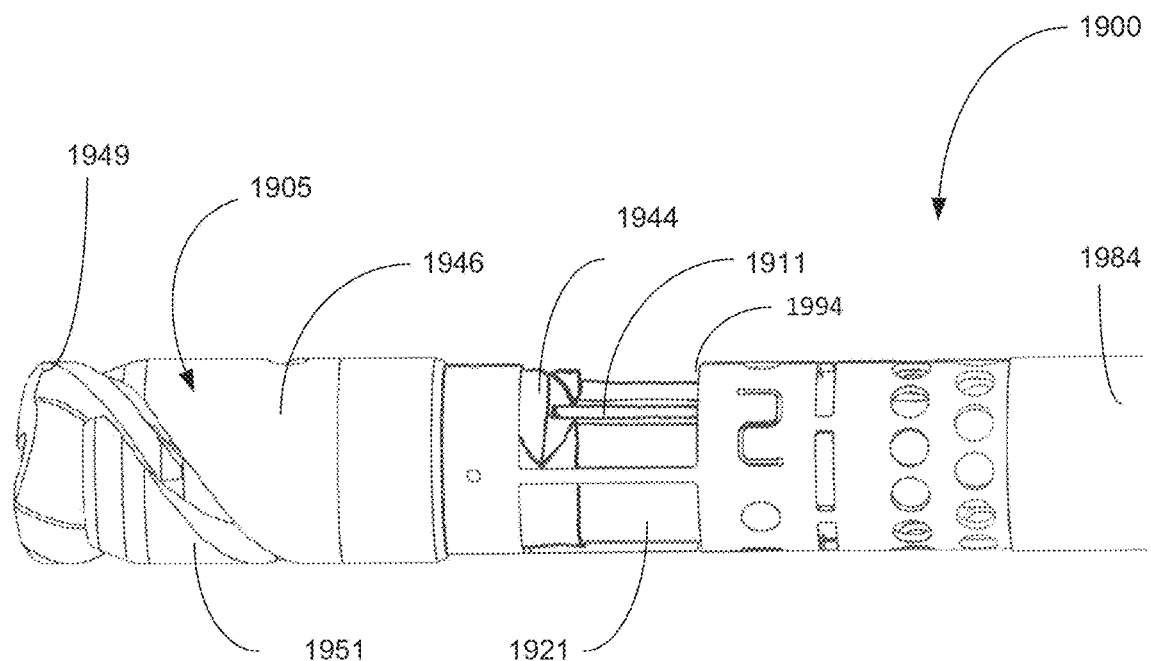
FIGS. 19A-19B show the distal end of an exemplary occlusion-crossing catheter having a rotating distal tip and extendable wedges.
Figure 19B:
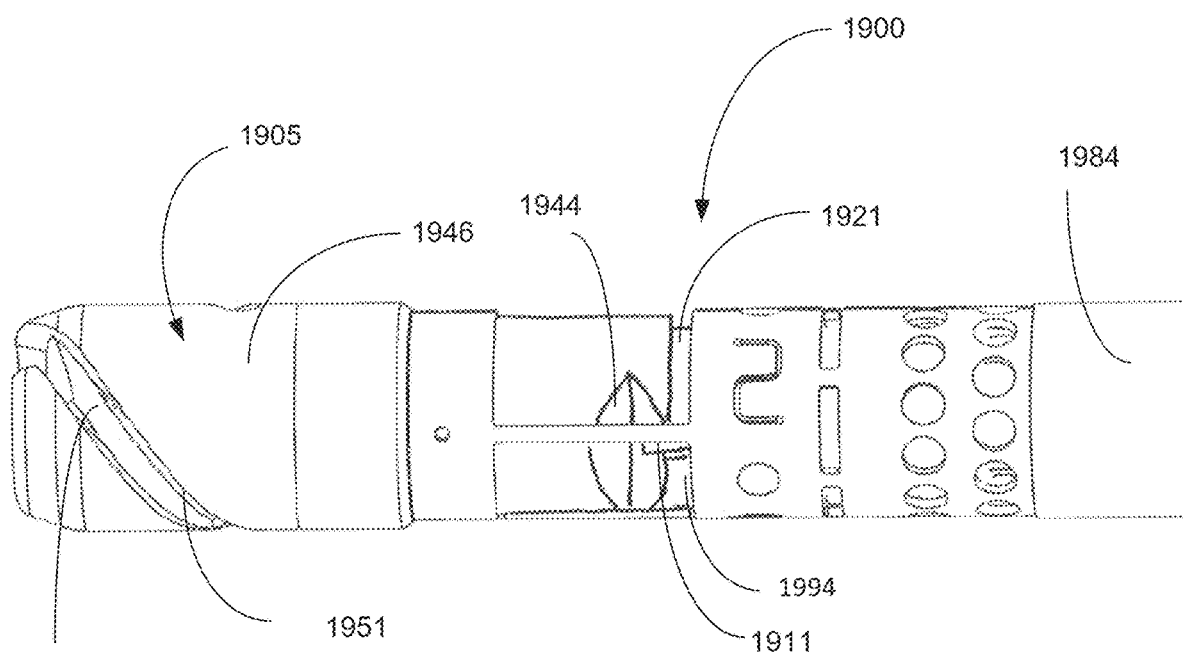
Figure 19C:
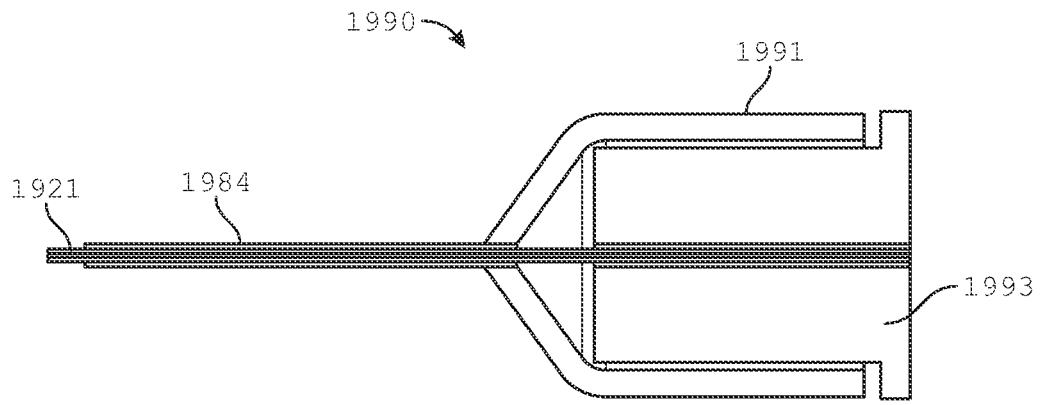
FIGS. 19C-19D show a torque knob for use in moving the outer shaft of an exemplary occlusion-crossing catheter such as the catheter in FIGS. 19A-19B.

FIGS. 19A-19C show a specific embodiment of an occlusion crossing catheter 1900 having extendable wedges. The catheter 1900 can include a tip 1905 having a housing 1946 and wedges 1949 that are extendable out of the housing 1946, such as in and out of spiral or helical slots 1951. The housing 1946 can be mechanically coupled to the outer shaft 1984 of the catheter body while the wedges 1949 can be mechanically coupled to the drive shaft 1921. Axial and rotational movement of the outer shaft 1984 relative to the drive shaft 1921 can thus extend the wedges 1949 out of the housing 1946. For example, referring to FIGS. 19A and 19B, if the wedges 1949 are extended out of the housing 1946 (as shown in FIG. 19A), then the outer shaft 1984 can be rotated counterclockwise and moved distally to bring the wedges 1949 into the housing 1946 (as shown in FIG. 19B).

The catheter 1900 can further include imaging, such as optical coherence imaging. Thus, an optical fiber 1911 can be fixed within a notch 1944. Light from the optical fiber can reflect off of a mirror within the notch and through the imaging window 1994. As the drive shaft 1921 rotates, the distal end of the optical fiber 1911 will also rotate, thereby allowing for circumferential imaging.

Advantageously, by having the outer shaft 1984 move axially and rotate rather than the drive shaft 1921 to extend or retract the wedges 1949, the fiber 1911 can be kept at a fixed length relative to the handle and/or light source. Further, rotation of the drive shaft 1921 can be reserved for rotating the tip 1905 for cutting with the wedges 1949 and/or imaging with the optical fiber 1911.

In order to accommodate for axial movement of the outer shaft 1984 relative to the drive shaft 1921, the imaging window 1994 can have a length greater than or equal to the length of the extended wedges 1949. Accordingly, as the wedges 1949 go from an extended position to a retracted position, the distal end of the optical fiber 1911 and at least a portion of the notch 1944 will remain within the imaging window 1994, as shown by the movement of the window 1994 relative to the distal end of the optical fiber 1911 and notch 1944 from FIG. 19A to FIG. 19B.

Figure 19D:
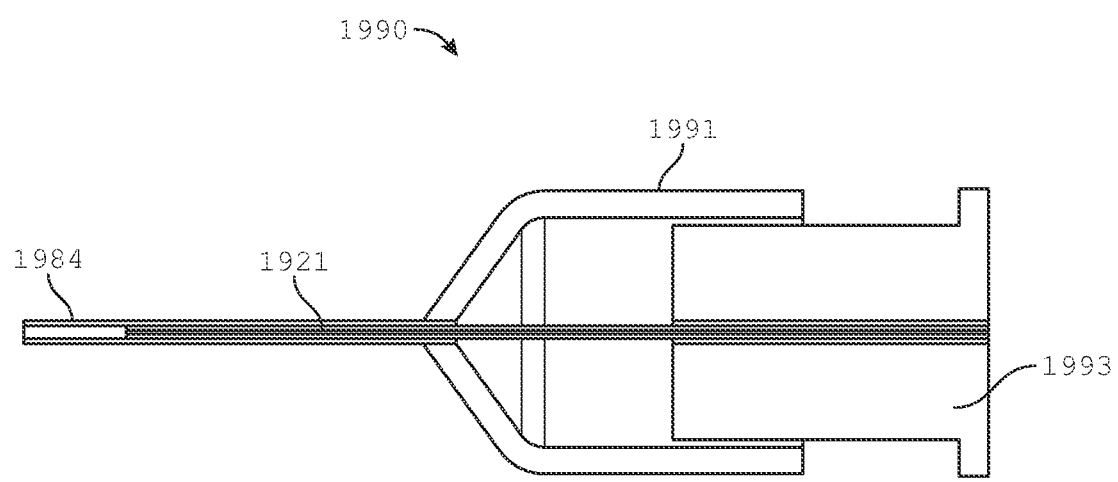

Referring to FIGS. 19C and 19D, in some embodiments, movement of the outer shaft 1984 to extend or retract the wedges 1949 can be accomplished through the use of a torque knob 1990. The torque knob 1990 can include an outer barrel portion 1991 and an inner stationary portion 1993. The inner stationary portion 1993 can be connected, for example, to the catheter handle. The axial position of the stationary portion 1993 can be fixed relative to the drive shaft 1921 as well as the optical fiber 1911. In contrast, the outer barrel portion 1991 can be connected to the outer shaft 1984. The outer barrel portion 1991 can be configured to rotate and/or translate axially, thereby rotating and/or translating the outer shaft 1984. Thus, if the barrel 1991 is in a proximal position (as shown in FIG. 19C), the outer shaft will also be in a proximal position, thereby leaving the wedges 1949 exposed (as shown in FIG. 19A). In contrast, if the barrel 1991 is moved to a distal position (as shown in FIG. 19D), then the outer shaft 1984 will move distally, thereby moving the housing 1946 over the wedges 1949 (as shown in FIG. 19B).

The catheter 1900 can additionally or alternatively include some or all of the features of the other catheter embodiments described herein, such as catheter 100.

FIGS. 22A-22F show another specific embodiment of an occlusion crossing catheter 2200 having extendable wedges. Similar to the catheter 1900, the catheter 2200 can include a rotatable tip 2205 having a housing 2246 and wedges 2249 that are extendable out of the housing 2246, such as in and out of spiral slots 2251.

The housing 2246 can be mechanically coupled to the outer shaft 2284, such as through a distal bushing 2282. The distal bushing 2282 can fix the housing 2246 axially to the outer shaft 2284 while allowing relative rotation between the housing 2246 and the outer shaft 2284. Further, the wedges 2249 can be fixed to the drive shaft 221 (i.e., fixed rotationally and axially). Rotation of the drive shaft 221 can rotate the rotatable tip 2205 relative to the outer shaft 2284. That is, the wedges 2249 can engage the spiral slots 2251 to allow the housing 2246 to rotate with the wedges 2249 and with the distal bushing 2282. Thus, the rotatable tip 2205 can both be rotated when the wedges 2249 are in an extended configuration for aggressive dissecting or cutting and be rotated when the wedges 2249 are in a retracted configuration for less aggressive or passive dissecting or cutting.

An imaging collar 2292 can be fixed (i.e., axially and rotationally) between the drive shaft 221 and the wedges 2249. The imaging collar 2292 includes an imaging sensor attached thereto and can rotate as part of the rotatable tip 2205. As described above with respect to catheter 100, the imaging sensor can include a distal end of an OCT fiber fixed or embedded within a notch 2244 in the imaging collar 2292 and a mirror 2298 within the notch configured to reflect light from the fiber and into the sample being imaged. Further, an attachment collar 2298 can be fixed (i.e. axially and rotationally) to the elongate catheter shaft 2284 and can cover a portion of the imaging collar 2292. A window 2294 in the attachment collar 2298 can allow light reflected off of the mirror to travel therethrough into the sample. As the drive shaft 221 rotates, the distal end of the optical fiber will also rotate, thereby allowing for circumferential imaging with the OCT sensor. As described above with respect to catheter 100, the optical fiber can wrap around a central guidewire lumen as the rotatable distal end 2205 rotates clockwise and counterclockwise.

Axial movement of the outer shaft 2284 relative to the drive shaft 221 can extend the wedges 2249 out of the housing 2246. For example, the outer shaft 2284 can be pushed distally to thereby push the housing 2246 over the wedges 2249. To compensate for the spiral configuration of the spiral slots 2251, the housing 2246 can passively rotate over the bushing 2282 (through engagement with the wedges 2246) as the outer shaft 2284 moves axially. Accordingly, no active rotate of the outer shaft 2284 is required to extend the wedges 2249. Likewise, the outer shaft 2284 can be pulled proximally without active rotation of the outer shaft 2284 to pull the housing 2246 off of the wedges 2249.

Figure 23A:
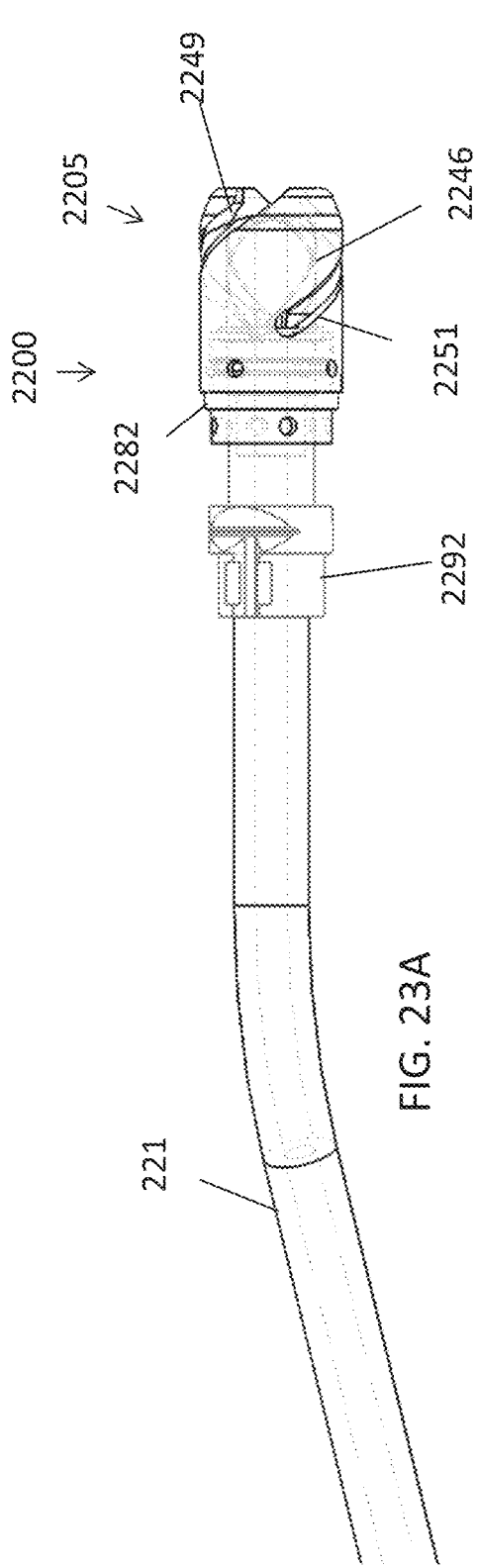
FIGS. 23A-23B show another embodiment of an exemplary occlusion-crossing catheter having a rotating distal tip and extendable wedges.
Figure 23B:
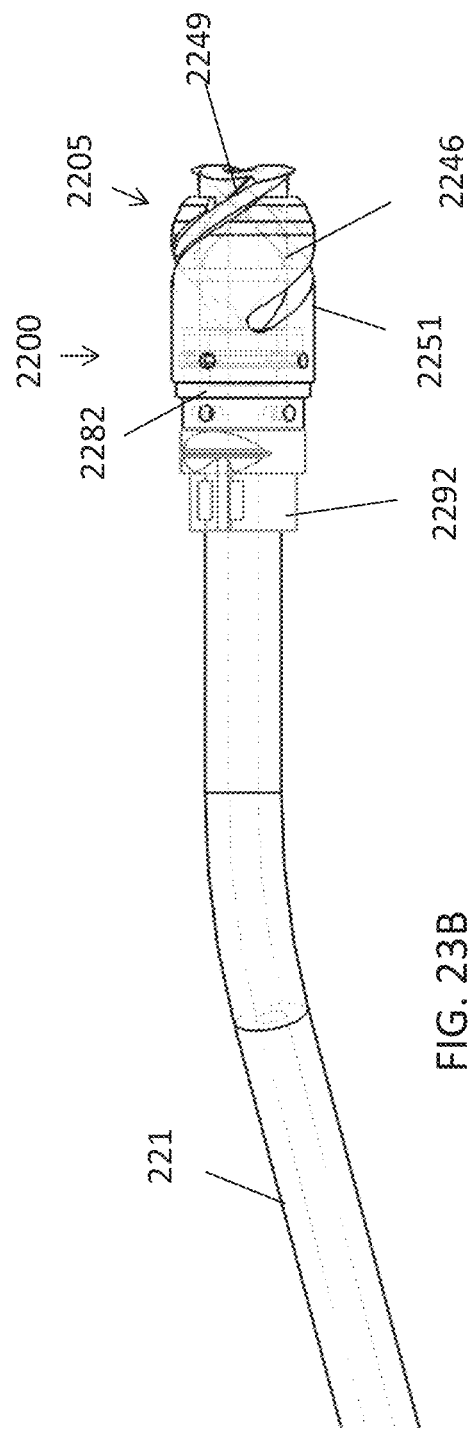

In one embodiment, the amount of movement of the outer shaft 2284 can be limited by a proximal bushing 2283 attached to the housing 2246. The proximal bushing 2283 can slide within a slot 2286 fixed to the imaging collar 2292. The bushing 2283 will thus move distally as the housing 2246 moves distally to cover the wedges 2249 (see FIG. 22E) and move proximally as the housing 2246 moves proximally to expose the wedges 2249 (see FIG. 22F). As the bushing 2283 hits either edge of the slot 2286, the housing 2246 will be prevented from moving further. Referring to FIGS. 23A and 23B, in another embodiment, a single bushing 2282 can be used in the catheter 2200 to limit axial movement of the housing 2249. Using a single bushing can advantageously reduce the size of the catheter at its distal end.

Advantageously, by having the outer shaft 2284 move relative to the inner shaft 221 to extend the wedges 2249, the imaging sensor can remain in a fixed location relative to the wedges 2249 whether the wedges 2249 are extended or retracted. Maintaining the fixed location advantageously allows for a consistent view of the area of tissue being dissected or cut with the wedges 2249. In order to accommodate for axial movement of the outer shaft 2284 relative to the drive shaft 221 while maintaining visualization, the imaging window 2294 can have a length greater than or equal to the length of the extended wedges 2249. Accordingly, as the wedges 2249 go from an extended position to a retracted position, the imaging sensor (i.e., the distal end of the optical fiber) and at least a portion of the notch 2244 will remain within the imaging window 2294, as shown by the movement of the window 2294 relative to the distal end of the optical fiber 2211 and notch 2244 from FIG. 22A to 22B.

The extension, retraction, and rotation of the wedges 2249 can be accomplished through the use of a handle, for example a handle having a knob 1990 or similar control. Thus, to extend or retract the wedges, the outer shaft 2284 can be moved axially relative to the handle while the drive shaft 221 remains stationary relative to handle. The catheter 2200 can additionally or alternatively include some or all of the features of the other catheter embodiments described herein, such as catheter 100. For example, the catheter 2200 can include a fixed jog 2289 therein with spines in the window 2294 aligned so as to help with steering of the catheter 2200.

Although the features of the tips described herein are illustrated with respect to specific examples, it is to be understood that some or all of the features of one or more tips described herein can be combined with some or all of the features of one or more other tips described herein. Further, in general, it is to be understood that the tips described herein can exhibit varying levels of rake angles depending on how sharp or the longevity of the tip is desired to match the material to be cut. For example, a less aggressive tip with negative rake angle could be used on softer material for longer lesion. On the other hand, a more aggressive tip with positive rake angle could be used on harder material for a short lesion.

As noted above, the devices described herein can be used with optical coherence tomography (OCT) imaging. Exemplary OCT imaging systems are described in U.S. patent application Ser. No. 12/790,703, titled "OPTICAL COHERENCE TOMOGRAPHY FOR BIOLOGICAL IMAGING," filed May 28, 2010, Publication No. US-2010-0305452-A1, U.S. patent application Ser. No. 12/829,267, titled "CATHETER-BASED OFF-AXIS OPTICAL COHERENCE TOMOGRAPHY IMAGING SYSTEM," filed Jul. 1, 2010, Publication No. US-2010-0021926-A1, International Patent Application titled "OPTICAL COHERENCE TOMOGRAPHY WITH GRADED INDEX FIBER FOR BIOLOGICAL IMAGING," filed herewith, all of which are incorporated by reference in their entireties.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the examples described herein, but only by the plain meaning of the claim terms employed.

What is claimed is:

1. A rotatable tip for occlusion-crossing comprising:
a proximal stem configured to attach to an occlusion-crossing catheter;
a plurality of flutes extending from a distal end of the proximal stem towards a distal end of the rotatable tip, wherein each flute extends less than half way around a circumference of the tip;
a plurality of angled sections, each angled section extending from a distal end of a flute of the plurality of flutes distally to the distal end of the rotatable tip;
a guidewire lumen extending through the tip from a proximal end of the proximal stem to the distal end of the rotatable tip;
a countersink at the distal end of the rotatable tip surrounding the guidewire lumen, the countersink bordered at least partially by edges of the angled sections; and
a plurality of pointed tips bordering the countersink, each of the plurality of pointed tips formed by a junction between an angled section of the plurality of angled sections and a flute of the plurality of flutes.

2. The rotatable tip of claim 1, wherein a pitch of the plurality of flutes is greater than 0.10 inches.

3. The rotatable tip of claim 1, wherein a surface of each of the angled section is substantially flat.

4. The rotatable tip of claim 1, wherein the rotatable tip is configured to cut more aggressively when rotated in one direction than another.

5. The rotatable tip of claim 1, wherein the rotatable tip further includes a fiber channel along an outer surface thereof, the fiber channel configured to hold an optical fiber therein.

6. The rotatable tip of claim 5, wherein the fiber channel extends along the proximal stem substantially parallel with a longitudinal axis of the tip.

7. The rotatable tip of claim 1, wherein there are only 2-3 flutes in the plurality of flutes.

8. The rotatable tip of claim 1, wherein a portion of the tip along which the plurality of flutes extend is tapered so as to have a smaller diameter at a proximal end of the portion than a distal end of the portion.

9. A rotatable tip for occlusion-crossing comprising:
a proximal stem configured to attach to an occlusion-crossing catheter;
a plurality of flutes extending from a distal end of the proximal stem towards a distal end of the rotatable tip, wherein each flute extends less than half way around a circumference of the tip;
a guidewire lumen extending through the tip from a proximal end of the proximal stem to the distal end of the rotatable tip; and
a countersink at the distal end of the rotatable tip surrounding the guidewire lumen,
a plurality of flat surface sections, each flat surface section extending from a distal end of a flute of the plurality of flutes distally to the countersink.

10. The rotatable tip of claim 9, wherein the plurality of flat surface sections extend at an angle from a distal end of the flutes to the countersink.

11. The rotatable tip of claim 9, wherein the plurality of flat surface sections extend substantially perpendicular to the guidewire lumen.

12. The rotatable tip of claim 9, wherein a pitch of the plurality of flutes is greater than 0.10 inches.

13. The rotatable tip of claim 9, wherein the rotatable tip is configured to cut more aggressively when rotated in one direction than another.

14. The rotatable tip of claim 9, wherein the rotatable tip further includes a fiber channel along an outer surface thereof, the fiber channel configured to hold an optical fiber therein.

15. The rotatable tip of claim 14, wherein the fiber channel extends along the proximal stem substantially parallel with a longitudinal axis of the tip.

16. The rotatable tip of claim 9, wherein there are only 2-3 flutes in the plurality of flutes.

17. The rotatable tip of claim 9, wherein junctions between the flutes and the flat surface sections forms a plurality of sharp points around the countersink.

18. The rotatable tip of claim 9, wherein a portion of the tip along which the plurality of flutes extend is tapered so as to have a smaller diameter at a proximal end of the portion than a distal end of the portion.

* * * * *